United States Patent
Cooper et al.

(10) Patent No.: US 12,378,234 B2
(45) Date of Patent: Aug. 5, 2025

(54) CRYSTALLINE POLYMORPHS OF A 1-THIAZOL-2-YL-PYRAZOLE-5-CARBOXYLIC ACID DERIVATIVE

(71) Applicant: Bantam Pharmaceutical, LLC, New York, NY (US)

(72) Inventors: Alan Cooper, Kenilworth, NJ (US); Zheqiong Wu, Cranbury, NJ (US); Shanming Kuang, Cranbury, NJ (US)

(73) Assignee: Bantam Pharmaceutical, LLC, New York, NY (US)

( * ) Notice: Subject to any disclaimer, the term of this patent is extended or adjusted under 35 U.S.C. 154(b) by 734 days.

(21) Appl. No.: 17/614,973

(22) PCT Filed: May 29, 2020

(86) PCT No.: PCT/US2020/035343
§ 371 (c)(1),
(2) Date: Nov. 29, 2021

(87) PCT Pub. No.: WO2020/243584
PCT Pub. Date: Dec. 3, 2020

(65) Prior Publication Data
US 2022/0162204 A1    May 26, 2022

Related U.S. Application Data

(60) Provisional application No. 62/855,671, filed on May 31, 2019.

(51) Int. Cl.
*C07D 417/04* (2006.01)

(52) U.S. Cl.
CPC ........ *C07D 417/04* (2013.01); *C07B 2200/13* (2013.01)

(58) Field of Classification Search
None
See application file for complete search history.

(56) References Cited

FOREIGN PATENT DOCUMENTS

WO    2018102453 A1    6/2018

OTHER PUBLICATIONS

PCT International Search Report and Written Opinion, Application No. PCT/US2020/035343, mailed Sep. 7, 2020, 10 pages.
Balbach S. et al., Pharmaceutical evaluation of early development candidates "The 100 mg approach", International Journal of Pharmaceutics, 2004, vol. 275, pp. 1-12.
Caira M.R: "Crystalline Polymorphism of Organic Compounds", Design of Organic solids, Weber E et al"ED", Springer, 1998.
Shoushan, Zhang, "Practical Encyclopedia of New Technologies, New Process Flows, and Operational Skills in Pharmaceutical Production Workshops: Quality Control and Equipment Operation and Maintenance, vol. 1", China Medical Science and Technology Electronic Press, First edition, pp. 243-248, Oct. 31, 2005. (Provided with Machine Translation of OCR text.).
Singhal, D. et al., "Drug polymorphism and dosage form design: a practical perspective, Advanced Drug Delivery Reviews", 2004, vol. 56, pp. 33.

*Primary Examiner* — Samantha L Shterengarts
(74) *Attorney, Agent, or Firm* — McDonnell Boehnen Hulbert & Berghoff LLP

(57) ABSTRACT

This disclosure relates generally to crystalline polymorphs of a thiazolylpyrazole derivative, pharmaceutical compositions comprising them, and methods of using the crystalline polymorphs and their compositions.

27 Claims, 35 Drawing Sheets

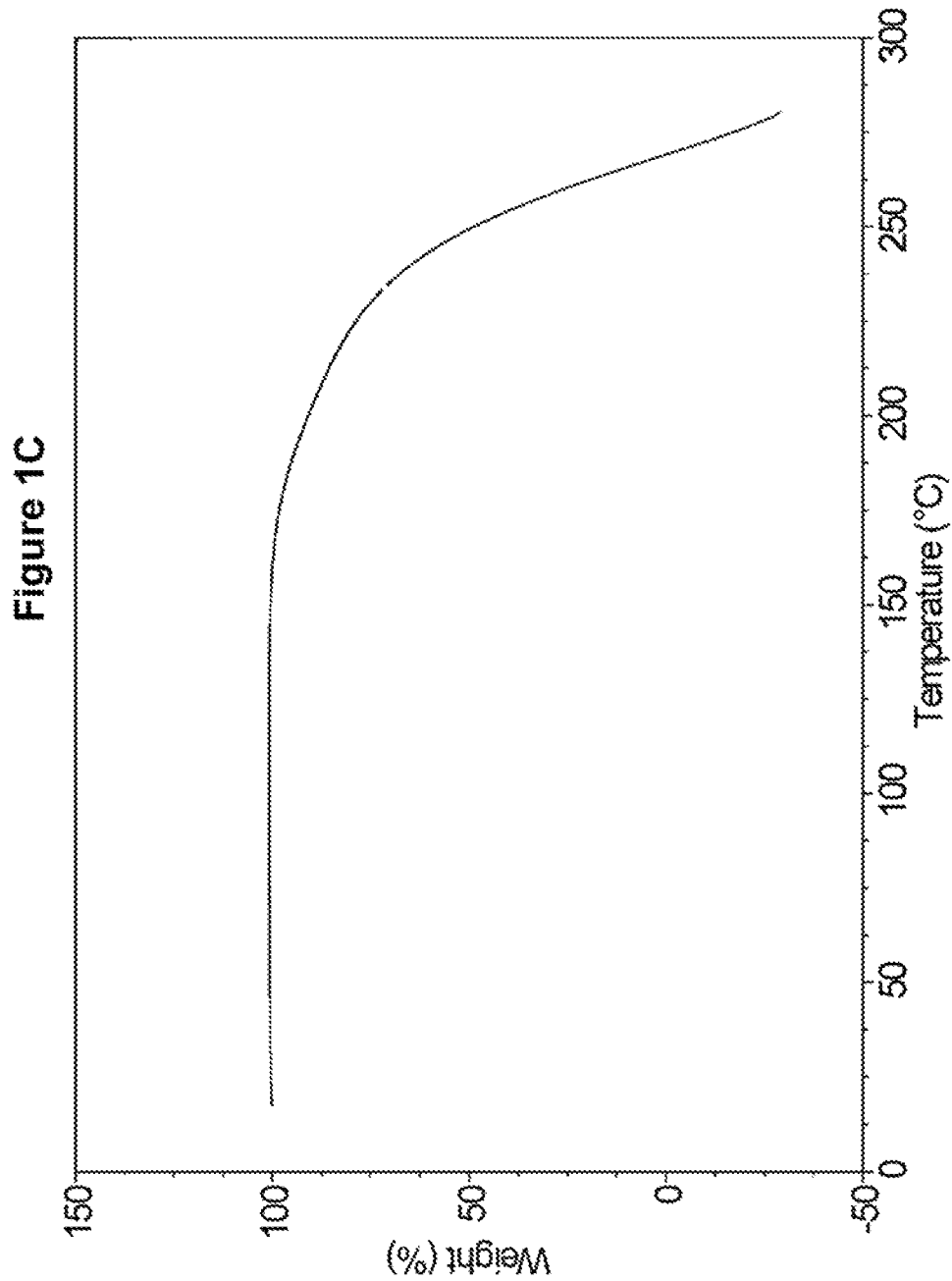

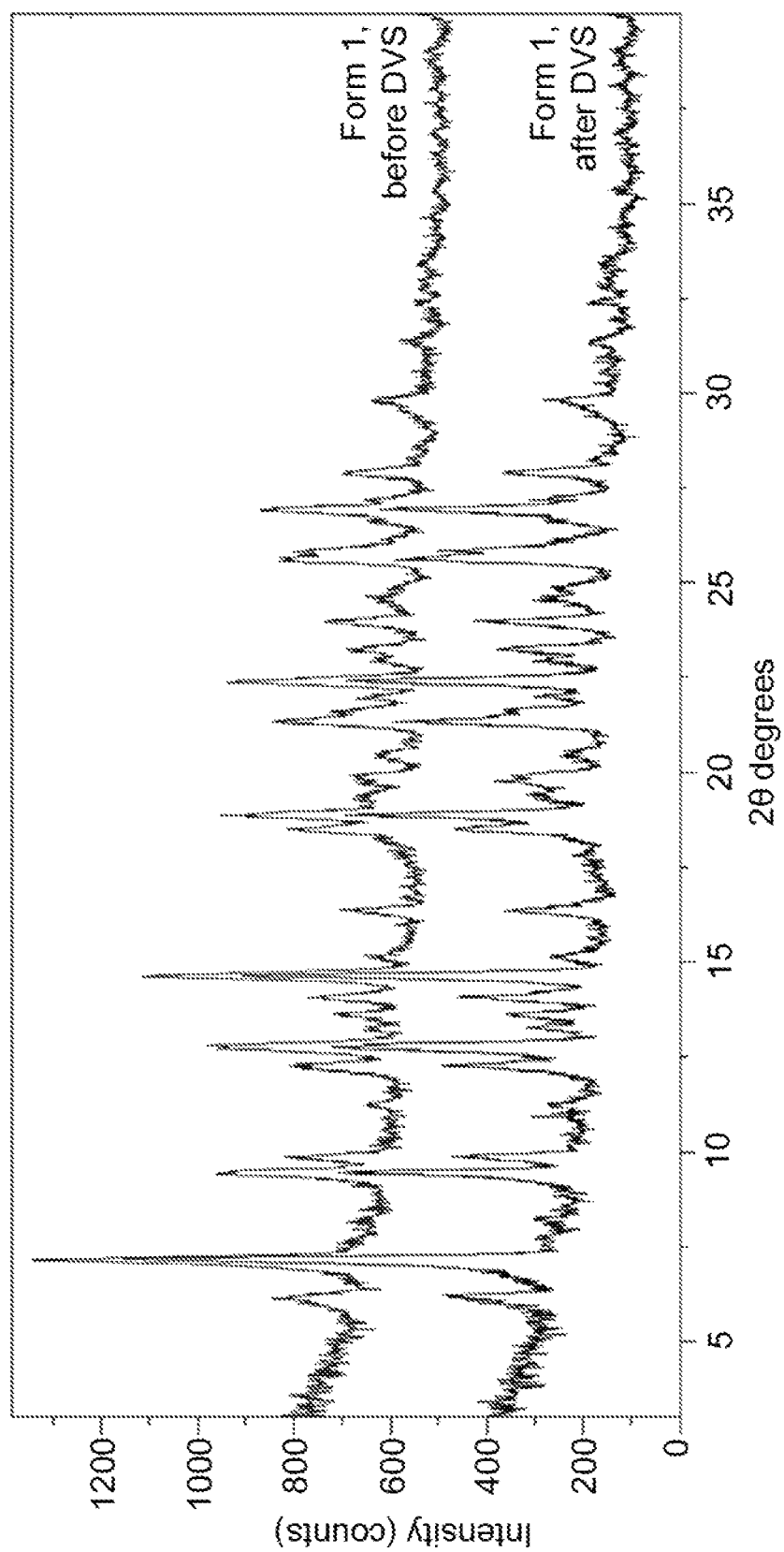

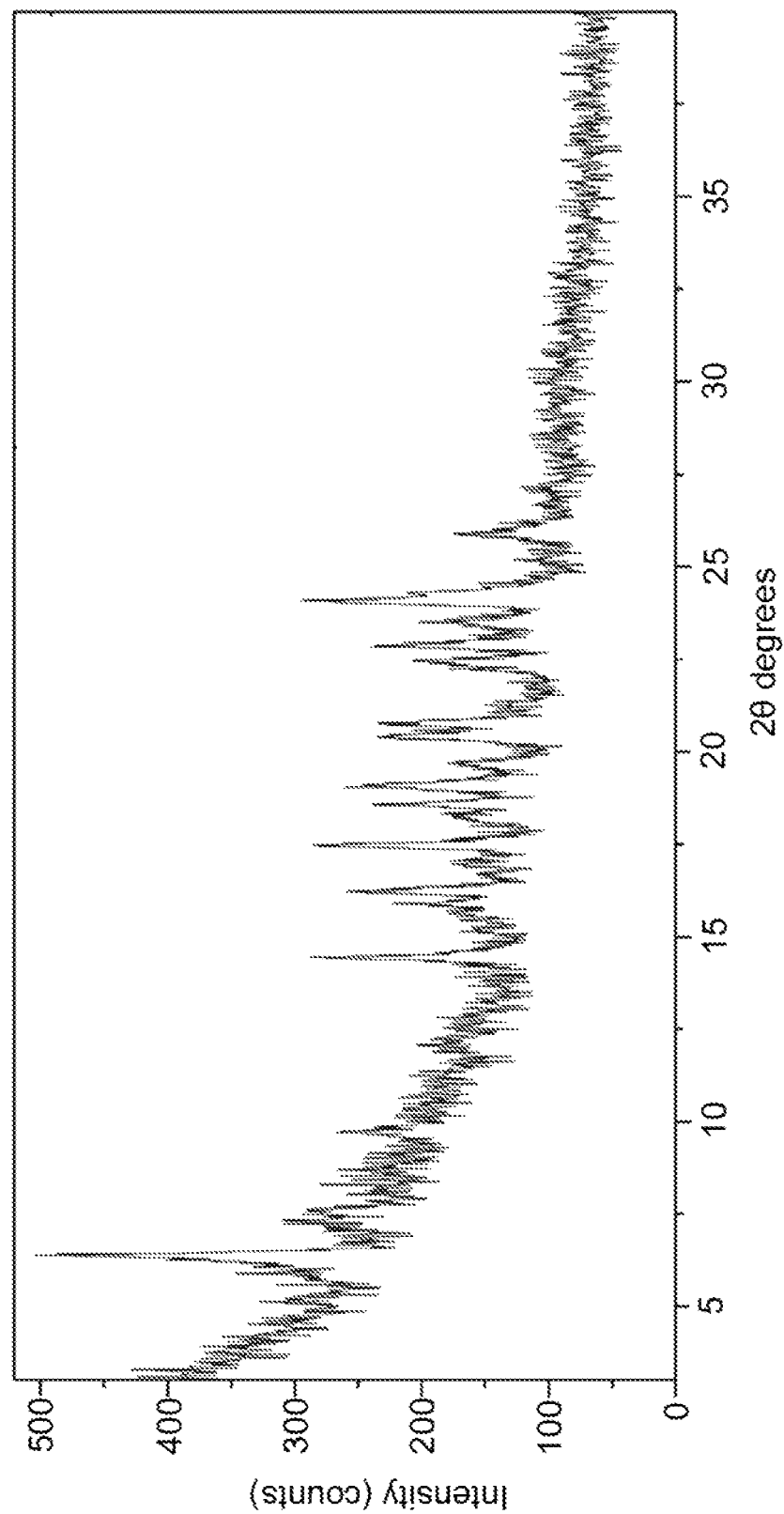

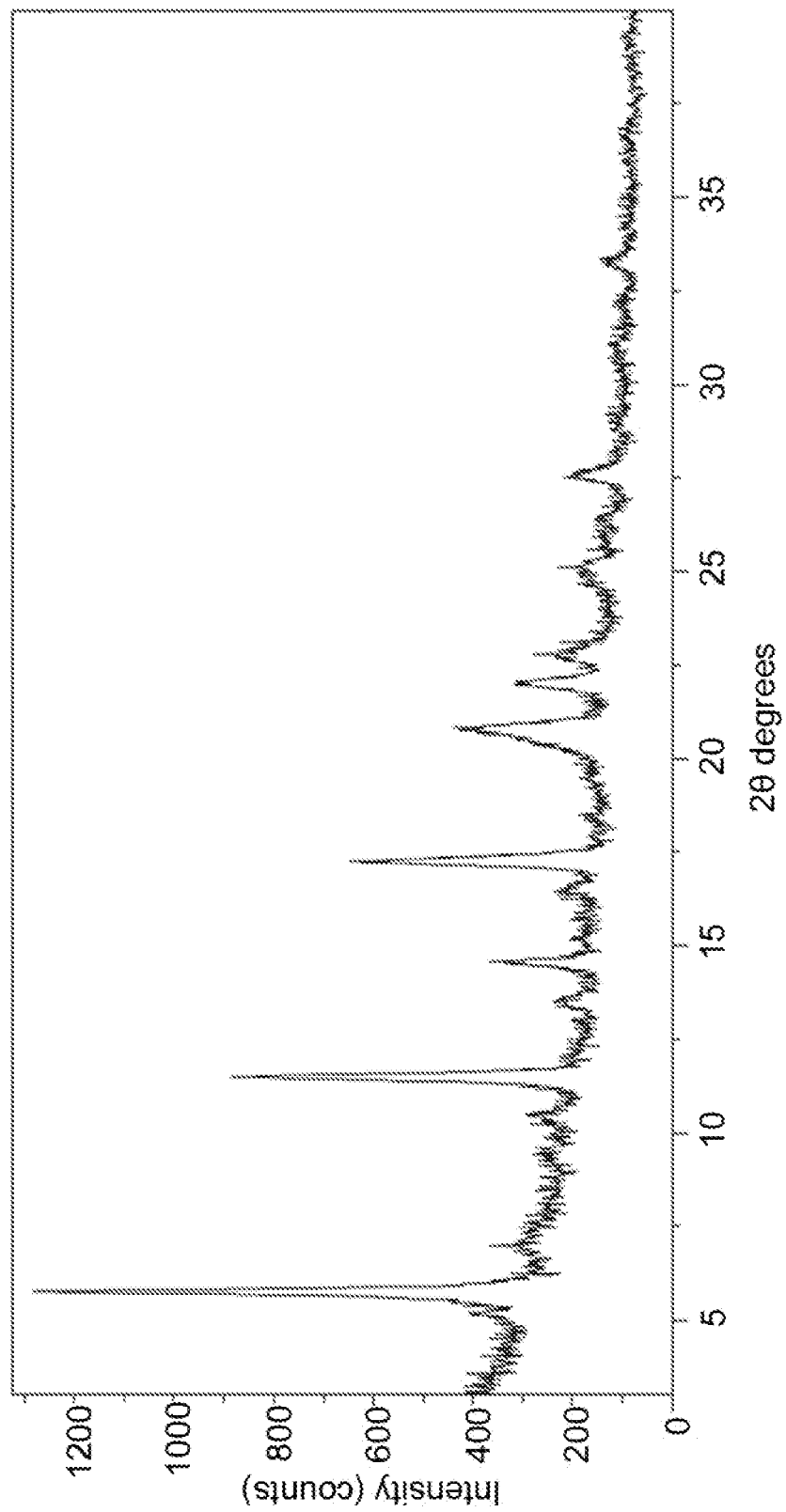

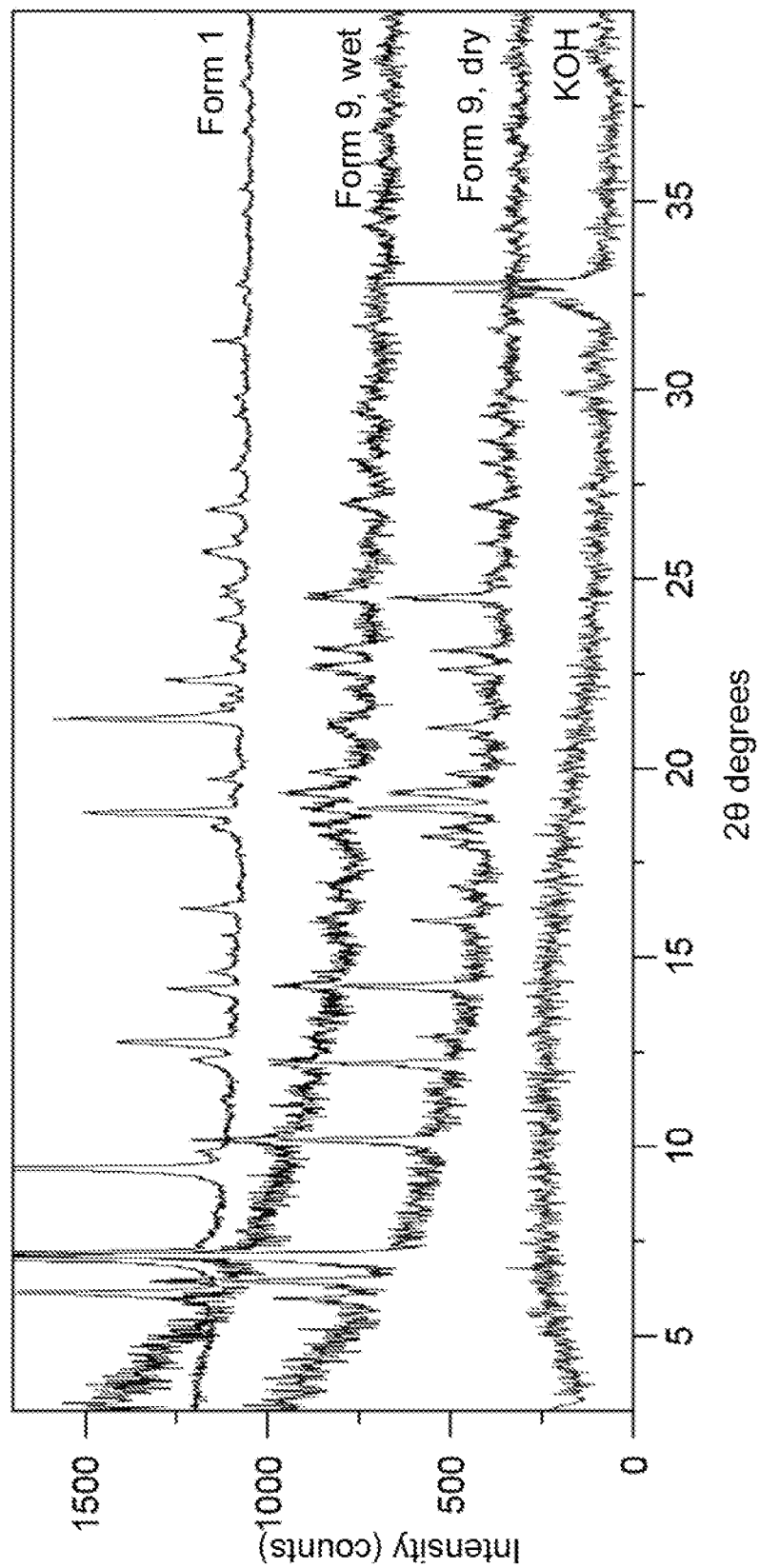

CRYSTALLINE POLYMORPHS OF A 1-THIAZOL-2-YL-PYRAZOLE-5-CARBOXYLIC ACID DERIVATIVE

CROSS-REFERENCE TO RELATED APPLICATIONS

This application is a U.S. National Stage entry of International Patent Application no. PCT/US2020/035343, filed May 29, 2020, which claims the benefit of priority of U.S. Provisional Patent Application No. 62/855,671, filed May 31, 2019, which is hereby incorporated herein by reference in its entirety.

BACKGROUND OF THE DISCLOSURE

Field of the Disclosure

This disclosure relates generally to crystalline polymorphs of a thiazolylpyrazole derivative, pharmaceutical compositions comprising them, and methods of using the crystalline polymorphs and their compositions.

Technical Background

Cancer, an uncontrolled proliferation of cells, is a multifactorial disease characterized by tumor formation, growth, and in some instances, metastasis. In the United States this year, over 1.5 million people will be diagnosed with cancer, and more than 500,000 people will die from cancer. Overall it is estimated that at least one in three people will develop some form of cancer during their lifetime. There are more than 200 different histopathological types of cancer, with breast, lung, colorectal, and prostate accounting for over half of all new cases in the U.S. Current cancer therapies vary depending upon the localization and stage of the cancer but generally include a combination of surgery, systemic therapy, radiation therapy, and chemotherapy. Despite the effort that has been devoted to the development of anti-cancer strategies, many of them remain inefficacious for specific cancers The uncontrolled cell proliferation that represents the essence of cancer involves not only deregulated control of cell proliferation but also corresponding adjustments of energy metabolism in order to fuel cell growth and division. The reprogramming of cell metabolism is emerging as an important molecular hallmark of cancer cells. Under aerobic conditions, normal cells process glucose, first to pyruvate via glycolysis in the cytosol and thereafter to carbon dioxide in the mitochondria; under anaerobic conditions, glycolysis is favored and relatively little pyruvate is dispatched to the oxygen-consuming mitochondria. When growth factors and nutrients are abundant, oncogenic signaling pathways direct enhanced metabolism leading to increased synthesis of macromolecules such as lipids, proteins and nucleic acids. The net effect is the support of cell growth and proliferation. During tumor formation, however, a harsh, anoxic, nutrient deprived environment exists that challenges the cell and its ability to maintain metabolic homeostasis. Cancer cells can reprogram their glucose metabolism, and thus their energy production, by limiting their energy metabolism largely to glycolysis, which was seen by early biochemists as primitive and inefficient. Despite these early beliefs, the metabolic signatures of cancer cells are not passive responses to damaged mitochondria, but result from oncogene-directed metabolic reprogramming required to support anabolic growth. Oncogene mutations that allow for increased and more efficient utilization of scarce nutrients present unique targets in treatment of cancer.

Particularly useful thiazolylpyrazole compounds, such as 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (identified herein as Compound 1), for treatment of cancer were disclosed in International Publications No. WO 2018/102452 and WO 2018/102453. These compounds are believed to be active against cancer cells by arresting the cell cycle at the G0/G1 phase, and thereby inducing apoptosis of a cancer cell. These compounds are also believed to inhibit glutathione synthesis in a cancer cell. Therefore, these thiazolylpyrazole compounds show promise for treatment of cancer.

Nevertheless, certain crystalline (morphological or polymorphic) forms of known compounds are important in drug development. For example, some polymorphic forms may exhibit enhanced thermodynamic stability, solubility, dissolution, etc. compared to other forms. As a result, some polymorphic forms may be more suitable than other polymorphic forms in the formulated pharmaceutical compositions.

Thus, there remains a need for improved forms of particularly useful anti-cancer compounds, and particularly improved forms of the thiazolylpyrazole compounds.

SUMMARY OF THE DISCLOSURE

One aspect of the disclosure provides crystalline polymorphs of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (identified herein as Compound 1), optionally in the form of a hydrate or solvate thereof.

Another aspect of the disclosure provides crystalline polymorphs of different salts of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid, optionally in the form of a hydrate or solvate thereof. In certain embodiments of this aspect, the salt is a potassium, sodium, magnesium, urea, L-arginine, or L-proline salt of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid.

Another aspect of the disclosure provides a salt, optionally the form of a hydrate or solvate thereof, selected from:
potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
sodium 4-(3-fluorophenyl)-1-(5-(isopropylthio)-4-(4-(trifluoromethyl)cyclohex-1-en-1-yl)thiazol-2-yl-3-methyl-1H-pyrazole-5-carboxylate;
magnesium 4-(3-fluorophenyl)-1-(5-(isopropylthio)-4-(4-(trifluoromethyl)cyclohex-1-en-1-yl)thiazol-2-yl-3-methyl-1H-pyrazole-5-carboxylate;
urea 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
L-arginine 4-(3-fluorophenyl)-1-(5-(isopropylthio)-4-(4-(trifluoromethyl)cyclohex-1-en-1-yl)thiazol-2-yl-3-methyl-1H-pyrazole-5-carboxylate; and
L-proline 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate.

In another aspect, the disclosure provides pharmaceutical compositions comprising a crystalline polymorph or a salt as described herein.

In another aspect, the disclosure provides a method for treating a hyperproliferative disorder such as cancer in a subject in need thereof. The method includes administering to the subject an effective amount of a crystalline polymorph or a salt as described herein.

In another aspect, the disclosure provides crystalline polymorph or a salt as described herein for use in treating hyperproliferative disorders such as cancer.

In another aspect, the disclosure provides the use of a crystalline polymorph or a salt as described herein for the preparation of a medicament for the treatment of a hyperproliferative disorder such as cancer.

In certain embodiments of the various aspects of the disclosure, the hyperproliferative disorder is a hematopoietic cancer. In certain alternative embodiments of the disclosure, the hyperproliferative disorder is a solid tumor.

In certain embodiments of the various aspects of the disclosure, the hyperproliferative disorder is a cancer (e.g., a solid tumor such as a colorectal cancer, a lung cancer or a pancreatic cancer) having a mutant KRAS gene, e.g., a heterozygous mutant KRAS gene.

Another aspect of the disclosure provides a method for inhibiting cell cycle progression in a cancer cell. The method includes contacting the cancer cell with an effective amount of a crystalline polymorph or a salt as described herein. In certain such embodiments, the cancer cell is a hematopoietic cancer cell. In other such embodiments, the cancer cell is a cancer cell of a solid tumor (e.g., a pancreatic cancer, a lung cancer, or a colorectal cancer). In certain such embodiments, the cancer cell has a heterozygous mutant KRAS gene. Cell cycle progression can be inhibited, for example, at the G0/G1 phase.

Another aspect of the disclosure provides a method for inducing apoptosis of a cancer cell. The method includes contacting the cancer cell with an effective amount of a crystalline polymorph or a salt as described herein. In certain such embodiments, the cancer cell is a hematopoietic cancer cell.

Another aspect of the disclosure provides a method for inducing cytotoxic effect of a cancer cell. The method includes contacting the cancer cell with an effective amount of a crystalline polymorph or a salt as described herein. In certain such embodiments, the cancer cell is a hematopoietic cancer cell. In other such embodiments, the cancer cell is a cancer cell of a solid tumor (e.g., a pancreatic cancer, a lung cancer, or a colorectal cancer). In certain such embodiments, the cancer cell has a heterozygous mutant KRAS gene.

Another aspect of the disclosure provides a method for inhibiting glutathione synthesis in a cancer cell. The method includes contacting the cancer cell with an effective amount of a crystalline polymorph or a salt as described herein. In certain such embodiments, the cancer cell is a hematopoietic cancer cell. In other such embodiments, the cancer cell is a cancer cell of a solid tumor (e.g., a pancreatic cancer, a lung cancer, or a colorectal cancer). In certain such embodiments, the cancer cell has a heterozygous mutant KRAS gene.

Other aspects and embodiments of the disclosure are evident in view of the detailed description provided herein.

BRIEF DESCRIPTION OF THE DRAWINGS

The accompanying drawings are included to provide a further understanding of the compositions and methods of the disclosure, and are incorporated in and constitute a part of this specification. The drawings illustrate one or more embodiment(s) of the disclosure and, together with the description, serve to explain the principles and operation of the disclosure.

FIGS. 1B and 1C show a differential scanning calorimetry (DSC) profile and a thermogravimetric analysis (TGA), respectively, for the crystalline polymorph Form 1.

FIG. 1E shows Form 1 before and after dynamic vapor sorption (DVS) measurements.

FIG. 3A shows a XRPD pattern for the crystalline polymorph Form 3 (Example 6).

FIG. 6A shows a XRPD pattern for the crystalline polymorph Form 6 (Example 10).

FIG. 9A shows a XRPD pattern for the crystalline polymorph Form 9 (Example 13).

DETAILED DESCRIPTION

Figure 1A:
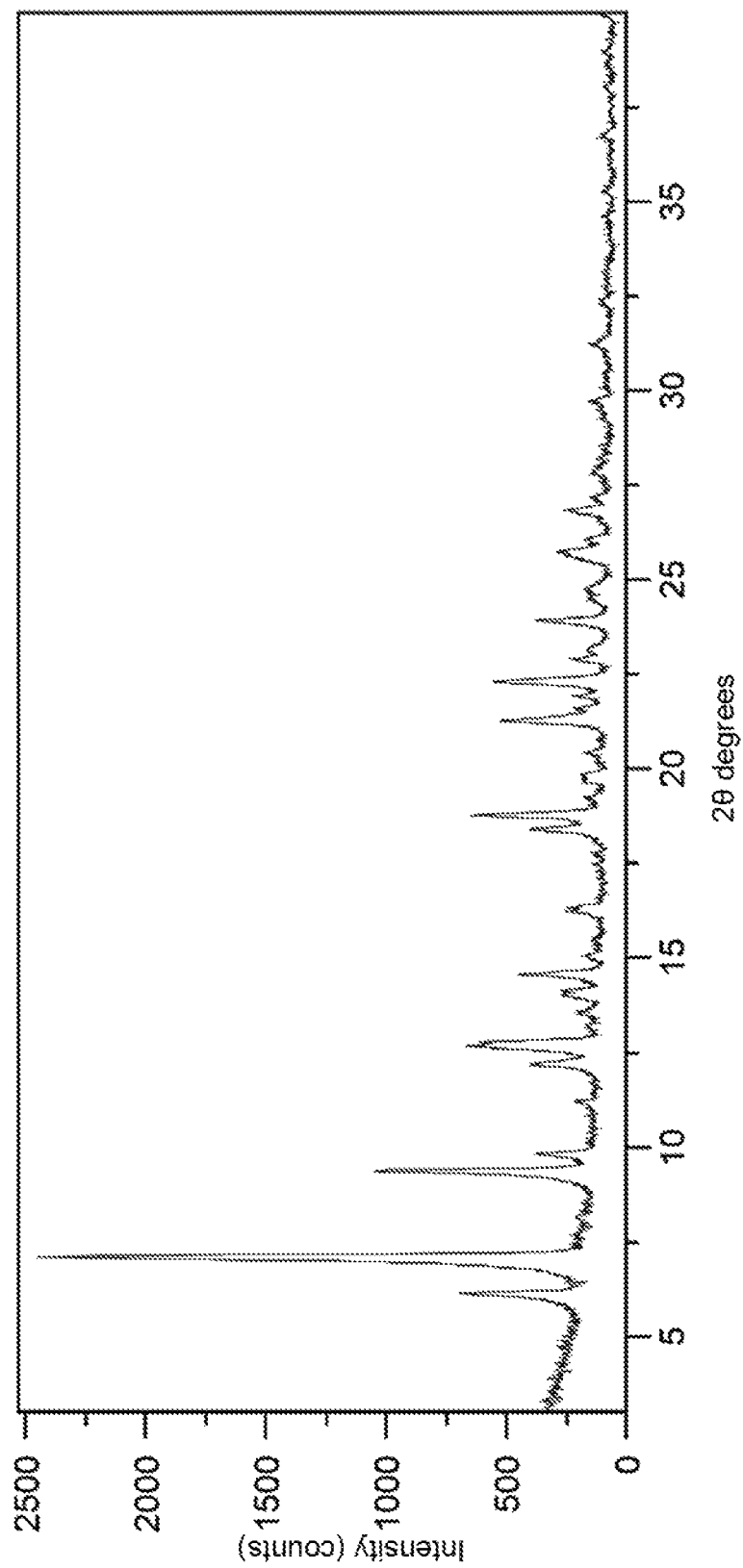
FIG. 1A shows an X-ray powder diffraction (XRPD) pattern for the crystalline polymorph Form 1 (Example 2).

The present inventors have found novel crystalline polymorphs useful for the treatment of cancer. Thus, one aspect of the disclosure provides novel crystalline polymorphs of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid, optionally in the form of a hydrate or solvate thereof.

The ability of a compound to exist in different crystal structures is known as polymorphism. As used herein "polymorph" refers to crystalline forms having the same chemical composition but different spatial arrangements of the molecules, atoms, and/or ions forming the crystal. While polymorphs have the same chemical composition, they differ in packing and geometrical arrangement, and may exhibit different physical properties such as melting point, shape, color, density, hardness, deformability, stability, dissolution, and the like. Polymorphs of a compound can be distinguished in a laboratory by X-ray diffraction spectroscopy, such as XRPD, and by other methods, such as infrared spectrometry (IR). Additionally, polymorphs of the same drug substance or active pharmaceutical ingredient can be administered by itself or formulated as a drug product (pharmaceutical composition) and are well known in the pharmaceutical art to affect, for example, the solubility, stability, flowability, tractability and compressibility of drug substances and the safety and efficacy of drug products (see Brittain, H. (Ed.). (1999). *Polymorphism in Pharmaceutical Solids*. Boca Raton: CRC Press; and Hilfiker, Rolf (ed.). (2006) *Polymorphism in the Pharmaceutical Industry*. Weinheim, Germany: Wiley-VCH).

In certain embodiments the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (i.e., as the free acid) referred to herein as "Form 1". In certain embodiments, the Form 1 crystalline polymorph is an anhydrate/ansolvate (i.e., does not include solvent or water in its crystalline structure). Such crystalline polymorph can be characterized in that it provides a XRPD pattern comprising four or more (e.g., five or more) peaks selected from: 6.1, 7.1, 9.4, 12.7, 18.8, 21.3 and 22.3 (2θ±0.1 degrees). In certain embodiments, the crystalline polymorph is characterized in that it provides a XRPD pattern comprising six or more (e.g., each of the) peaks selected from: 6.1, 7.1, 9.4, 12.7, 18.8, 21.3 and 22.3 (2θ±0.1 degrees). In certain embodiments, the crystalline polymorph of the disclosure is characterized in that it provides a XRPD pattern in accordance with that shown in FIG. 1A.

In certain embodiments, the crystalline polymorph of the disclosure referred to herein as Form 1 is characterized in that it provides a DSC thermogram having an endothermic peak at 123±2° C. In certain embodiments, the Form 1 crystalline polymorph of the disclosure is characterized in that it provides a DSC thermogram in accordance with that shown in FIG. 1B.

In certain embodiments, the crystalline polymorph of the disclosure referred to herein as Form 1 is characterized in that it provides a Fourier-transform infrared spectroscopy (FTIR) spectrum comprising six or more (e.g., seven or more, or eight or more, or nine or more) peaks selected from: 2930 (broad)±2 cm$^{-1}$, 1709±2 cm$^{-1}$, 1539±2 cm$^{-1}$, 1359±2 cm$^{-1}$, 1238±2 cm$^{-1}$, 1165±2 cm$^{-1}$, 1112±2 cm$^{-1}$, 987±2 cm$^{-1}$, 875±2 cm$^{-1}$, 772.50±2 cm$^{-1}$, and 690±2 cm$^{-1}$. In certain embodiments, the crystalline polymorph is characterized in that it provides an FTIR spectrum comprising ten or more peaks selected from: 2930 (broad)±2 cm$^{-1}$, 1709±2 cm$^{-1}$, 1539±2 cm$^1$, 1359±2 cm$^{-1}$, 1238±2 cm$^{-1}$, 1165±2 cm$^{-1}$, 1112±2 cm$^{-1}$, 987±2 cm$^1$, 875±2 cm$^{-1}$, 772.50±2 cm$^{-1}$, and 690±2 cm$^{-1}$. In certain embodiments, the crystalline polymorph is characterized in that it provides an FTIR spectrum comprising each of the peaks: 1709±2 cm$^{-1}$, 1539±2 cm$^{-1}$, 1359±2 cm$^1$, 1238±2 cm$^{-1}$, 1165±2 cm$^{-1}$, 1112±2 cm$^{-1}$, 987±2 cm$^1$, 875±2 cm$^{-1}$, 772.50±2 cm$^{-1}$, and 690±2 cm$^{-1}$. In certain embodiments, the crystalline polymorph of the disclosure is characterized in that it provides an FTIR spectrum in accordance with that shown in FIG. 1D.

In certain embodiments the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid referred to herein as "Form 2". In certain embodiments, the Form 2 crystalline polymorph is an anhydrate/ansolvate Such crystalline polymorph can be characterized in that it provides a XRPD pattern comprising four or more (e.g., five or more) peaks selected from: 6.2, 6.6, 7.5, 10.9, 12.4, and 13.3 (2θ±0.1 degrees). In certain embodiments, the crystalline polymorph is characterized in that it provides a XRPD pattern comprising each of the peaks: 6.2, 6.6, 7.5, 10.9, 12.4, and 13.3 (2θ±0.1 degrees). In certain embodiments, the crystalline polymorph of the disclosure is characterized in that it provides a XRPD pattern in accordance with that shown in FIG. 2.

In certain embodiments the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid referred to herein as "Form 5". In certain embodiments, the Form 5 crystalline polymorph is an anhydrate/ansolvate Such crystalline polymorph is characterized in that it provides a XRPD pattern comprising four or more (e.g., five or more) peaks selected from: 6.4, 7.1, 17.7, 18.8, 19.3, and 22.5 (2θ±0.1 degrees). In certain embodiments, the crystalline polymorph is characterized in that it provides a XRPD pattern comprising six or more (e.g., each of the) peaks selected from: 6.4, 7.1, 17.7, 18.8, 19.3, and 22.5 (2θ±0.1 degrees). In certain embodiments, the crystalline polymorph of the disclosure is characterized in that it provides a XRPD pattern in accordance with that shown in FIG. 5A.

In certain embodiments, the crystalline polymorph of the disclosure referred to herein as Form 5 is characterized in that it provides a DSC thermogram having an endothermic peak at 142±2° C. In certain embodiments, the crystalline polymorph of the disclosure is characterized in that it provides a DSC thermogram in accordance with that shown in FIG. 5B.

In certain embodiments the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid referred to herein as "Form 8". In certain embodiments, the Form 8 crystalline polymorph is an anhydrate/ansolvate. Such crystalline polymorph is characterized in that it provides a XRPD pattern comprising four or more (e.g., five or more) peaks selected from: 6.4, 9.1, 14.3, 16.6, 18.4, 20.1, and 21.9 (2θ±0.1 degrees). In certain embodiments, the crystalline polymorph is characterized in that it provides a XRPD pattern comprising each of the peaks: 6.4, 9.1, 14.3, 16.6, 18.4, 20.1, and 21.9 (2θ±0.1 degrees). In certain embodiments, the crystalline polymorph of the disclosure is characterized in that it provides a XRPD pattern in accordance with that shown in FIG. 8.

The disclosure also provides novel crystalline polymorphs of a hydrate or a solvate of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (i.e., as the free acid).

Thus, in certain embodiments, the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (e.g., as a hydrate or solvate) referred to herein as "Form 3". Such crystalline polymorph is characterized in that it provides a XRPD pattern comprising four or more (e.g., five or more) peaks selected from: 6.4, 14.4, 16.2, 17.5, 19.1, 22.8, and 24.0 (2θ±0.1 degrees). In certain embodiments, the crystalline polymorph is characterized in that it provides a XRPD pattern comprising six or more (e.g., each of the) peaks: 6.4, 14.4, 16.2, 17.5, 19.1, 22.8, and 24.0 (2θ±0.1 degrees). In certain embodiments, the crystalline polymorph of the disclosure is characterized in that it provides a XRPD pattern in accordance with that shown in FIG. 3A.

In certain embodiments, the crystalline polymorph of the disclosure referred to herein as Form 3 is characterized in that it provides a DSC thermogram having endothermic peaks at 91±2° C. and 118±2° C. In certain embodiments, the crystalline polymorph of the disclosure is characterized in that it provides a DSC thermogram in accordance with that shown in FIG. 3B.

In certain embodiments, the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (e.g., as a hydrate or solvate) referred to herein as "Form 4". Such crystalline polymorph is characterized in that it provides a XRPD pattern comprising four or more (e.g., five or more) peaks selected from: 9.9, 14.9, 19.4, 21.4, 23.5, and 24.1 (2θ±0.1 degrees). In certain embodiments, the crystalline polymorph is characterized in that it provides a XRPD pattern comprising each of the peaks: 9.9, 14.9, 19.4, 21.4, 23.5, and 24.1 (2θ±0.1 degrees). In certain embodiments, the crystalline polymorph of the disclosure is characterized in that it provides a XRPD pattern in accordance with that shown in FIG. 4A.

In certain embodiments, the crystalline polymorph of the disclosure referred to herein as Form 4 is characterized in that it provides a DSC thermogram having endothermic peaks at 49±2° C. and 73±2° C. In certain embodiments, the crystalline polymorph of the disclosure is characterized in that it provides a DSC thermogram in accordance with that shown in FIG. 4B.

In certain embodiments, the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (e.g., as a hydrate or solvate) referred to herein as "Form 6". Such crystalline polymorph is characterized in that it provides a XRPD pattern comprising four or more (e.g., five or more) peaks selected from: 5.8, 11.5, 14.5, 17.3, 20.8, and 22.0 (2θ±0.1 degrees). In certain embodiments, the crystalline polymorph is characterized in that it provides a XRPD pattern comprising each of the peaks: 5.8, 11.5, 14.5, 17.3, 20.8, and 22.0 (2θ±0.1 degrees). In certain embodiments, the crystalline polymorph of the disclosure is characterized in that it provides a XRPD pattern in accordance with that shown in FIG. 6A.

In certain embodiments, the crystalline polymorph of the disclosure referred to herein as Form 6 is characterized in that it provides a DSC thermogram having endothermic peaks at 64±2° C. and 120±2° C. In certain embodiments, the crystalline polymorph of the disclosure is characterized in that it provides a DSC thermogram in accordance with that shown in FIG. 6B.

In certain embodiments, the crystalline polymorph of the disclosure is a novel crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (e.g., as a hydrate or solvate) referred to herein as "Form 7". Such crystalline polymorph is characterized in that it provides a XRPD pattern comprising four or more (e.g., five or more) peaks selected from: 6.7, 7.0, 11.5, 13.1, 14.4, 17.2 and 22.1 (2θ±0.1 degrees). In certain embodiments, the crystalline polymorph is characterized in that it provides a XRPD pattern comprising each of the peaks: 6.7, 7.0, 11.5, 13.1, 14.4, 17.2 and 22.1 (2θ±0.1 degrees). In certain embodiments, the crystalline polymorph of the disclosure is characterized in that it provides a XRPD pattern in accordance with that shown in FIG. 7A.

In certain embodiments, the crystalline polymorph of the disclosure referred to herein as Form 7 is characterized in that it provides a DSC thermogram having endothermic peaks at 58±2° C. and 108±2° C. In certain embodiments, the crystalline polymorph of the disclosure is characterized in that it provides a DSC thermogram in accordance with that shown in FIG. 7B.

The disclosure also provides novel crystalline polymorphs of different salts of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid, optionally in the form of a hydrate or solvate thereof. For example, in certain embodiments, the disclosure provides crystalline polymorphs of potassium, sodium, magnesium, urea, L-arginine, or L-proline salts.

The crystalline polymorph of the disclosure, in certain embodiments, is a crystalline polymorph of potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

In certain embodiments, the crystalline polymorph of the disclosure is potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (e.g., as a hydrate or solvate) referred to herein as "Form 9". Such crystalline polymorph is characterized in that it provides a XRPD pattern comprising four or more (e.g., five or more) peaks selected from: 6.4, 7.1, 10.2, 12.2, 14.2, 19.0, 19.4, and 24.5 (2θ±0.1 degrees). In certain embodiments, the crystalline polymorph is characterized in that it provides a XRPD pattern comprising each of the peaks: 6.4, 7.1, 10.2, 12.2, 14.2, 19.0, 19.4, and 24.5 (2θ±0.1 degrees). In certain embodiments, the crystalline polymorph of the disclosure is characterized in that it provides a XRPD pattern in accordance with that shown in FIG. 9A.

In certain embodiments, the crystalline polymorph of the disclosure referred to herein as Form 9 is characterized in that it provides a DSC thermogram having an endothermic peak at 113±2° C. In certain embodiments, the crystalline polymorph of the disclosure is characterized in that it provides a DSC thermogram in accordance with that shown in FIG. 9B.

In certain embodiments, the crystalline polymorph of the disclosure is potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (e.g., as a hydrate or solvate) referred to herein as "Form 10". Such crystalline polymorph is characterized in that it provides a XRPD pattern comprising four or more (e.g., five or more) peaks selected from: 5.6, 5.8, 7.4, 9.5, 12.8, 15.5, and 19.5 (2θ±0.1 degrees). In certain embodiments, the crystalline polymorph is characterized in that it provides a XRPD pattern comprising each of the peaks: 5.6, 5.8, 7.4, 9.5, 12.8, 15.5, and 19.5 (2θ±0.1 degrees). In certain embodiments, the crystalline polymorph of the disclosure is characterized in that it provides a XRPD pattern in accordance with that shown in FIG. 10A.

In certain embodiments, the crystalline polymorph of the disclosure referred to herein as Form 10 is characterized in that it provides a DSC thermogram having endothermic peaks at 62±2° C. and 144±2° C. In certain embodiments, the crystalline polymorph of the disclosure is characterized in that it provides a DSC thermogram in accordance with that shown in FIG. 10B.

The crystalline polymorph of the disclosure, in certain embodiments, is a crystalline polymorph of sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

In certain embodiments, the crystalline polymorph of the disclosure is sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (e.g., as a hydrate or solvate) referred to herein as "Form 11". Such crystalline polymorph is characterized in that it provides a XRPD pattern comprising four or more (e.g., five or more) peaks selected from: 7.0, 10.4, 12.2, 13.1, 14.0, 18.8, and 24.5 (2θ±0.1 degrees). In certain embodiments, the crystalline polymorph is characterized in that it provides a XRPD pattern comprising each of the peaks: 7.0, 10.4, 12.2, 13.1, 14.0, 18.8, and 24.5 (2θ±0.1 degrees). In certain embodiments, the crystalline polymorph of the disclosure is characterized in that it provides a XRPD pattern in accordance with that shown in FIG. 11A.

In certain embodiments, the crystalline polymorph of the disclosure referred to herein as Form 11 is characterized in that it provides a DSC thermogram having an endothermic peak at 76±2° C. (e.g., broad). In certain embodiments, the crystalline polymorph of the disclosure is characterized in that it provides a DSC thermogram in accordance with that shown in FIG. 11B.

In certain embodiments, the crystalline polymorph of the disclosure is sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate referred to herein as "Form 12". In certain embodiments, the Form 12 crystalline polymorph is an anhydrate/ansolvate. Such crystalline polymorph is characterized in that it provides a XRPD pattern comprising four or more (e.g., five or more) peaks selected from: 3.8, 7.5, 13.0, 16.2, 17.0, 17.8, 20.0, 22.7, and 23.7 (2θ±0.1 degrees). In certain embodiments, the crystalline polymorph is characterized in that it provides a XRPD pattern comprising six or more, or seven or more, or each of the peaks: 3.8, 7.5, 13.0, 16.2, 17.0, 17.8, 20.0, 22.7, and 23.7 (2θ±0.1 degrees). In certain embodiments, the crystalline polymorph of the disclosure is characterized in that it provides a XRPD pattern in accordance with that shown in FIG. 12A.

In certain embodiments, the crystalline polymorph of the disclosure referred to herein as Form 12 is characterized in that it provides a DSC thermogram having an endothermic peak at 153±2° C. In certain embodiments, the crystalline polymorph of the disclosure is characterized in that it provides a DSC thermogram in accordance with that shown in FIG. 12B.

The crystalline polymorph of the disclosure, in certain embodiments, is a crystalline polymorph of L-arginine 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof. For example, in certain embodiments, the crystalline polymorph of L-arginine 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate referred to herein as "Form 13". In certain embodiments, the Form 13 crystalline polymorph is an anhydrate/ansolvate. Such crystalline polymorph is characterized in that it provides a XRPD pattern comprising four or more (e.g., five or more) peaks selected from: 10.3, 16.6, 18.7, 20.7, 21.3, 25.0, and 28.2 (2θ±0.1 degrees). In certain embodiments, the crystalline polymorph is characterized in that it provides a XRPD pattern comprising six or more, or each of the, peaks: 10.3, 16.6, 18.7, 20.7, 21.3, 25.0, and 28.2 (2θ±0.1 degrees). In certain embodiments, the crystalline polymorph of the disclosure is characterized in that it provides a XRPD pattern in accordance with that shown in FIG. 13A.

In certain embodiments, the crystalline polymorph of the disclosure referred to herein as Form 13 is characterized in that it provides a DSC thermogram having an endothermic peak at 231±2° C. In certain embodiments, the crystalline polymorph of the disclosure is characterized in that it provides a DSC thermogram in accordance with that shown in FIG. 13B.

The crystalline polymorph of the disclosure, in certain embodiments, is a crystalline polymorph of magnesium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof. For example, in certain embodiments, the crystalline polymorph of magnesium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (e.g., as a hydrate or solvate) referred to herein as "Form 14". Such crystalline polymorph is characterized in that it provides a XRPD pattern comprising four or more (e.g., five or more) peaks selected from: 5.4, 15.8, 16.8, 18.7, 25.1, and 38.2 (2θ±0.1 degrees). In certain embodiments, the crystalline polymorph is characterized in that it provides a XRPD pattern comprising six or more, or each of the, peaks: 5.4, 15.8, 16.8, 18.7, 25.1, and 38.2 (2θ±0.1 degrees). In certain embodiments, the crystalline polymorph of the disclosure is characterized in that it provides a XRPD pattern in accordance with that shown in FIG. 14A.

In certain embodiments, the crystalline polymorph of the disclosure referred to herein as Form 14 is characterized in that it provides a DSC thermogram having endothermic peaks at 105±2° C. and 137±2° C. In certain embodiments, the crystalline polymorph of the disclosure is characterized in that it provides a DSC thermogram in accordance with that shown in FIG. 14B.

The crystalline polymorph of the disclosure, in certain embodiments, is a crystalline polymorph of urea 4-(3-fluorophenyl)-1-(5-(isopropylthio)-4-(4-(trifluoromethyl) cyclohex-1-en-1-yl)thiazol-2-yl)-3-methyl-1H-pyrazole-5-carboxylate, optionally the form of a hydrate or solvate thereof. For example, in certain embodiments, the crystalline polymorph of urea 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate referred to herein as "Form 15". In certain embodiments, the Form 1 crystalline polymorph is an anhydrate/ansolvate Such crystalline polymorph is characterized in that it provides a XRPD pattern comprising four or more (e.g., five or more) peaks selected from: 5.7, 9.8, 16.5, 17.3, 17.8, 20.0, 21.1, 23.5 and 26.1 (2θ±0.1 degrees). In certain embodiments, the crystalline polymorph is characterized in that it provides a XRPD pattern comprising six or more, or seven or more, or each of the, peaks: 5.7, 9.8, 16.5, 17.3, 17.8, 20.0, 21.1, 23.5 and 26.1 (2θ±0.1 degrees). In certain embodiments, the crystalline polymorph of the disclosure is characterized in that it provides a XRPD pattern in accordance with that shown in FIG. 15A.

In certain embodiments, the crystalline polymorph of the disclosure referred to herein as Form 15 is characterized in that it provides a DSC thermogram having an endothermic peak at 136±2° C. In certain embodiments, the crystalline polymorph of the disclosure is characterized in that it provides a DSC thermogram in accordance with that shown in FIG. 15B.

The crystalline polymorph of the disclosure, in certain embodiments, is a crystalline polymorph of L-proline 4-(3-fluorophenyl)-1-(5-(isopropylthio)-4-(4-(trifluoromethyl) cyclohex-1-en-1-yl)thiazol-2-yl)-3-methyl-1H-pyrazole-5-carboxylate, optionally the form of a hydrate or solvate thereof. For example, in certain embodiments, the crystalline polymorph of L-proline 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate (e.g., as a hydrate or solvate) referred to herein as "Form 16". Such crystalline polymorph is characterized in that it provides a XRPD pattern comprising four or more (e.g., five or more) peaks selected from: 7.7, 7.9, 11.9, 15.9, 17.4, 19.7, and 21.4 (2θ±0.1 degrees). In certain embodiments, the crystalline polymorph is characterized in that it provides a XRPD pattern comprising six or more, or each of the, peaks: 7.7, 7.9, 11.9, 15.9, 17.4, 19.7, and 21.4 (2θ±0.1 degrees). In certain embodiments, the crystalline polymorph of the disclosure is characterized in that it provides a XRPD pattern in accordance with that shown in FIG. 16A.

In certain embodiments, the crystalline polymorph of the disclosure referred to herein as Form 16 is characterized in that it provides a DSC thermogram having an endothermic peak at 168±2° C. In certain embodiments, the crystalline polymorph of the disclosure is characterized in that it provides a DSC thermogram in accordance with that shown in FIG. 16B.

Another aspect of the disclosure provides a salt, optionally the form of a hydrate or solvate thereof, selected from:
potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
magnesium 4-(3-fluorophenyl)-1-(5-(isopropylthio)-4-(4-(trifluoromethyl)cyclohex-1-en-1-yl)thiazol-2-yl-3-methyl-1H-pyrazole-5-carboxylate;
urea 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
L-arginine 4-(3-fluorophenyl)-1-(5-(isopropylthio)-4-(4-(trifluoromethyl)cyclohex-1-en-1-yl)thiazol-2-yl-3-methyl-1H-pyrazole-5-carboxylate; and
L-proline 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate.

In certain embodiments, potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate is in the form of a hydrate or solvate thereof. In certain embodiments, sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate is in the form of a hydrate or solvate thereof. In certain embodiments, magnesium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate is in the form of a hydrate or solvate thereof. In certain embodiments, L-proline 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate is in the form of a hydrate or solvate thereof.

Therapeutic Methods of the Disclosure

As noted above, mutations that allow for increased and more efficient utilization of scarce nutrients are favored during tumor formation. Oncogenic Ras stimulates both glucose uptake via enhanced expression of GLUT1, and utilization of glucose by anabolic pathways and conversion into glutathione, a key cellular antioxidant. Ras also regulates glutamine metabolism, specifically directing glucose and glutamine carbon into pathways that support biosynthesis, redox homeostasis and ultimately cell survival and growth. In addition to these effects on cellular metabolism, Ras has also been described to have effects on progression of the cell along the cell cycle. Specifically, Ras has been implicated as having a role in the transit across the restriction point in early G1 and again in G2. Ras activity at the G1 restriction point is particularly important as this event is the key integration point for growth factor signaling that commits the cell to further division or entry into the G0 or quiescent phase. Ras coordinates growth factor signaling to regulate levels of cyclins, cyclin dependent kinases and antagonistic cyclin dependent kinase inhibitors. Ras-related oncogenes, KRAS (also known as k-Ras or V-Ki-ras2 Kirsten rat sarcoma viral oncogene homolog) in particular, have also been shown to have direct effects on cellular metabolism. The outcome is a global rewiring of the metabolic circuits. KRAS has been noted to have pleiotropic effects on glucose utilization, glutathione synthesis, and redox balance and glutamine metabolism. Glutathione, an ubiquitous intracellular peptide, has diverse functions including modulation of cell proliferation, detoxification, and antioxidant defense. Increased glutathione levels have been associated with an early proliferative response (for example, stimulating cells to shift from G0 to G1 phase of the cell cycle), and are essential for the cell to enter the S phase. Glutathione has also been implicated in the regulation of cell death, likely modulating both apoptosis and necrosis. In addition, increased levels of glutathione have been reported in many tumors and have been implicated to confer drug and/or radiation resistance and impede chemotherapy. Thus, inhibitors of glutathione synthesis present unique chemotherapeutic targets.

Without intending to be bound by theory, the inventors believe that the crystalline polymorphs or salts described herein are active against cancer cells by arresting the cell cycle at the G0/G1 phase. Accordingly, as suggested above, the crystalline polymorphs or salts described herein can be employed in a variety of methods and uses. For example, in certain embodiments of the disclosure, a method for treating a hyperproliferative disorder in a subject in need thereof includes administering to the subject an effective amount of a crystalline polymorph or a salt as described herein. In other embodiments of the disclosure, a crystalline polymorph or a salt as described herein is provided for use in the treatment of hyperproliferative disorder. Other embodiments of the disclosure provide a crystalline polymorph or a salt as described herein for the preparation of a medicament for the treatment of a hyperproliferative disorder. In each of these embodiments, the hyperproliferative disorder can be, for example, a cancer.

The inventors have determined that, in certain embodiments, the presently described crystalline polymorphs or salts inhibit the progression of the cell cycle in cancer cells. Accordingly, another embodiment of the disclosure provides a method for inhibiting cell cycle progression in a cancer cell, the method comprising contacting the cancer cell with an effective amount of a crystalline polymorph or a salt as described herein. In certain such embodiments, the cell cycle progression is inhibited at the G0/G1 phase.

Inhibiting cell cycle progression at the G0/G1 phase can in certain embodiments induce apoptosis of a cancer cell. Accordingly, another embodiment of the disclosure provides a method for inducing apoptosis in a cancer cell, such as a hematopoietic cancer cell. The method includes contacting the cancer cell with an effective amount of a crystalline polymorph or a salt as described herein. However, in other embodiments, for example, in certain solid tumors, apoptosis may not be necessary for there to be an important therapeutic effect.

The inventors have determined that the crystalline polymorphs or salts described herein can, in certain embodiments, induce a cytotoxic effect on a cancer cell (e.g., through the apoptotic mechanism described above, or through an alternative mechanism). Accordingly, another embodiment of the disclosure provides a method for inducing a cytotoxic effect on a cancer cell. The method includes contacting the cancer cell with an effective amount of a crystalline polymorph or a salt as described herein.

The inventors have determined that the crystalline polymorphs or salts described herein can, in certain embodiments, inhibit glutathione synthesis in a cancer cell. Accordingly, another embodiment of the disclosure provides a method for inhibiting glutathione synthesis in a cancer cell. The method includes contacting the cancer cell with an effective amount of a crystalline polymorph or a salt as described herein.

The methods, crystalline polymorphs or salts and uses described herein can be employed with respect to a variety of different cancers or with respect to cells of a variety of different types of cancer. For example, in certain embodiments of the methods, crystalline polymorphs or salts and uses as otherwise described herein, the cancer is a hematopoietic cancer. In other embodiments, the cancer is a solid tumor.

In certain embodiments of the methods, crystalline polymorphs or salts and uses as otherwise described herein, the cancer is a lymphoma (e.g., Burkitt's lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)). In other such embodiments, the cancer is a leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukaemia, acute biphenotypic leukaemia, and polycythemia vera), acute and chronic T-cell and B-cell leukemia). In other such embodiments, the cancer is a plasma cell neoplasm (e.g., multiple myeloma).

However, the person of ordinary skill in the art will appreciate from the disclosure provided herein that the methods, crystalline polymorphs or salts and uses described herein can be employed with a variety of other types of cancer. For example, in certain embodiments of the methods, crystalline polymorphs or salts and uses as otherwise described herein, the cancer is selected from appendix cancer, bone cancer (e.g., Ewing sarcoma, osteosarcoma and malignant fibrous histiocytoma), bronchial tumors, carcinoma of unknown primary, chronic myeloproliferative neoplasms, colon and rectal cancer, head and neck cancer (including head and neck squamous cell carcinoma (HN-SCC)), leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia), lymphoma (e.g., Burkitt lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)), plasma cell neoplasms (e.g., multiple myeloma), myelodysplastic syndrome, myelodysplastic/myeloproliferative neoplasms and chronic myeloproliferative neoplasms, pancreatic cancer and pancreatic neuroendocrine tumors (e.g., islet cell tumors), small intestine cancer, soft tissue sarcoma, and squamous cell carcinoma.

And in other embodiments of the methods, crystalline polymorphs or salts and uses as otherwise described herein, the cancer is selected from adrenocortical carcinoma, adrenal cortex cancer, AIDS-related cancers (e.g., as Kaposi sarcoma, AIDS-related lymphoma, Burkitt lymphoma, and primary CNS lymphoma), anal cancer, appendix cancer, astrocytomas (e.g., childhood cerebellar or cerebral), bile duct cancer (e.g., cholangiocarcinoma), bladder cancer, bone cancer (e.g., Ewing sarcoma, osteosarcoma and malignant fibrous histiocytoma), brain tumors (e.g., glioblastoma multiforme, cerebellar astrocytoma, cerebral astrocytoma/malignant glioma, ependymoma, medulloblastoma, oligodendroglioma, supratentorial primitive neuroectodermal tumors, and visual pathway and hypothalamic glioma), brainstem glioma, breast cancer, bronchial tumors, gastrointestinal carcinoid tumor, carcinoid tumors, carcinoma of unknown primary, cardiac (heart) tumors, central nervous system caner (e.g., atypical teratoid/rhabdoid tumor, embryonal tumors, and germ cell tumors), cervical cancer, childhood cancers, chondrosarcoma, chronic myeloproliferative neoplasms, colon and rectal cancer, craniopharyngioma, desmoplastic small round cell tumor, ductal carcinoma in situ (DCIS), endometrial cancer, ependymoma, epitheloid hemangioendothelioma (EHE), esophageal cancer, esthesioneuroblastoma, extracranial germ cell tumor, extragonadal germ cell tumor, eye cancer (e.g., intraocular melanoma, and retinoblastoma), fallopian tube cancer, gallbladder cancer, gastric (stomach) cancer, gastrointestinal stromal tumors (GIST), gestational trophoblastic disease (GTD), gliomas, hairy cell leukemia, head and neck cancer (e.g., head and neck squamous cell carcinoma (HNSCC)), hepatocellular (liver) cancer, histiocytosis, langerhans cell, hypopharyngeal cancer, kidney cancer, langerhans cell histiocytosis, laryngeal cancer, laryngeal cancer and papillomatosis, leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia), lip and oral cavity cancer, liver cancer, lung cancer (e.g., small cell lung cancer, non-small cell lung cancer (NSCLC), lung adenocarcinoma, carcinoma of the lung, and squamous carcinoma of the lung), lung carcinoid tumor, lymphoma (e.g., Burkitt lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)), male breast cancer, meningiomas, mesothelioma, midline tract carcinoma involving NUT gene, mouth cancer, multiple endocrine neoplasia syndrome, plasma cell neoplasm (e.g., multiple myeloma), mycosis fungoides, myelodysplastic syndrome, myelodysplastic/myeloproliferative neoplasms and chronic myeloproliferative neoplasms, nasal cavity and paranasal sinus cancer, nasopharyngeal cancer (NPC), neuroblastoma, oral cancer, lip and oral cavity cancer and oropharyngeal cancer, ovarian cancer, pancreatic cancer and pancreatic neuroendocrine tumors (e.g., islet cell tumors), paraganglioma, parathyroid cancer, penile cancer, pharyngeal cancer, pheochromocytoma, pituitary tumor, pleuropulmonary blastoma, primary peritoneal cancer, prostate cancer, retinoblastoma, rhabdomyosarcoma, salivary gland cancer, Sézary syndrome, skin cancer (e.g., basal and squamous cell carcinoma, merkel cell carcinoma, and melanoma), small intestine cancer, soft tissue sarcoma, squamous cell carcinoma, stomach (gastric) cancer, testicular cancer, throat cancer, thymoma and thymic carcinoma, thyroid cancer, transitional cell cancer of the renal pelvis and ureter, urethral cancer, uterine cancer and uterine Sarcoma, vaginal cancer, vascular tumors, vulvar cancer, and Wilms tumor.

For example, in a few particular embodiments of methods, crystalline polymorphs or salts and uses as otherwise described herein, the cancer is a solid tumor. The solid tumor can be in various embodiments, for example, a lung cancer, a colorectal cancer, or a pancreatic cancer.

In one particular embodiment of the methods, crystalline polymorphs or salts and uses as otherwise described herein, the cancer is diffuse large B-cell lymphoma.

KRAS mutations are found in >90% of pancreatic cancers, 50% of colon cancers and 25% of lung adenocarcinomas. Accordingly, in certain embodiments of the methods, crystalline polymorph and uses as otherwise described herein, the cancer has a mutant KRAS gene, e.g., a heterozygous mutant.

The person of ordinary skill in the art will determine effective amounts and dosages of the crystalline polymorphs or salts described herein based on this disclosure in view of the current state of the art.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" or "effective amount" refers to the amount of active crystalline polymorph that elicits the biological or medicinal response that is being sought in a tissue, system, animal, individual or human by a researcher, veterinarian, medical doctor or other clinician.

In certain embodiments, an effective amount can be an amount suitable for
(i) inhibiting the progression the disease;
(ii) prophylactic use for example, preventing or limiting development of a disease, condition or disorder in an individual who may be predisposed or otherwise at risk to the disease, condition or disorder but does not yet experience or display the pathology or symptomatology of the disease;
(iii) inhibiting the disease; for example, inhibiting a disease, condition or disorder in an individual who is experiencing or displaying the pathology or symptomatology of the disease, condition or disorder;
(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or
(v) eliciting the referenced biological effect.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof, or inhibiting the progression of disease; or (ii) eliciting the referenced biological effect (e.g., inducing apoptosis, or inhibiting glutathione synthesis).

Pharmaceutical Compositions and Dosage Forms

A crystalline polymorph or a salt as described herein can usefully be provided in the form of a pharmaceutical composition. Such compositions include the polymorph according to any one of the preceding aspects or embodiments described herein, together with a pharmaceutically acceptable excipient, diluent, or carrier. The pharmaceutical composition can be, for example, in the form of a tablet, a capsule, or a parenteral formulation, but the person of ordinary skill in the art will appreciate that the crystalline polymorph can be provided in a wide variety of pharmaceutical compositions.

The crystalline polymorphs or salts of the disclosure can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like. A medicament including a crystalline polymorph of the disclosure can be provided in any appropriate of the formulations and dosage forms as described herein.

Pharmaceutical compositions can be made using the presently disclosed crystalline polymorphs or salts. For example, in one embodiment, a pharmaceutical composition includes a pharmaceutically acceptable carrier, diluent or excipient, and crystalline polymorph as described above with reference to any one of structural formulae.

In the pharmaceutical compositions disclosed herein, one or more crystalline polymorphs or salts of the disclosure may be present in association with one or more pharmaceutically acceptable carriers, diluents or excipients, and, if desired, other active ingredients. The pharmaceutical compositions containing crystalline polymorphs or salts of the disclosure may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Crystalline polymorphs or salts of the disclosure can also be administered in the form of suppositories, e.g., for rectal administration of the drug. These compositions can be prepared by mixing the crystalline polymorph with a suitable non-irritating excipient that is solid at ordinary temperatures but liquid at the rectal temperature and will therefore melt in the rectum to release the drug. Such materials include cocoa butter and polyethylene glycols.

Crystalline polymorphs or salts of the disclosure can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active crystalline polymorph can be effective over a wide dosage range and is generally administered in a pharmaceutically effective amount. It will be understood, however, that the amount of the crystalline polymorph actually administered will usually be determined by a physician, according to the relevant circumstances, including the condition to be treated, the chosen route of administration, the actual crystalline polymorph administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a crystalline polymorph described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a crystalline polymorph described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of crystalline polymorph or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the crystalline polymorph preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the crystalline polymorphs or salts can vary according to, for example, the particular use for which the treatment is made, the manner of administration of the crystalline polymorph, the health and condition of the patient, and the judgment of the prescribing physician. The proportion or concentration of a crystalline polymorph described herein in a pharmaceutical composition can vary depending upon a number of factors including dosage, chemical characteristics (e.g., hydrophobicity), and the route of administration. For example, the crystalline polymorphs or salts described herein can be provided in an aqueous physiological buffer solution containing about 0.1 to about 10% w/v of the crystalline polymorph for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the crystalline polymorph selected, formulation of the excipient, and its route of administration. Effective doses can be extrapolated from dose-response curves derived from in vitro or animal model test systems.

The crystalline polymorphs or salts described herein can also be formulated in combination with one or more additional active ingredients which can include any pharmaceutical agent such as anti-viral agents, vaccines, antibodies, immune enhancers, immune suppressants, anti-inflammatory agents and the like.

The person of ordinary skill in the art will formulate a crystalline polymorph or the salt as described into pharmaceutical formulations herein. For example, based on the physicochemical properties of the crystalline polymorph, the amount of the crystalline polymorph or the salt needed for a pharmaceutically effective amount, and the desired route of administration.

EXAMPLES

The preparation of the crystalline polymorphs or salts of the disclosure is illustrated further by the following examples, which are not to be construed as limiting the disclosure in scope or spirit to the specific procedures and crystalline polymorphs or salts described in them.

Example 1: Preparation of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic Acid (Compound 1)

Compound 1 is described as compound no. 5 in International Patent Application Publication no. WO2018/102453, which is hereby incorporated by reference in its entirety.

3-(2-bromo-5-chlorophenoxy)oxetane

Diisopropyl diazocarboxylate (292 mg, 1.45 mmol) was added to a solution of 2-bromo-5-chlorophenol (200 mg, 0.964 mmol), oxetan-3-ol (89 mg, 1.2 mmol) and triphenylphosphine (379 mg, 1.45 mmol) in THF (4.2 mL). The reaction mixture was stirred at r.t. for 18 h. Ethyl acetate was added and the mixture was washed with 1N NaOH (3×). The organic layer was dried with sodium sulfate, filtered and evaporated under reduced pressure. The crude product was purified by flash chromatography on silica gel using a solution of ethyl acetate in hexanes (10%) to give the title compound (208 mg, 0.789 mmol, 82%).

2-(4-chloro-2-(oxetan-3-yloxy)phenyl)-4,4,5,5-tetramethyl-1,3,2-dioxaborolane Degassed dioxane was added to a mixture of 3-(2-bromo-5-chlorophenoxy)oxetane (100 mg, 0.379 mmol), pinacol diborane (116 mg, 0.455 mmol), [1,1'-Bis(diphenylphosphino)ferrocene]palladium(II) dichloride (28 mg, 0.038 mmol) and potassium acetate (112 mg, 1.14 mmol). The reaction mixture was heated at 85° C. for 18 hours. The mixture was filtered on celite and the pad was washed with dioxane. The filtrate was evaporated to give the title compound (219 mg, 186%, 50% w/w from NMR analysis) that was used as is.

2-chloro-5-(isopropylthio)thiazole

A 2.5 M solution of n-BuLi in hexanes (20.5 mL, 51.2 mmol) was added to a THF solution (117 mL) of 2-chlorothiazole (4.9 g, 41.0 mmol) at −78° C. The reaction mixture was stirred at the same temperature for 30 min. Diisopropyl disulfide (13.1 mL, 82.0 mmol) was added to the reaction and was stirred at the same temperature for 1.5 h. Water was added to quench the reaction and then $Et_2O$. The reaction mixture was transferred into a separation funnel and the aqueous layer was extracted with $Et_2O$ (3×). The combined organic layers were dried over $Na_2SO_4$ and concentrated under vacuum. The crude product was purified by flash chromatography on silica gel (dry packing) using a solution of EtOAc in hexanes (0 to 5% gradient) and afforded the title compound (2.31 g, 11.9 mmol, 29%) as yellow liquid.

4-bromo-2-chloro-5-(isopropylthio)thiazole

A 2 M solution of bromine (72.7 µL, 1.42 mmol) in dichloromethane ("DCM") was added dropwise to a solution of 2-chloro-5-(isopropylthio)thiazole (250 mg, 1.29 mmol) in DCM. The reaction was stirred for 3 hours at room temperature. A solution of $Na_2SO_3$ was added and the aqueous layer was extracted with DCM (3×). The combined organic layers were washed with brine, dried over $Na_2SO_4$, filtered and concentrated under vacuum. The crude product was purified by flash chromatography on silica gel using a solution of DCM in hexanes (50 to 100% gradient) and afforded the title compound (271 mg, 0.99 mmol, 77%) as colorless liquid.

4-bromo-2-hydrazinyl-5-(isopropylthio)thiazole

DIPEA (64 µL, 0.37 mmol) was added to a solution of hydrazine hydrochloride (13.0 mg, 0.18 mmol) and 4-bromo-2-chloro-5-(isopropylthio)thiazole (50.0 mg, 0.18 mmol) to NMP (2 mL) in a glass microwave vial. The vial was sealed and was heated to 150° C. for 1 h with microwave radiation. The crude product was purified by reverse flash chromatography (C18, using a gradient 0 to 40 to 70% MeCN in $H_2O$ with 10 mM $NH_4CO_2H$ buffer) and afforded the title compound (29.0 mg, 0.11 mmol, 59%) as yellow solid after extraction with $Et_2O$ and concentration under vacuum.

methyl 2-(methoxyimino)-3-(2-nitrobenzyl)-4-oxopentanoate

Methyl acetopyruvate (1.0 g, 6.94 mmol), methoxyhydroxylamine hydrochloride (0.58 g, 6.94 mmol) and molecular sieves (2.5 g) were placed in a flame dried round bottom flask equipped with a nitrogen inlet. Dry DMF (23 mL) was added and the round bottom flask was covered with foil and stirred overnight at room temperature. The reaction mixture was diluted with EtOAc (150 mL) and the organic phase was washed with water (3×50 mL) and brine (1×50 ml), dried with $Na_2SO_4$, filtered and concentrated under vacuum to afford the title compound (1.07 g, 6.16 mmol, 89%) as red liquid.

methyl 1-(4-bromo-5-(isopropylthio)thiazol-2-yl)-3-methyl-1H-pyrazole-5-carboxylate Methyl 2-(methoxyimino)-3-(2-nitrobenzyl)-4-oxopentanoate (4.00 g, 23.1 mmol) was dissolved in MeOH (115 mL). 4-bromo-2-hydrazinyl-5-(isopropylthio)thiazole (6.19 g, 23.1 mmol) was added and then HCl 12 N (7.70 mL, 92.4 mmol) was added dropwise to the reaction mixture. The reaction mixture was heated to reflux overnight. The crude product was concentrated under vacuum and was purified by flash chromatography on silica gel (dry packing) using a solution of EtOAc in hexanes (5 to 20% gradient) and was purified a second time by flash chromatography on silica gel (dry packing) using a solution of DCM in hexanes (10 to 50% gradient) and afforded the title compound (1.89 g, 5.02 mmol, 22%) as orange oil.

methyl 4-bromo-1-(4-bromo-5-(isopropylthio)thiazol-2-yl)-3-methyl-1H-pyrazole-5-carboxylate A 2 M solution of bromine (3.32 mL, 6.64 mmol) in MeCN was added dropwise to a solution of methyl 1-(4-bromo-5-(isopropylthio)thiazol-2-yl)-3-methyl-1H-pyrazole-5-carboxylate (500 mg, 1.33 mmol) in a solution of DCM/MeCN (7 mL, 1:1). The reaction was stirred for 5 hours at room temperature. A solution of $Na_2SO_3$ was added and the aqueous layer was extracted with $Et_2O$ (3×). The combined organic layers were washed with brine, dried over $Na_2SO_4$, filtered and concentrated under vacuum. The crude product was purified by flash chromatography on silica gel using a solution of DCM in hexanes (20%) and afforded the title compound (421 mg, 0.93 mmol, 70%) as orange solid.

methyl 4-bromo-1-(5-(isopropylthio)-4-(4-(trifluoromethyl)cyclohex-1-en-1-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), 4,4,5,5-tetramethyl-2-(4-(trifluoromethyl)cyclohex-1-en-1-yl)-1,3,2-dioxaborolane (51.6 mg, 0.187 mmol) and $K_2CO_3$ (152 mg, 1.10 mmol) nitrogen and vacuum cycles were performed (2×). Nitrogen gas was bubbled through a solution of THF (2 mL) and then the solution was added to the microwave vial, followed by the addition of the catalyst $Pd(dtbpf)Cl_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (0 to 10% gradient) and afforded the title compound (47.4 mg, 0.090 mmol, 41%) as yellow oil.

4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(5-(isopropylthio)-4-(4-(trifluoromethyl)cyclohex-1-en-1-yl)thiazol-2-yl)-3-methyl-1H-pyrazole-5-carboxylate (47.4 mg, 0.090 mmol), 3-fluorophenylboronic acid (15.2 mg, 0.108 mmol) and $Na_2CO_3$ (47.9 mg, 0.452 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (10.4 mg, 0.009 mmol). The vial was capped and placed in an oil bath at 85° C. for 16 h. The reaction mixture was diluted with EtOAc and transferred into an extraction funnel. The layers were separated and the aqueous layer was extracted with EtOAc (3×). The combined organic layers were dried over $Na_2SO_4$, filtered and concentrated under vacuum. THF/MeOH (2 mL, 1:1) and NaOH 1M (181 μL, 0.181 mmol) were added and the reaction was stirred 16 h at rt. The product was purified using a semi prep HPLC-MS (column X-Bridge 30×50, eluted with 55-75% MeCN/$NH_4CO_2H$ 10 mM, pH 3.8/Flow 45 m/min/11 min), resulting in the title compound (12.8 mg, 0.024 mmol, 27%) as yellow solid after lyophilisation.

$^1H$ NMR (500 MHz, DMSO) δ 7.53-7.42 (m, 1H), 7.30-7.23 (m, 2H), 7.22-7.15 (m, 1H), 6.41 (s, 1H), 3.32-3.22 (m, 1H), 2.74-2.60 (m, 1H), 2.50-2.33 (m, 3H), 2.26 (s, 3H), 2.23-2.15 (m, 1H), 2.07-1.97 (m, 1H), 1.57-1.46 (m, 1H), 1.23 (dd, J=6.7, 3.4 Hz, 6H); MS (m/z): 526.3 $[M+1]^+$.

Sodium 4-(3-fluorophenyl)-2-[5-isopropylsulfanyl-4-[4-(trifluoromethyl)cyclohexen-1-yl]thiazol-2-yl]-5-methyl-pyrazole-3-carboxylate 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid can be converted to its sodium salt by treatment with sodium hydroxide in tetrahydrofuran followed by evaporation of solvent and washing of the solid with water to provide a crude sodium salt. Alternatively, the saponification of the methyl ester can be performed under conditions to provide crude sodium salt directly.

The crude sodium salt can then be recrystallized. In one preparation, 56 g (0.10 mol) of crude sodium salt was dissolved in tetrahydrofuran (500 mL) and filtered. To this solution was added acetonitrile (250 mL) and the solution concentrated to 350 mL at 50° C. under reduced pressure. Acetonitrile (250 mL) was added again and the resulting solution concentrated to 300 mL at 50° C. under reduced pressure, resulting in crystallization. To this mixture acetonitrile (250 ml) was added and again concentrated to 500 mL at 50° C. under reduced pressure. The mixture was then allowed to stand 1 h at 50° C., then cooled to 20° C. for 1 h, then cooled to 0° C. for 30 min. The resulting mixture was filtered and the solid washed with cold acetonitrile (2×100 mL, 0° C.) and dried at 35° C. under reduced pressure to provide the sodium salt (54.7 g, 98%). MS (m/z): 525.85 $[M-Na+2]^+$. $^1H$ NMR (500 MHz, DMSO-$d^6$) δ 14.16 (br s, 1H), 7.50-7.55 (m, 1H), 7.23-7.31 (m, 3H), 6.44 (m, 1H), 3.32 (m, 1H), 2.68-2.74 (m, 1H), 2.55-2.64 (m, 1H), 2.43-2.55 (m, 1H), 2.30 (s, 3H), 2.20-2.30 (m, 1H), 2.02-2.09 (m, 1H), 1.50-1.60 (m, 1H), 1.26 (d, 6H, J=7.5 Hz). $^{13}C$ NMR (126 MHz, DMSO-$d^6$) δ 163.51, 162.37, 161.58, 157.70, 154.94, 150.62, 133.49, 132.86, 132.79, 131.44, 131.23, 131.16, 129.80, 127.98, 127.59, 125.55, 125.52, 125.38, 122.20, 120.09, 116.14, 115.96, 115.35, 115.19, 42.50, 26.71, 24.56, 23.15, 23.07, 21.64, 12.76.

4-(3-fluorophenyl)-2-[5-isopropylsulfanyl-4-[4-(trifluoromethyl)cyclohexen-1-yl]thiazol-2-yl]-5-methyl-pyrazole-3-carboxylic Acid (1)

A 5 L flask was charged with the sodium salt described above (52.0 g, 94.9 mmol) and 10% acetonitrile in deionized water (1.0 L). The mixture was warmed to 50° C. and then treated with 0.1N HCl (1.0 equivalent) dropwise. As the addition progressed a change in the slurry was noted and it became thicker. As the addition approached 1.0 equivalents the pH dropped to about 3, the target pH being <4 to ensure complete protonation. After 2 hours the mixture was cooled to 22° C., filtered, washed with water, and dried with air to afford the title compound 1 as crystalline Form 1 (51.76 g, 99% yield). $^1H$ NMR (500 MHz, DMSO-$d^6$) δ 14.16 (s, 1H), 7.50-7.55 (m, 1H), 7.25-7.30 (m, 3H), 6.44 (s, 1H), 3.28-3.34 (quint, 1H), 2.69-2.73 (d, 1H), 2.44-2.48 (m, 2H), 2.29 (s, 3H) 2.24-2.27 (m, 2H), 2.04-2.08 (m, 1H), 1.51-1.59 (m, 1H), 1.26 (d, 6H). $^{13}C$ NMR (500 MHz, $CDCl_3$) δ 163.46, 162.46, 161.51, 156.70, 152.70, 152.35, 133.41, 132.85, 131.94, 131.03, 129.76, 125.39, 121.61, 116.79, 115.22, 42.69, 37.92, 26.89, 24.68, 23.02, 21.48, 12.30. $^{19}F$ NMR (500 MHz, $CDCl_3$) δ -73.62 (s), -113.17 (quint). MS (m/z): 526.3 $[M+1]^+$.

Example 2: Crystalline Polymorph Form 1

Crystalline polymorph Form 1 of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid (compound 1) was characterized by XRPD. FIG. 1A provides the XRPD pattern and FIG. 1D provides the FTIR spectrum for Form 1. This crystalline polymorph was also characterized by TGA, DSC and polarized light microscopy (PLM). As shown by DSC and TGA data in FIGS. 1B and 1C, respectively, Form 1 showed an onset of melting endotherm at 101.2° C., an endothermic peak at 123.4° C., and a negligible weight loss before 150° C. PLM images displayed Form 1 as needle like birefringent crystals. Based on the results, Form 1 was considered to be an anhydrate.

Example 3: Large Scale Anti-Solvent Recrystallization of Crystalline Polymorph Form 1

Compound 1 (2.088 g) obtained in Example 1 was placed into a 20 mL vial, dissolved in 2 mL acetone at 50° C., and then filtrated. The filtrate was seeded with 103.1 mg of crystalline polymorph Form 1 from Example 2. To the seeded filtrate 12 mL of water was slowly added, and the resulting suspension was stirred at room temperature overnight.

Then temperature cycling was used to improve the crystallinity. The suspension was maintained at 50° C. for 30 min, then the temperature was decreased to 20° C. at a rate of 0.1° C./min followed by an increase to 50° C. at a rate of 0.5° C./min. Then the temperature was decreased to 20° C. at a rate of 0.1° C./min followed by an increase to 50° C. at a rate of 0.5° C./min. Finally, the temperature was decreased to 20° C. at a rate of 0.1° C./m and maintained at 20° C. before the solid was isolated. The anti-solvent crystallization provided about 1.5 g (about 67%) of crystalline polymorph, which conformed to Form 1 reference.

TGA and DSC measurements indicated weight loss of 0.1% at 150° C. and an endothermic peak at 120.0° C. PLM images displayed a rod-like birefringent crystals in the sample with particle-size distribution (PSD) of $D_{10}$=0.16 μm, $D_{50}$=0.36 μm, and $D_{90}$=3.72 μm ($D_{10}$=0.16 μm, $D_{50}$=0.35 μm, and $D_{90}$=1.42 μm after sonication for 5 min). Dynamic vapor sorption (DVS) showed 0.6% water uptake at 25° C./80% relative humidity, indicating that Form 1 was slightly hygroscopic. As displayed in FIG. 1E, no form change was observed before and after DVS.

The reverse anti-solvent recrystallization was also successful on about 1.1 g scale in 1 mL acetone at 50° C. The dissolved compound was filtered, and the filtrate was slowly added (about 50 L/sec) to a water solution previously seeded with a crystalline polymorph Form 1 from Example 2 (97 mg of seed in 6 mL of water). The resulting suspension was stirred at room temperature for 24 hours, filtered, washed with water, and air dried for 2 days. The reverse anti-solvent crystallization provided about 1 g (about 85%) of crystalline polymorph, which conformed to Form 1 reference. As provided in FIG. 1F, both the anti-solvent recrystallization and the reverse anti-solvent recrystallization resulted in crystalline polymorphs that conformed to Form 1 reference.

Example 4: Solubility and Stability of Crystalline Polymorph Form 1

The solubility of crystalline polymorph Form 1 was tested in biologically relevant media: water, simulated gastric fluid (SGF), fasted state simulated intestinal fluid (FaSSIF) and fed state simulated intestinal fluid (FeSSIF). For example, the crystalline polymorph was suspended in the solvent with stirring at 400 rpm at 37° C. for 1 h, 4 h and 24 h followed by filtration. The supernatant concentration was measured by HPLC (Mobile phase A: 0.1% $NH_3$ in $H_2O$, Mobile phase B: acetonitrile; flow rate: 0.8 mL/min; injection volume: 5 μL). The remaining solids were tested by XRPD. The results of solubility and pH were summarized in Table 1. In addition, no form change was observed by XRPD in water, SGF and FeSSIF; and one unknown peak was observed at about 31 2θ degrees for the polymorph in FaSSIF.

TABLE 1

| Media | Solubility (mg/mL) | | | pH | | |
|---|---|---|---|---|---|---|
| | 1 hr | 4 hr | 24 hr | 1 hr | 4 hr | 24 hr |
| $H_2O$ | 0.49 | 1.3 | 1.7 | 7.00 | 7.82 | 6.68 |
| SGF | 0.05 | 0.03 | 0.03 | 1.93 | 1.75 | 1.83 |
| FaSSIF | 0.14 | 0.22 | 0.20 | 6.55 | 5.75 | 5.12 |
| FeSSIF | 0.17 | 0.18 | 0.14 | 5.07 | 5.06 | 4.94 |

Physical and chemical stability evaluation has been performed for crystalline polymorph Form 1 under stressed conditions. In the experiments, about 10 mg of the polymorph was placed into 4 ml glass vials that were stored under 40° C./75% RH for 1 week. HPLC was utilized to evaluate the degradation, and XPRD was used to evaluate the crystalline polymorph. Both tests showed that Form 1 is physically stable (i.e., polymorph is unchanged with minimal or no degradation) under 40° C./75% RH for 1 week.

Example 5: Crystalline Polymorph Form 2

Crystalline polymorph Form 1 (20 mg) was suspended in 0.2-0.9 mL of methyl tert-butyl ether (MTBE). The resulting slurry was stirred at room temperature for 4 days, after which the remaining solids were isolated and subjected to XRPD. XRPD pattern shown in FIG. 2 suggested Form 2 is metastable and partially converted to Form 1 upon drying under ambient condition.

Example 6: Crystalline Polymorph Form 3

Figure 3B:
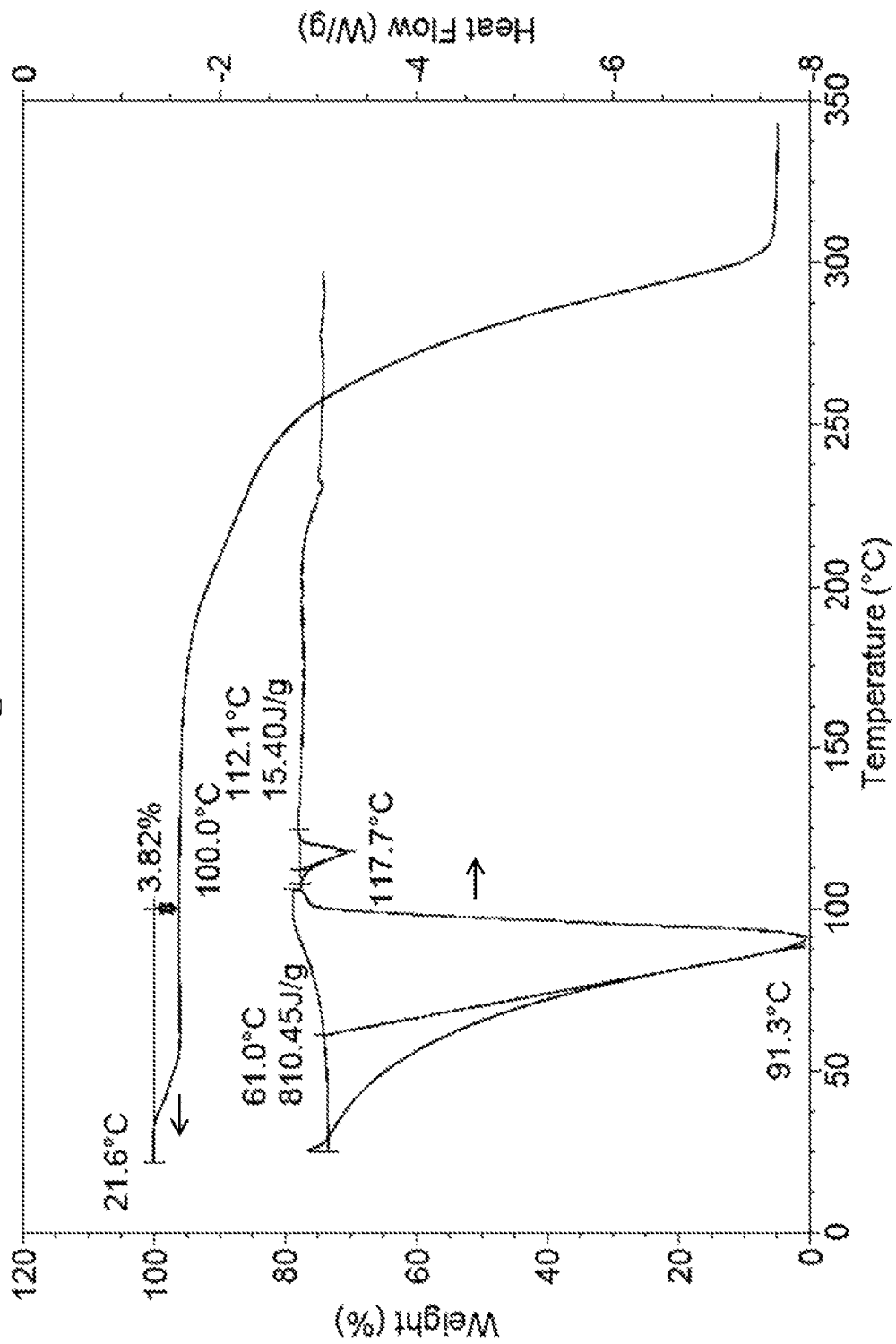
FIG. 3B shows a TGA and a DSC profile for the crystalline polymorph Form 3.

Crystalline polymorph Form 1 (20 mg) was suspended in 0.2-0.9 mL of 1,4-dioxane:$H_2O$ (1:3 v:v). The resulting slurry was stirred at room temperature for 4 days, after which the remaining solids were isolated and subjected to XRPD. FIG. 3A provides XRPD pattern for Form 3. This crystalline polymorph was also characterized by TGA, DSC, and PLM. As shown by TGA and DSC data in FIG. 3B, Form 3 showed endothermic peaks at 91.3° C. and 117.7° C., and a weight loss of 3.8% up to 100° C. PLM images displayed Form 3 as rod-like birefringent crystals. Based on the results, Form 3 was considered to be a hydrate or a solvate.

Example 7: Crystalline Polymorph Form 4

Figure 4A:
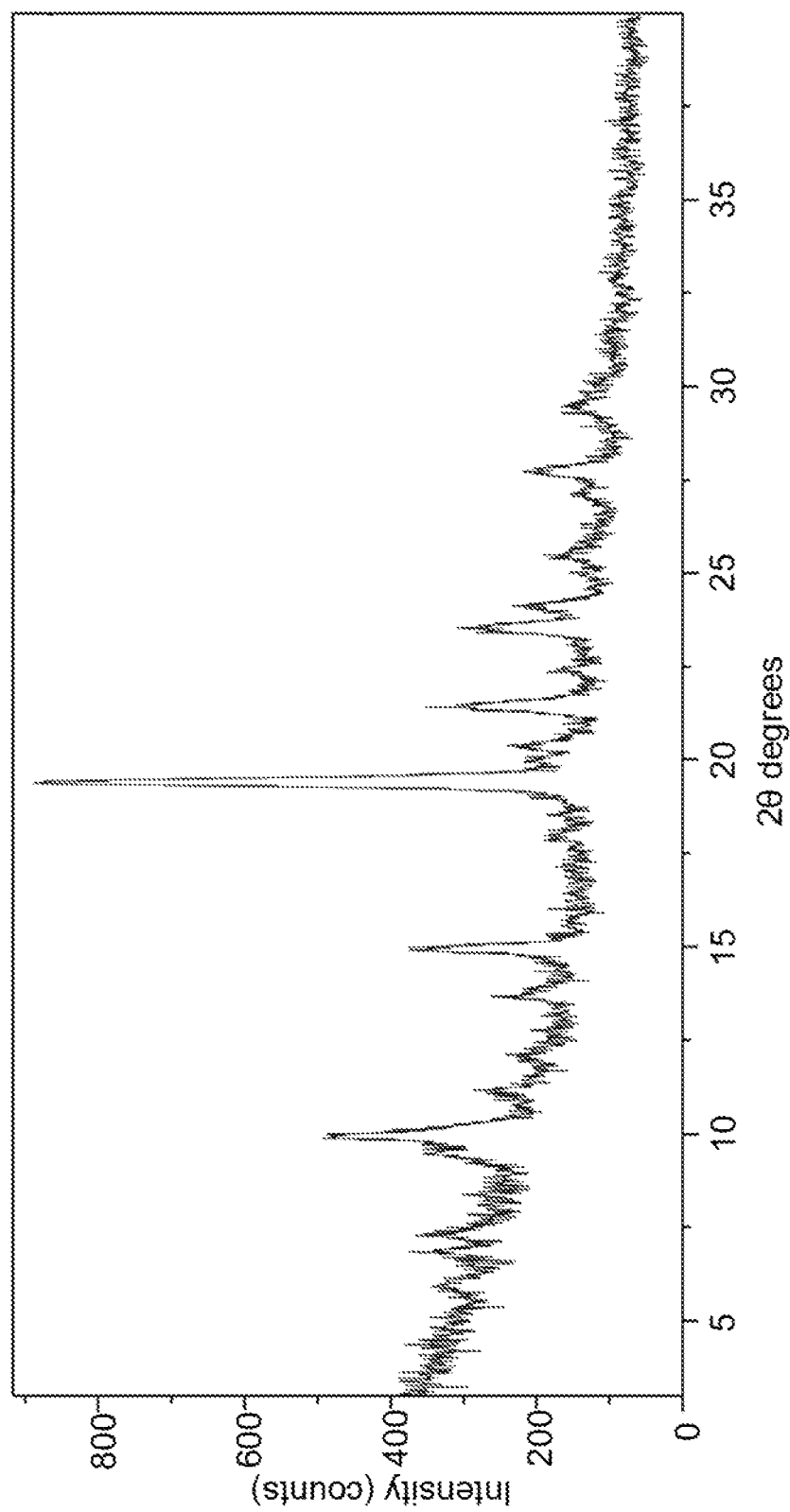
FIG. 4A shows a XRPD pattern for the crystalline polymorph Form 4 (Example 7).

Crystalline polymorph Form 1 (20 mg) was suspended in 0.2-0.9 mL of dimethylformamide:$H_2O$ (1:3 v:v). The resulting slurry was stirred at room temperature for 4 days, after which the remaining solids were isolated and subjected to XRPD. FIG. 4A provides XRPD pattern for Form 4. This crystalline polymorph was also characterized by TGA, DSC, and PLM. As shown by TGA and DSC data in FIG. 4B, Form 4 showed endothermic peaks at 49.4° C. and 72.9° C., and a weight loss of 2.5% up to 100° C. PLM images displayed Form 4 as irregular shaped birefringent crystals. Based on the results, Form 4 was considered to be a hydrate or a solvate.

Example 8: Crystalline Polymorph Form 5

Figure 5A:
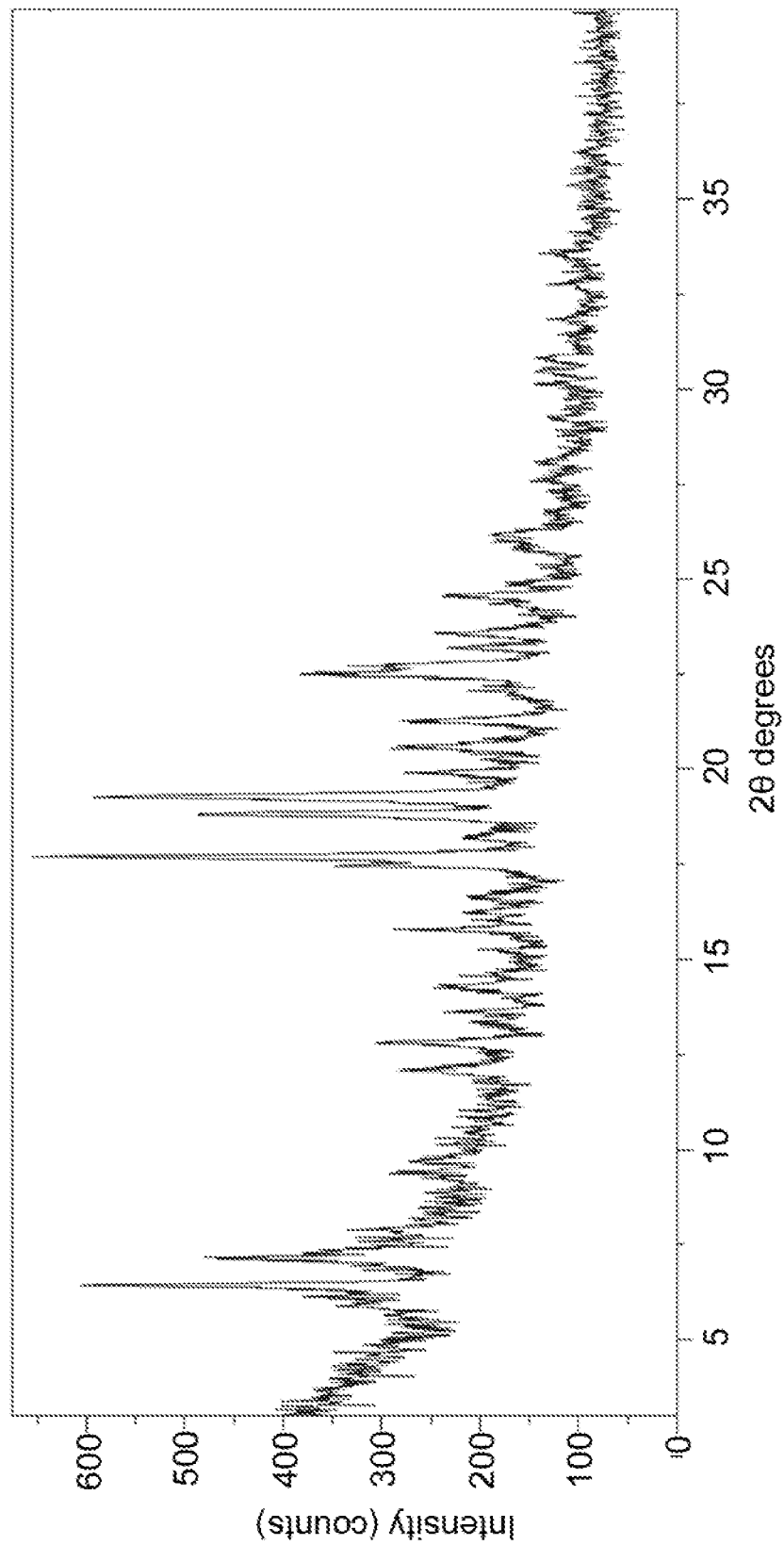
FIG. 5A shows a XRPD pattern for the crystalline polymorph Form 5 (Example 8).

Crystalline polymorph Form 1 (20 mg) was suspended in 0.2-0.9 mL of 2-methyltetrahydrofuran:n-heptane (1:6 v:v). The resulting slurry was stirred at room temperature for 4 days, after which the remaining solids were isolated and subjected to XRPD. Figure 5A provides XRPD pattern for Form 5. This crystalline polymorph was also characterized by TGA, DSC, and PLM. As shown by TGA and DSC data in FIG. 5B, Form 5 showed an endothermic peak at 141.9° C., and a negligible weight loss before decomposition. PLM images displayed Form 5 as irregular shaped birefringent crystals. Based on the results, Form 5 was considered to be an anhydrate.

Example 9: Conversion Between Form 1 and Form 5

To determine the thermodynamic stability relationship between Form 1 and Form 5, slurry conversion experiments were conducted. Specifically, Form 1 sample was added to 1.0 mL $H_2O$:acetone (9:1 v:v) or 0.8 mL of $H_2O$:ethanol (3:1 v:v) at room temperature. After equilibrium for 1 hr, the suspensions were filtered to obtain a saturated solution Form 1. To each saturated solution of Form 1:Form 5 (1:1) was added. After stirring at room temperature for 2 or 3 days, the solids were isolated for XRPD analysis. Only Form 1 was observed as shown in FIG. 5C. As a result Form 1 was determined to be the more thermodynamically stable than Form 5 at room temperature.

Example 10: Crystalline Polymorph Form 6

Figure 6B:
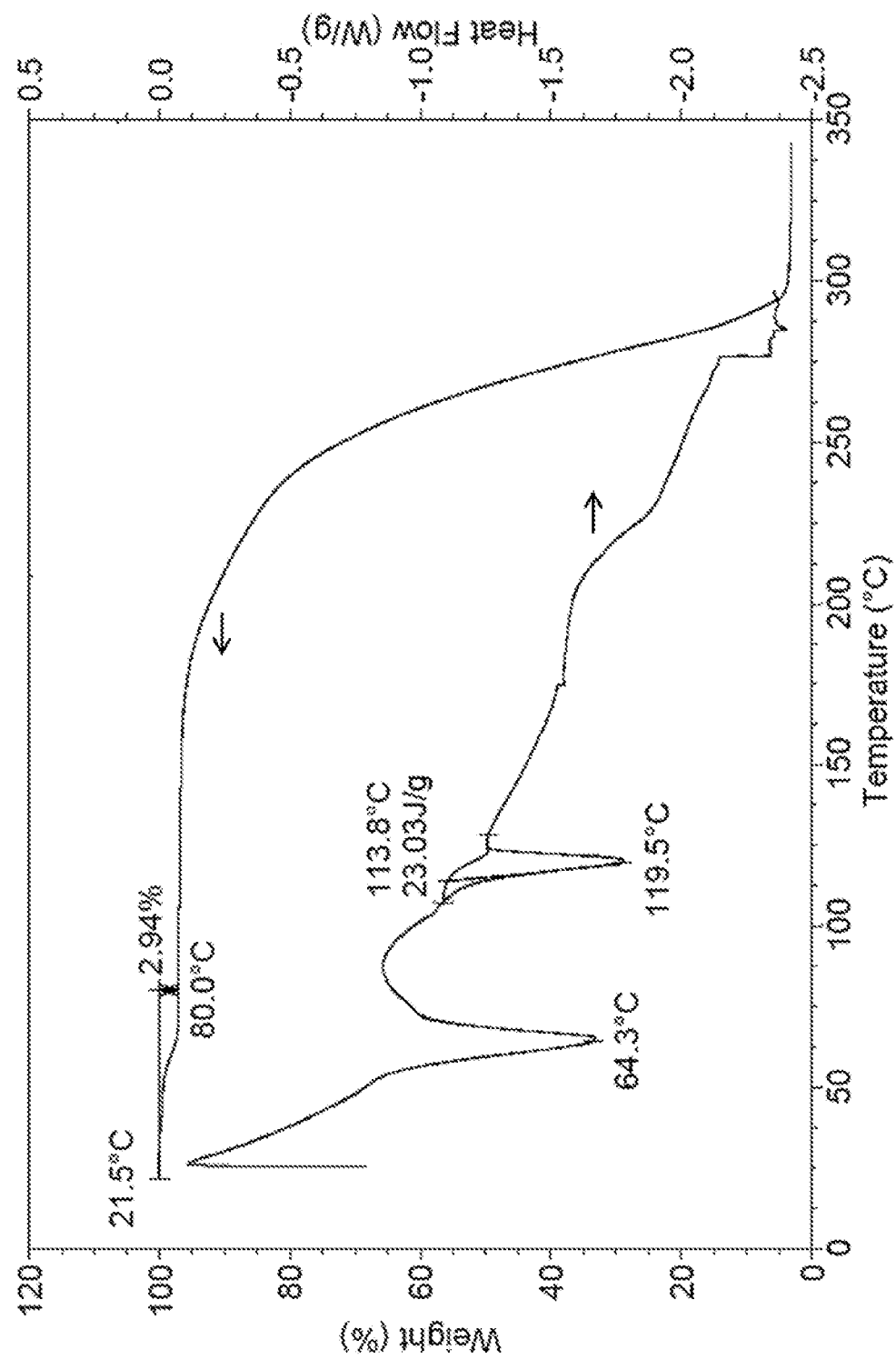
FIG. 6B shows a TGA and a DSC profile for the crystalline polymorph Form 6.

Crystalline polymorph Form 1 (20 mg) was suspended in 0.2-0.9 mL of methanol:$H_2O$ (937:63 v:v). The resulting slurry was stirred at room temperature for 4 days, after which the remaining solids were isolated and subjected to XRPD. FIG. 6A provides XRPD pattern for Form 6. This crystalline polymorph was also characterized by TGA, DSC, and PLM. As shown by TGA and DSC data in FIG. 6B, Form 6 showed endothermic peaks at 64.3° C. and 119.5° C., and a weight loss of 2.9% up to 80° C. PLM images displayed Form 6 as irregular shaped birefringent crystals. Based on the results, Form 6 was considered to be a hydrate or a solvate.

Example 11: Crystalline Polymorph Form 7

Figure 7A:
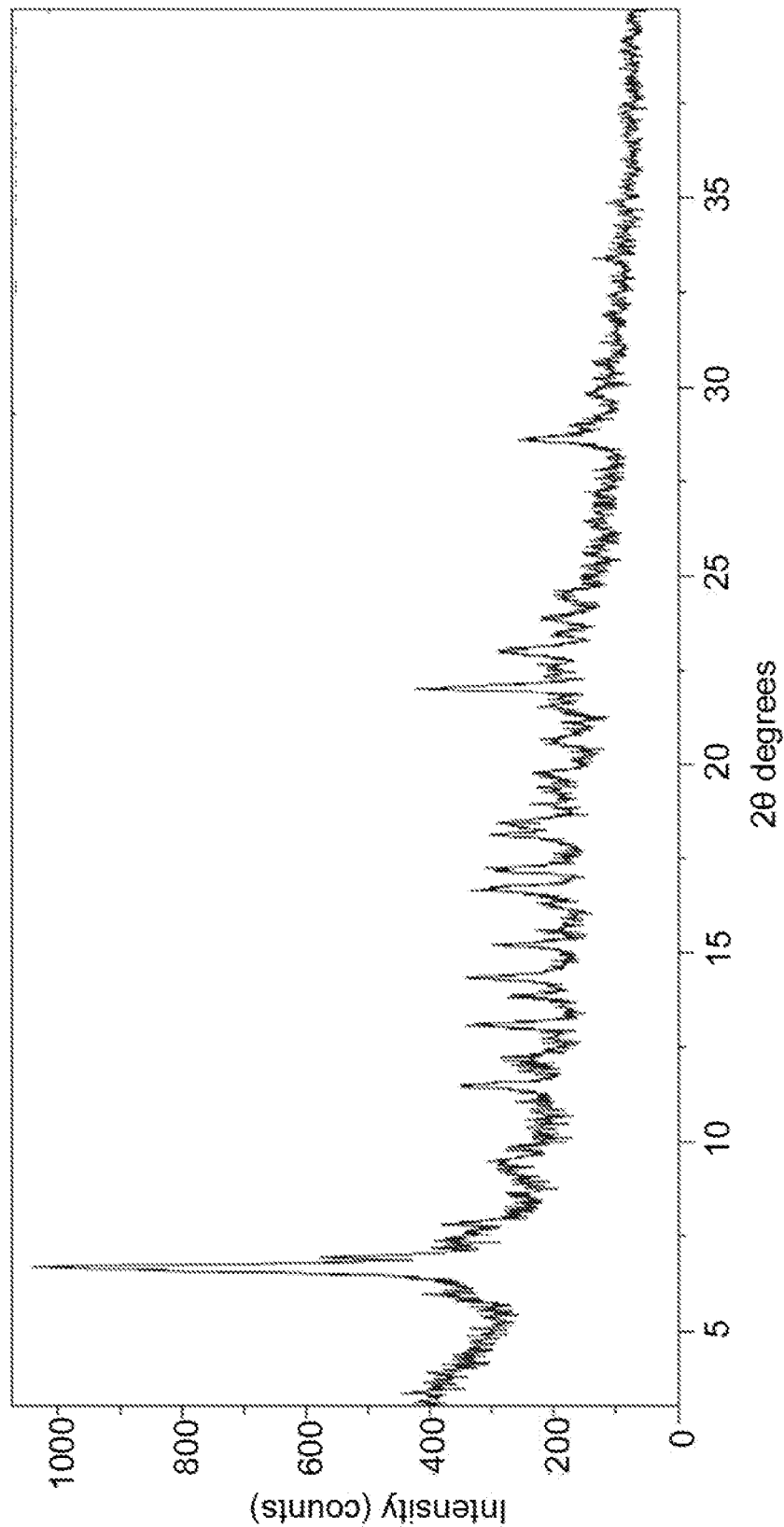
FIG. 7A shows a XRPD pattern for the crystalline polymorph Form 7 (Example 11).

Crystalline polymorph Form 1 (15 mg) was suspended in 0.5 mL of acetone. The resulting visually clear solutions were covered by Parafilm® with 5-10 pinholes, and left to evaporate at room temperature. The remaining solids were isolated and subjected to XRPD. FIG. 7A provides XRPD pattern for Form 7. This crystalline polymorph was also characterized by TGA, DSC, and PLM. As shown by TGA and DSC data in FIG. 7B, Form 7 showed endothermic peaks at 52.2° C. and 108.4° C., and a weight loss of 1.4% up to 130° C. PLM images displayed Form 7 as irregular shaped birefringent crystals. Based on the results, Form 7 was considered to be a hydrate or a solvate.

Example 12: Crystalline Polymorph Form 8

Crystalline polymorph Form 1 (20 mg) was suspended in 0.2-0.9 mL of tetrahydrofurane:$H_2O$ (1:9 v:v). The resulting slurry was stirred at room temperature for 4 days, after which the remaining solids were isolated and subjected to XRPD. XRPD pattern shown in FIG. 8 suggested Form 8 is metastable and partially converted to Form 1 upon drying under ambient condition.

Example 13: Crystalline Polymorph Form 9

Figure 9B:
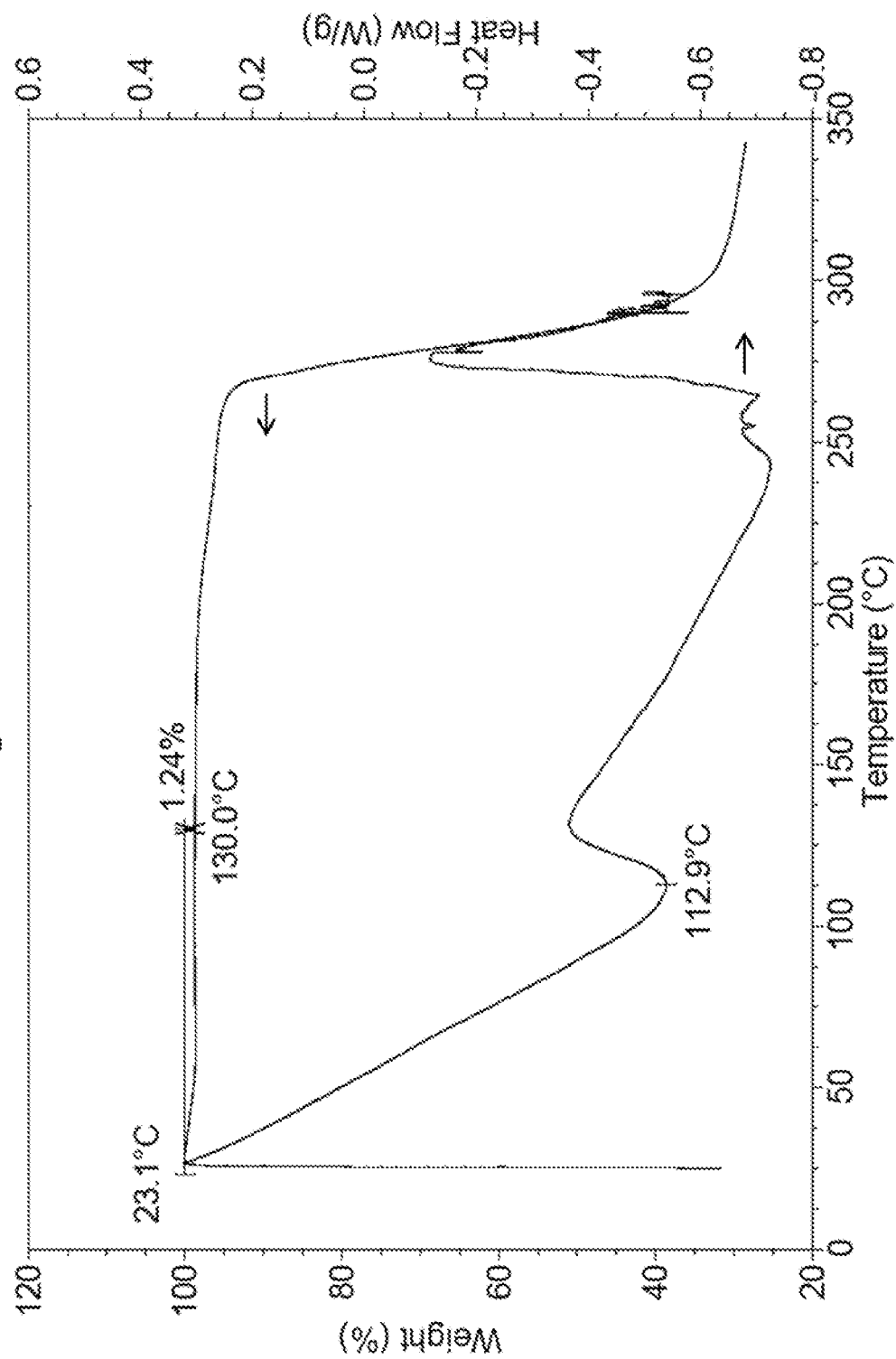
FIG. 9B shows a TGA and a DSC profile for the crystalline polymorph Form 9.

A solution of crystalline polymorph Form 1 (20 mg in 0.3 mL) was mixed with 0.3 mL a solution of KOH in ethyl acetate (1:1 molar ratio of KOH:Form 1), and then stirred for 2 to 5 days at room temperature. The solids were isolated and subjected to XRPD. The wet solids were also vacuum-dried at 50° C. for 2 hours, and then subjected to XRPD. FIG. 9A provides XRPD pattern for Form 9 where no change to the polymorph was observed during drying. This crystalline polymorph was also characterized by TGA, DSC, and PLM. As shown by TGA and DSC data in FIG. 9B, Form 9 showed a broad endothermic peak at 112.9° C., and a weight loss of 1.2% up to 130° C. PLM images displayed Form 9 as rod-like birefringent crystals. Based on the results, Form 9 was considered to be a hydrate or a solvate.

Example 14: Crystalline Polymorph Form 10

Figure 10A:
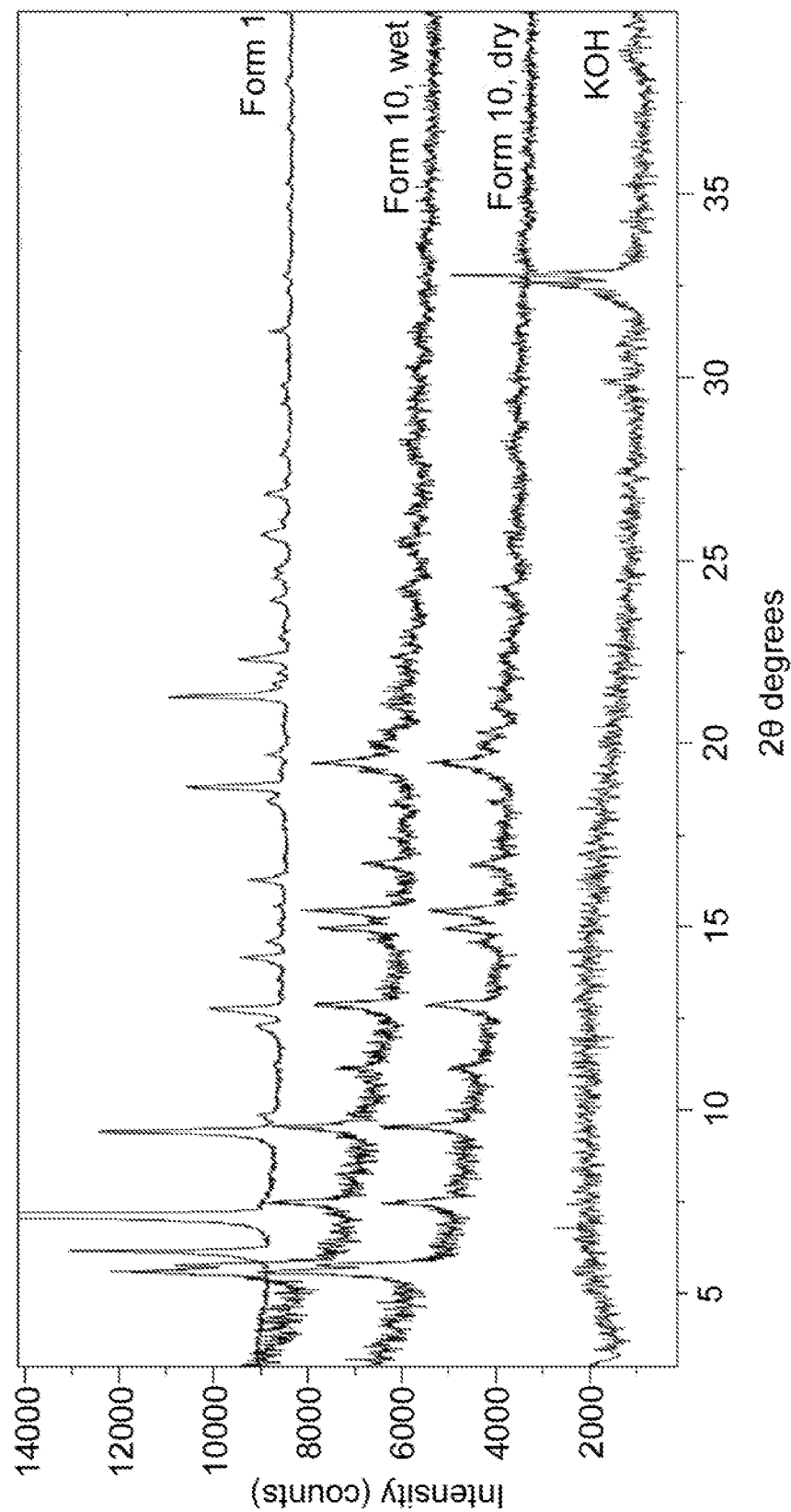
FIG. 10A shows a XRPD pattern for the crystalline polymorph Form 10 (Example 14).

A solution of crystalline polymorph Form 1 (20 mg in 0.3 mL) was mixed with 0.3 mL a solution of KOH in methanol (1:1 molar ratio of KOH:Form 1), and then stirred for 2 to 5 days at room temperature. The solids were isolated and subjected to XRPD. The wet solids were also vacuum-dried at 50° C. for 2 hours, and then subjected to XRPD. FIG. 10A provides XRPD pattern for Form 10 where no change to the polymorph was observed during drying. This crystalline polymorph was also characterized by TGA, DSC, and PLM. As shown by TGA and DSC data in FIG. 10B, Form 10 showed endothermic peaks at 61.8° C. and 143.8° C., and a weight loss of 4.3% up to 150° C. PLM images displayed Form 10 as irregular shaped birefringent crystals. Based on the results, Form 10 was considered to be a hydrate or a solvate.

Example 15: Crystalline Polymorph Form 11

Figure 11A:
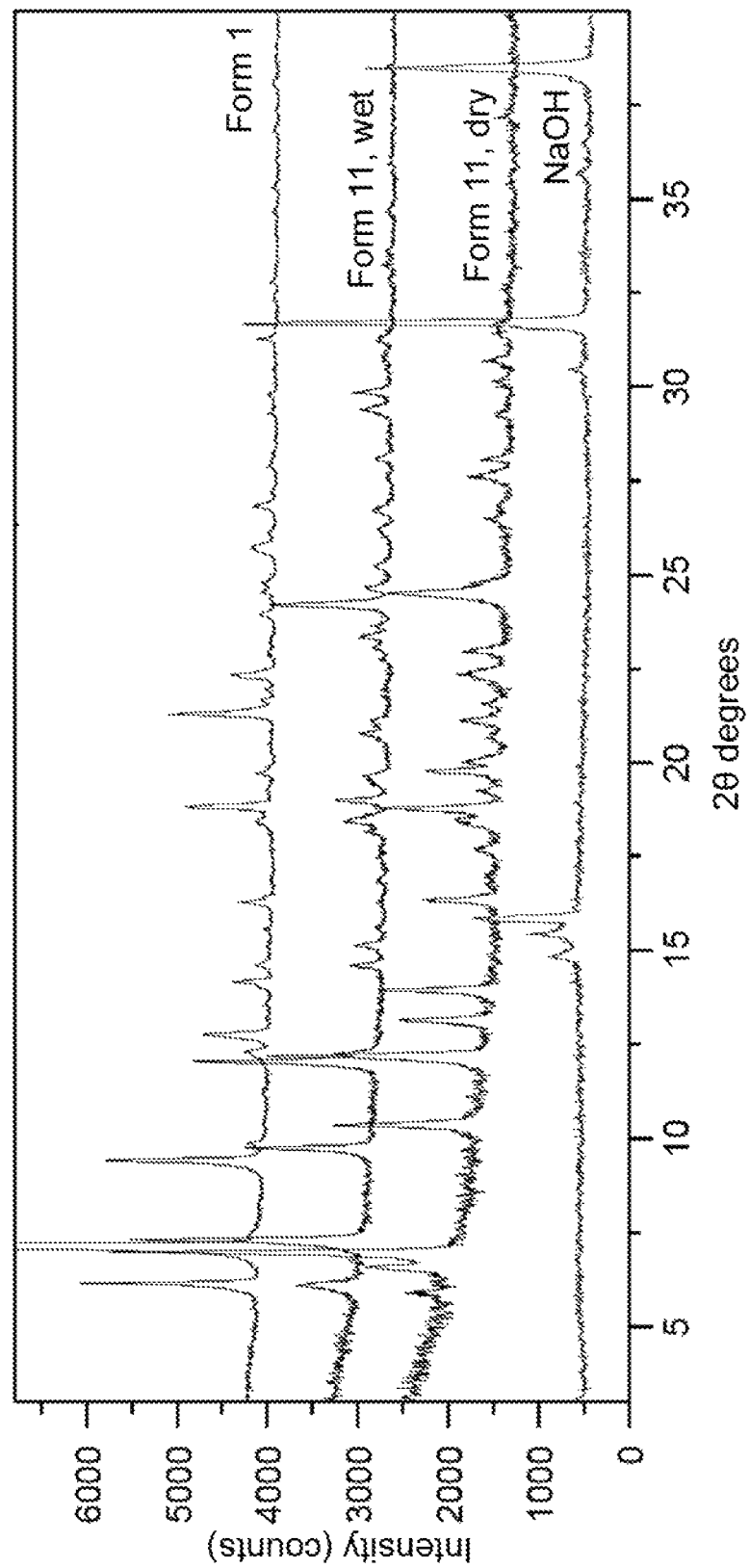
FIG. 11A shows a XRPD pattern for the crystalline polymorph Form 11 (Example 15).

A solution of crystalline polymorph Form 1 (20 mg in 0.3 mL) was mixed with 0.3 mL a of solution of NaOH in ethyl acetate (1:1 molar ratio of NaOH:Form 1), and then stirred for 2 to 5 days at room temperature. The solids were isolated and subjected to XRPD. The wet solids were also vacuum-dried at 50° C. for 2 hours, and then subjected to XRPD. FIG. 11A provides XRPD pattern for Form 11 where no change to the polymorph was observed during drying. This crystalline polymorph was also characterized by TGA, DSC, and PLM. As shown by TGA and DSC data in FIG. 11B, Form 11 showed a broad endothermic peak at 75.6° C., and a weight loss of 2.7% up to 90° C. PLM images displayed Form 11 as rod-like birefringent crystals. Based on the results, Form 11 was considered to be a hydrate or a solvate.

Example 16: Solubility of Crystalline Polymorph Form 11

The solubility of crystalline polymorph Form 11 was tested in biologically relevant media: water, SGF, FaSSIF, and FeSSIF. For example, the crystalline polymorph was suspended in the solvent with stirring at 400 rpm at 37° C. for 1 h, 4 h and 24 h followed by filtration. The supernatant was measured by HPLC for concentration and the remaining solids were tested by XRPD. The results of solubility and pH were summarized in Table 2. In addition, no form change was observed by XRPD in water and FaSSIF. Form 11 converted to Form 1 in SGF and FeSSIF.

TABLE 2

| Media | Solubility (mg/mL) | | | pH | | |
|---|---|---|---|---|---|---|
| | 1 hr | 4 hr | 24 hr | 1 hr | 4 hr | 24 hr |
| H$_2$O | 1.4 | 1.3 | 1.2 | 9.67 | 9.31 | 9.17 |
| SGF | 0.04 | 0.1 | 0.3 | 2.12 | 2.55 | 6.81 |
| FaSSIF | 0.1 | 0.1 | 0.2 | 6.48 | 6.45 | 6.56 |
| FeSSIF | 0.2 | 0.3 | 0.4 | 5.19 | 5.28 | 5.32 |

Example 17: Crystalline Polymorph Form 12

Figure 12A:
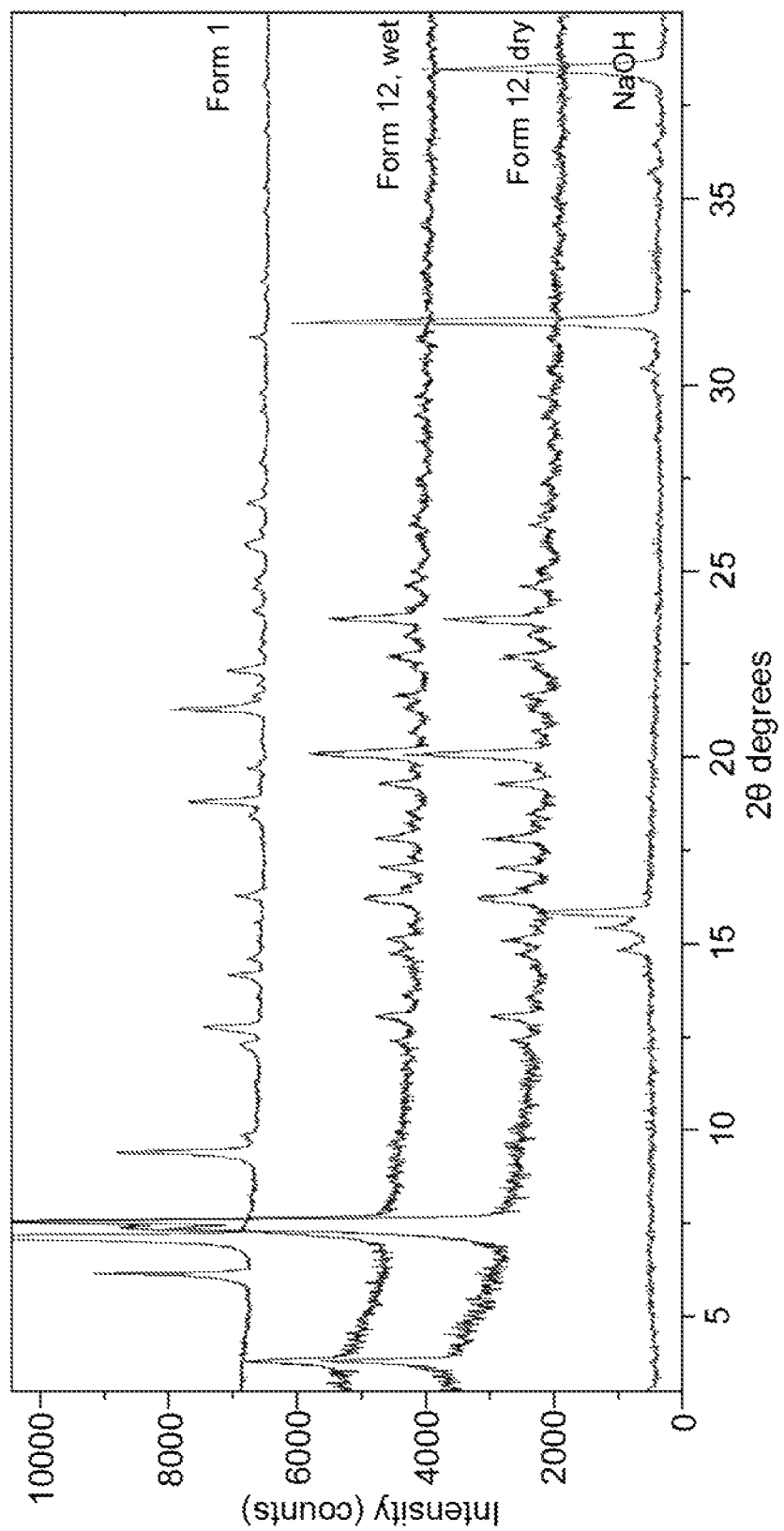
FIG. 12A shows a XRPD pattern for the crystalline polymorph Form 12 (Example 17).

A solution of crystalline polymorph Form 1 (20 mg in 0.3 mL) was mixed with 0.3 mL of a solution of NaOH in methanol (1:1 molar ratio of NaOH:Form 1), and then stirred for 2 to 5 days at room temperature. The solids were isolated and subjected to XRPD. The wet solids were also vacuum-dried at 50° C. for 2 hours, and then subjected to XRPD. FIG. 12A provides XRPD pattern for Form 12 where no change to the polymorph was observed during drying. This crystalline polymorph was also characterized by TGA, DSC, and PLM. As shown by TGA and DSC data in FIG. 12B, Form 12 showed an endothermic peak at 152.8° C., and a weight loss of 15.8% up to 160° C. PLM images displayed Form 12 as irregular shaped birefringent crystals. Based on the results, Form 12 was considered to be anhydrate.

Example 18: Conversion Between Form 11 and Form 12

To determine the thermodynamic stability relationship between Form 11 and Form 12, slurry conversion experiments were conducted. Specifically, Form 12 (2.5 mg) was added to 1.0 mL of 4% dichloromethane at room temperature. After equilibrium for 1 hour, the suspensions were filtered to obtain a saturated solution Form 12. To the saturated solution of Form 11:Form 12 (1:1) was added. After stirring at room temperature for 30 minutes, the solids were isolated for XRPD analysis. Only Form 11 was observed as shown in FIG. 12C. As a result Form 11 was determined to be the more thermodynamically stable than Form 12 at room temperature. The pH of Form 11 solution (2.5 mg in 1 mL of 4% dichloromethane) and Form 12 solution (2.5 mg in 1 mL of 4% dichloromethane) was measured to be 8.25 and 7.98, respectively.

Example 19: Crystalline Polymorph Form 13

Figure 13A:
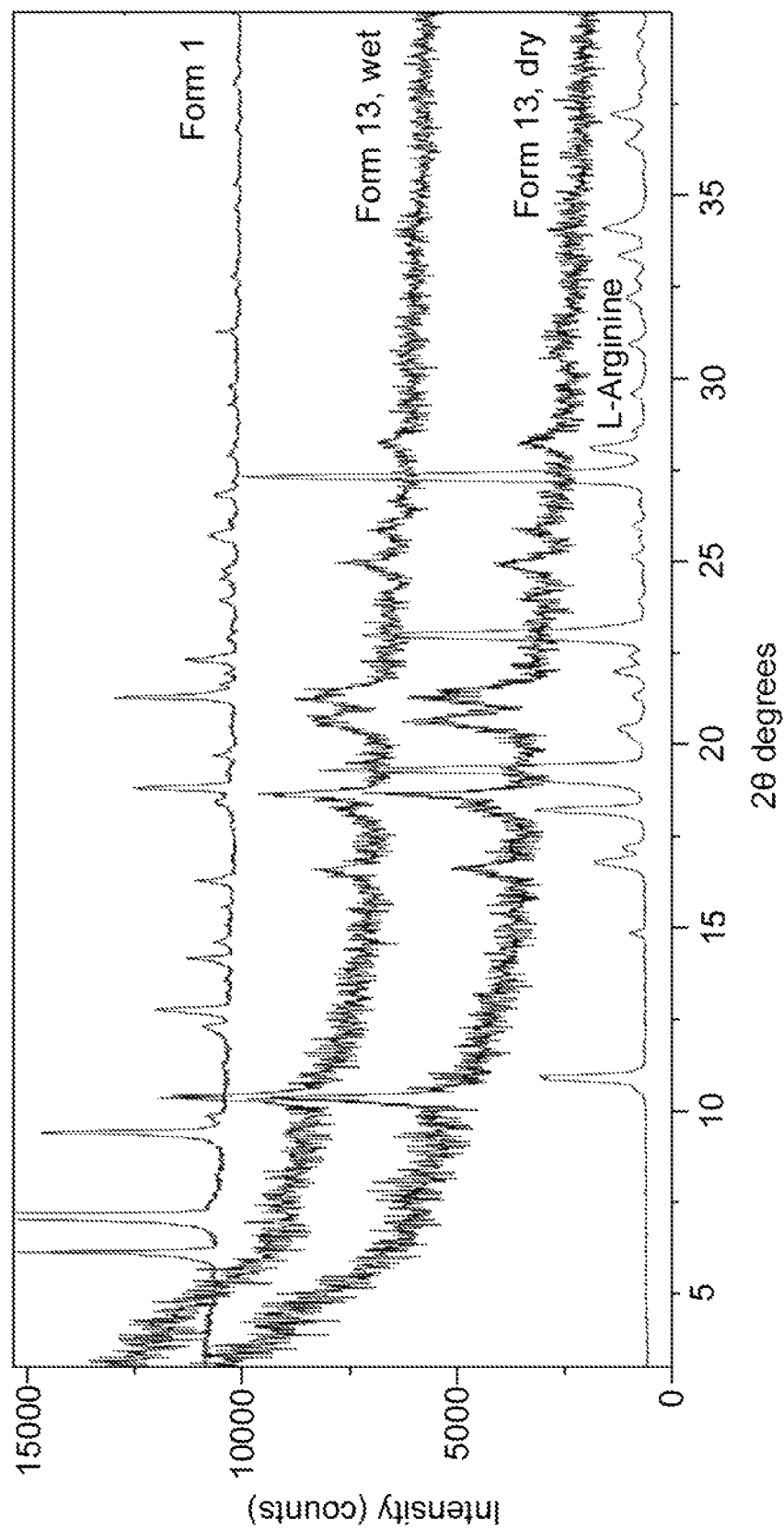
FIG. 13A shows a XRPD pattern for the crystalline polymorph Form 13 (Example 19).

A solution of crystalline polymorph Form 1 (20 mg in 0.3 mL) was mixed with 0.3 mL of a solution of L-arginine in methanol (1:1 molar ratio of L-arginine:Form 1), and then stirred for 2 to 5 days at room temperature. The solids were isolated and subjected to XRPD. The wet solids were also vacuum-dried at 50° C. for 2 hours, and then subjected to XRPD. FIG. 13A provides XRPD pattern for Form 13 where no change to the polymorph was observed during drying. This crystalline polymorph was also characterized by TGA, DSC, and PLM. As shown by TGA and DSC data in FIG. 13B, Form 13 showed endothermic peaks at 160.8° C. and 230.9° C., and a negligible weight loss before decomposition. PLM images showed Form 13 as plate-like birefringent crystals. Based on the results, Form 13 was considered to be anhydrate.

Example 20: Crystalline Polymorph Form 14

Figure 14A:
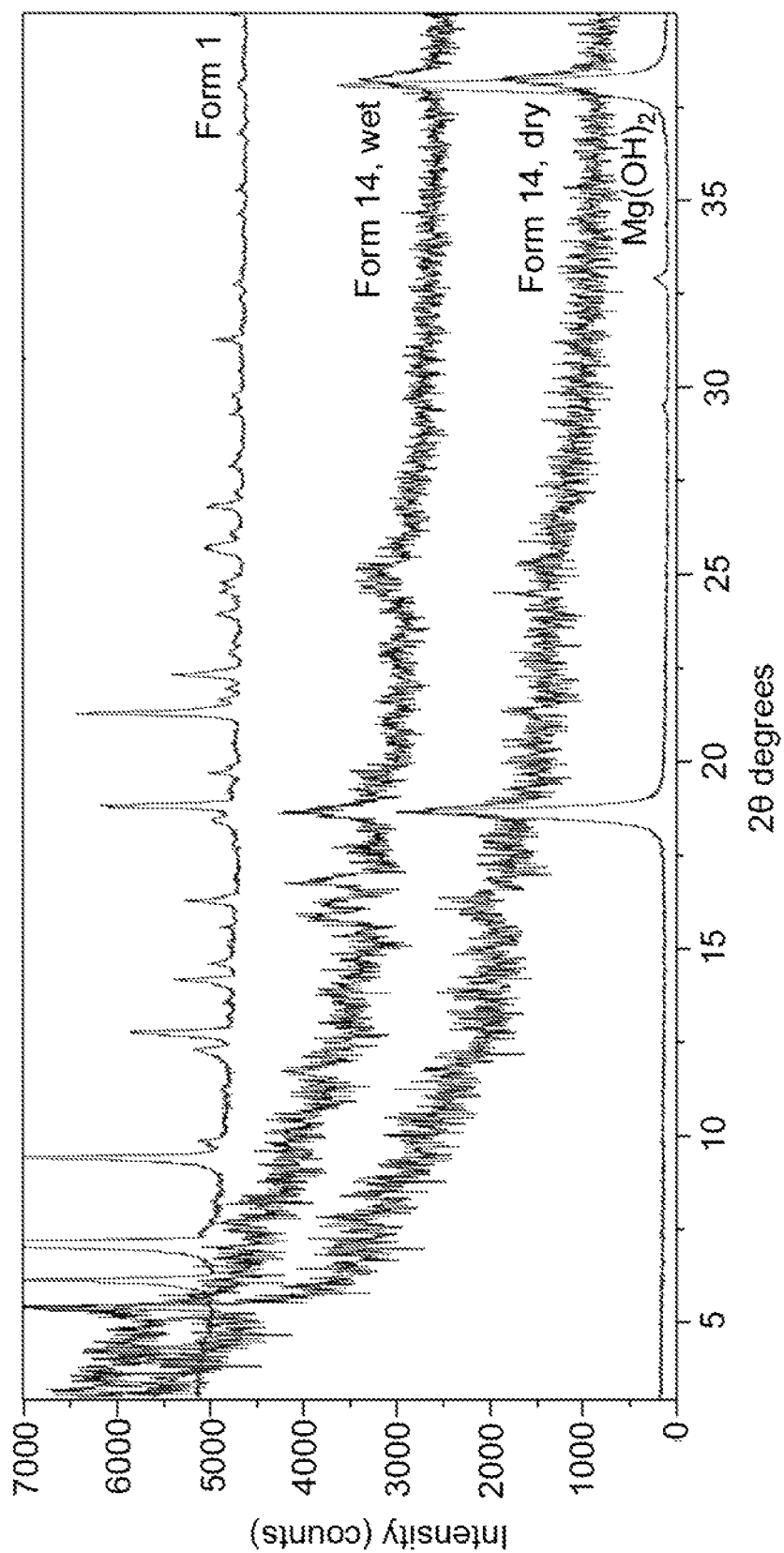
FIG. 14A shows a XRPD pattern for the crystalline polymorph Form 14 (Example 20).

A solution of crystalline polymorph Form 1 (20 mg in 0.3 mL) was mixed with 0.3 mL of a solution of Mg(OH)$_2$ in methanol (1:1 molar ratio of Mg(OH)$_2$:Form 1), and then stirred for 2 to 5 days at room temperature. The solids were isolated and subjected to XRPD. The wet solids were also vacuum-dried at 50° C. for 2 hours, and then subjected to XRPD. FIG. 14A provides XRPD pattern for Form 14 where no change to the polymorph was observed during drying. This crystalline polymorph was also characterized by TGA, DSC, and PLM. As shown by TGA and DSC data in FIG. 14B, Form 14 showed endothermic peaks at 104.5° C. and 137.2° C., and a weight loss of 5.8% up to 120° C. PLM images showed Form 14 as irregular shaped birefringent crystals. Based on the results, Form 14 was considered to be a hydrate or a solvate.

Example 21: Crystalline Polymorph Form 15

Figure 15A:
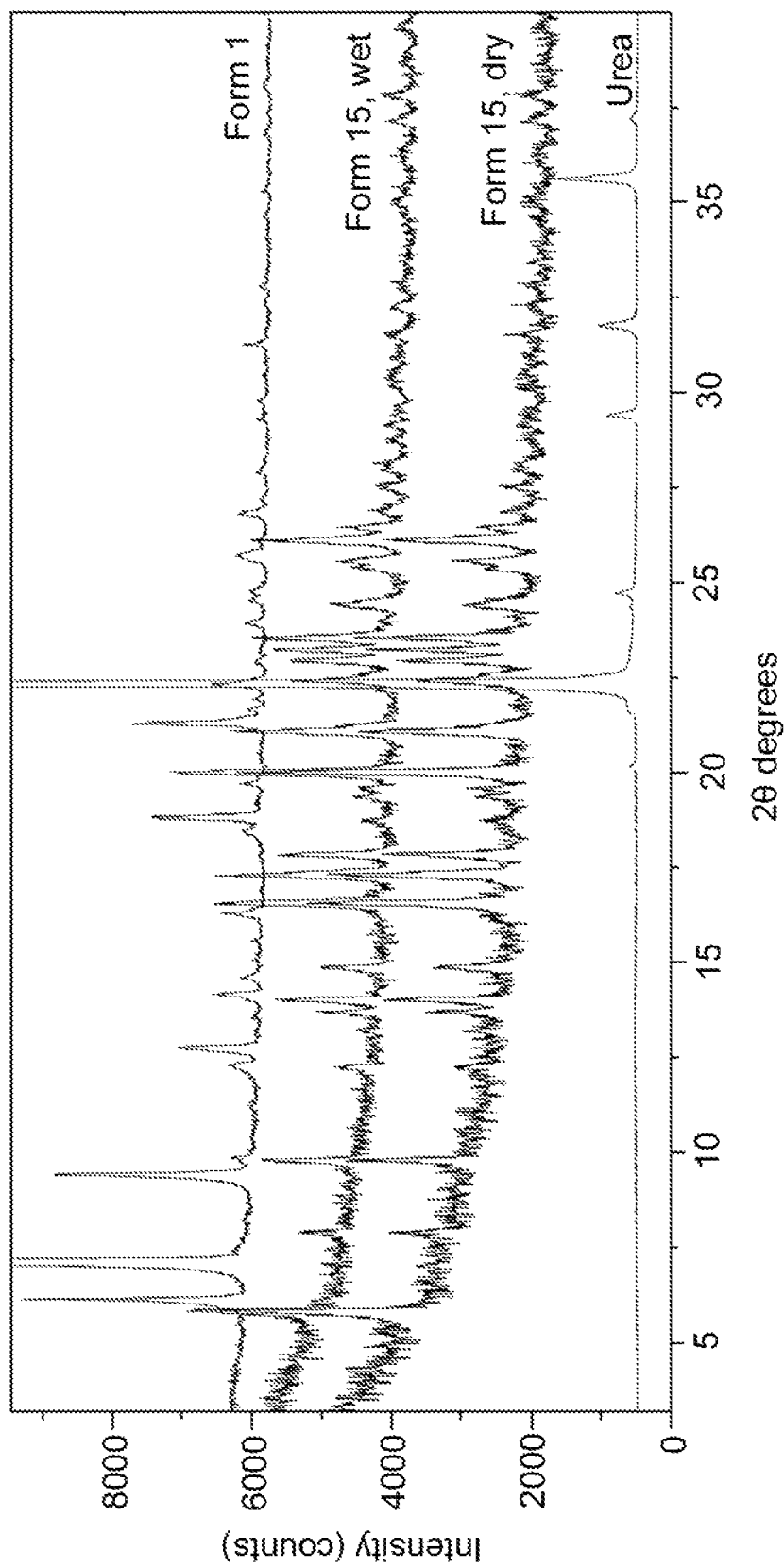
FIG. 15A shows a XRPD pattern for the crystalline polymorph Form 15 (Example 21).

A solution of crystalline polymorph Form 1 (20 mg in 0.3 mL) was mixed with 0.3 mL of a solution of urea in methanol (1:1 molar ratio of urea:Form 1), and then stirred for 2 to 5 days at room temperature. The solids were isolated and subjected to XRPD. The wet solids were also vacuum-dried at 50° C. for 2 hours, and then subjected to XRPD. FIG. 15A provides XRPD pattern for Form 15 where no change to the polymorph was observed during drying. This crystalline polymorph was also characterized by TGA, DSC, and PLM. As shown by TGA and DSC data in FIG. 15B, Form 15 showed an endothermic peak at 136.0° C., and negligible weight loss before decomposition. PLM images showed Form 15 as irregular shaped birefringent crystals. Based on the results, Form 15 was considered to be anhydrate.

Example 22: Crystalline Polymorph Form 16

Figure 16A:
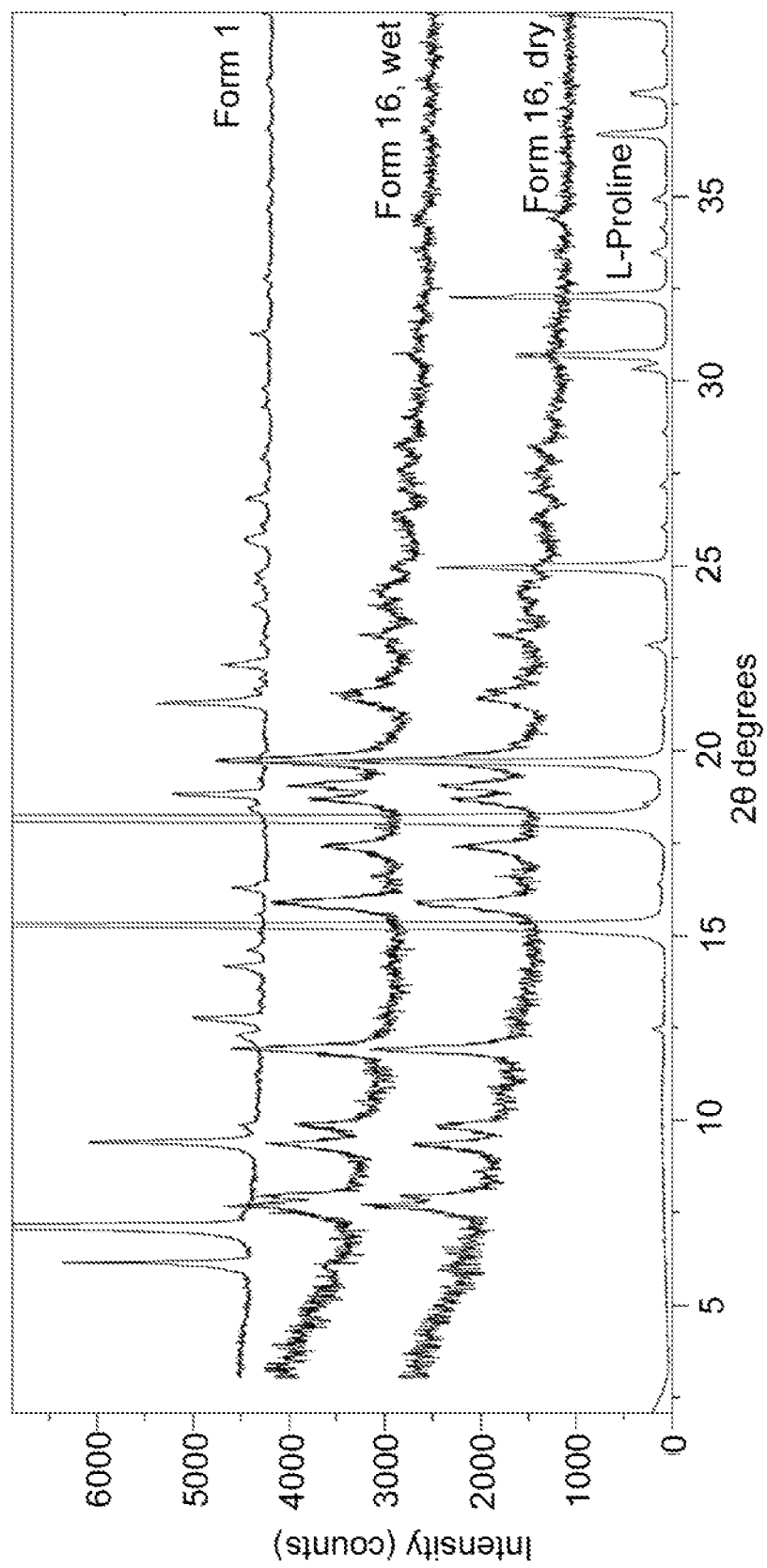
FIG. 16A shows a XRPD pattern for the crystalline polymorph Form 16 (Example 22).

A solution of crystalline polymorph Form 1 (20 mg in 0.3 mL) was mixed with 0.3 mL of a solution of Mg(OH)$_2$ in methanol (1:1 molar ratio of Mg(OH)$_2$:Form 1), and then stirred for 2 to 5 days at room temperature. The solids were isolated and subjected to XRPD. The wet solids were also vacuum-dried at 50° C. for 2 hours, and then subjected to XRPD. FIG. 16A provides XRPD pattern for Form 16 where no change to the polymorph was observed during drying. This crystalline polymorph was also characterized by TGA, DSC, and PLM. As shown by TGA and DSC data in FIG. 16B, Form 16 showed an endothermic peak at 168.3° C., and a weight loss of 1.0% up to 170° C. PLM images showed Form 16 as irregular shaped birefringent crystals. Based on the results, Form 16 was considered to be a hydrate or a solvate.

General Methodology and Instruments for Examples 2-22

X-Ray Powder Diffraction was obtained by standard techniques using Panalytical X'Pert3 Powder XRPD on a Si zero-background holder operating with a Cu Kα radiation source at 45 kV, 40 mA (Kα1 (Å): 1.540598, Kα2 (Å): 1.544426, Kα2/Kα1 intensity ratio: 0.50). The 2θ position was calibrated against Panalytical Si reference standard disc. The scanning parameters ranged from 3 to 40° 2θ (±0.0131°) and a continuous scan at a rate of about 0.04° 2θ/minute.

Thermogravimetric Analysis (TGA) and Differential Scanning Calorimetry (DSC) were obtained by standard techniques using TA Q500 or 0550 (for TGA) and TA Q2000 (for DSC), all from TA Instruments. DSC was calibrated with indium reference standard, and samples were analyzed using a temperature program from 25° C. to 350° C. at a rate of 10° C./minute. TGA was calibrated using nickel reference standard, and samples were analyzed using a temperature program from 25° C. to 350° C. at a rate of 10° C./minute.

Polarized Light Microscopic (PLM) image was captured on Nikon DS-Fi2 upright microscope at room temperature.

Dynamic Vapor Sorption (DVS) was measured with a SMS DVS Intrinsic from Surface Measurement Systems (London, United Kingdom) using the following parameters: temperature: 25° C.; sample size: 10-20 mg; gas and flow rate: $N_2$ and 200 mL/min; dm/dt: 0.002%/min; min. dm/dt stability duration: 10 min; max. equilibrium time: 180 min; relative humidity (RH) range: 0% RH-95% RH-0% RH; RH step size: 10%.

Fourier-transform infrared spectroscopy (FTIR) spectral data as disclosed herein was obtained by standard techniques using Shimadzu FTIR spectrometer in attenuated total reflectance (ATR) mode operating at a total of 20 scans with a resolution of 2 $cm^{-1}$.

Biological Example 1: Cell Viability of BJAB Cells

BJAB cells (DSMZ) are maintained in RPMI 1640 growth medium+10% FBS at 37° C./5% $CO_2$ and used prior to passage 34. Cells are seeded in white Corning Costar 96-well assay plates at 2500 cells/well in 50 µL of medium. Serial dilutions of test crystalline polymorph compounds are made in cell culture medium/FBS+0.2% DMSO, and transferred to assay plates in a volume of 50 µL (DMSO at 0.1% final). Plates are maintained at 37° C. for approximately 72 hours. The effect of compounds on cell proliferation is evaluated using the Cell Titer Glo reagent (Promega), according to the manufacturer's instructions. Briefly, 100 µL of reagent is added per well, and after a 10 minute incubation luminescence values are determined on a plate reader (Tecan F200PRO). The percent of luminescence signal relative to untreated controls is calculated for each compound concentration, and $EC_{50}$ values are determined from dose response data by non-linear regression analysis using Prism (Graph-Pad). Data are shown in the compound table above. The mTor inhibitor Torin1 (Liu, et al. (2010) J. Med. Chem. 53, 7146.) is used as a control. The data are summarized in the compound table provided above.

Biological Example 2: Measurement of Glutathione Levels Following Treatment Using Three Cell Lines BJAB, HCT116, and normal human lung fibroblasts (NHLF) are maintained in RPMI (Wisent), McCoy's (Wisent) or FGM-2 (Lonza) medium, respectively. For total glutathione measurement, 5000 cells/well (BJAB or HCT116) or 10,000 cells/well (NHLF) are transferred to clear-bottom 96-well assay plates (Thermo Fisher) in a volume of 50 µL. Plates are incubated overnight at 37° C. in 5% $CO_2$, in an unsealed plastic bag with damp paper. Test crystalline polymorph compound is serially diluted in medium plus 0.4% DMSO, and 50 µL/well of each dilution is transferred to the assay plate. Assay plates are incubated at 37° C. in 5% $CO_2$ in unsealed plastic bag with damp paper for the indicated time. For total glutathione measurement, GSH-Glo™ reagent (Promega) is prepared by diluting provided Luciferin-NT (1:100), Glutathione S-Transferase (1:100), and DTT (1 mM final) to GSH-Glo™ Reaction buffer, and 100 µL is added to assay plates, followed by 30 min incubation at room temperature, and then 100 µL Luciferin Detection Reagent is added. Plates are maintained in the dark at room temperature for 10 min. Luminescence is measured using Tecan Infinite 200Pro.

Biological Example 3: Cell Cycle Analysis of Treated Cells

HCT116 cells ($3\times10^5$ cells) grown in McCoy media supplemented with heat inactivated fetal bovine serum are plated in 6-well plates and allowed to adhere overnight. Duplicate samples are prepared by treating cells for 24 hours with serum starvation (0% FBS), 5 µM test crystalline polymorph compound or DMSO vehicle control. Two hours prior to harvest, replicating DNA is labeled with EdU (5-Ethynyl-2'-deoxyuridine, Thermo Fisher) at 10 µM. Both adherent and floating cells are harvested and fixed in a solution of 4% paraformaldehyde in PBS for 15 minutes at room temperature. Next, cells are permeabilized in a solution of 0.25% v/v triton X-100/0.5% BSA/PBS for 20 minutes at room temperature. This is followed by click reaction with OG488-Azide to detect EdU incorporation as follows: cells are incubated for 30 minutes in a reaction mixture containing 100 mM Tris-HCl pH 7.6, 4 mM $CuSO_4$, 10 µM OG488-azide, and 100 mM ascorbic acid. Excess reagent is removed by repeated washes in 0.5% BSA/PBS wash buffer. Cells are re-suspended in 500 µL of DAPI staining solution (1 µg/mL DAPI and 50 µg/mL RNAse A in PBS).

Flow cytometry analysis is performed in a LSRII flow cytometer (BD Biosciences) equipped with blue (488 nm), red (633 nm), and violet (405 nm) lasers. OG488 analysis is performed using 488 nm excitation and detection with a 505LP mirror and a 530/30BP filter. DAPI analysis is performed using a 405 nm excitation and detection with a 442/16BP filter. Voltage settings are: FSC=324, SSC=276, OG488=215, DAPI=351. Cell cycle analysis with DAPI is performed using a linear axis scale. Log scale is used for EdU. Data analysis is performed using FCS Express software version 6 (DeNovo Software).

Various exemplary embodiments of the disclosure include, but are not limited to the enumerated embodiments listed below, which can be combined in any number and in any combination that is not technically or logically inconsistent.

Embodiment 1

A crystalline polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid, optionally in the form of a hydrate or solvate thereof.

Embodiment 2

The crystalline polymorph of embodiment 1, in the form of an anhydrate/ansolvate.

Embodiment 3

The crystalline polymorph of embodiment 1 or embodiment 2, characterized in that it provides an X-ray powder diffraction (XRPD) pattern comprising four or more (e.g., five or more) peaks selected from: 6.1, 7.1, 9.4, 12.7, 18.8, 21.3, and 22.3 (2θ±0.1 degrees).

Embodiment 4

The crystalline polymorph of embodiment 1 or embodiment 2, characterized in that it provides a XRPD pattern comprising six or more (e.g., each of the) peaks selected from: 6.1, 7.1, 9.4, 12.7, 18.8, 21.3, and 22.3 (2θ±0.1 degrees).

Embodiment 5

The crystalline polymorph of any of embodiments 1-4, characterized in that it provides a XRPD pattern in accordance with that shown in FIG. 1A.

Embodiment 6

The crystalline polymorph of any of embodiments 1-5, characterized in that it provides a differential scanning calorimetry (DSC) thermogram having an endothermic peak at 123±2° C.

Embodiment 7

Figure 1B:
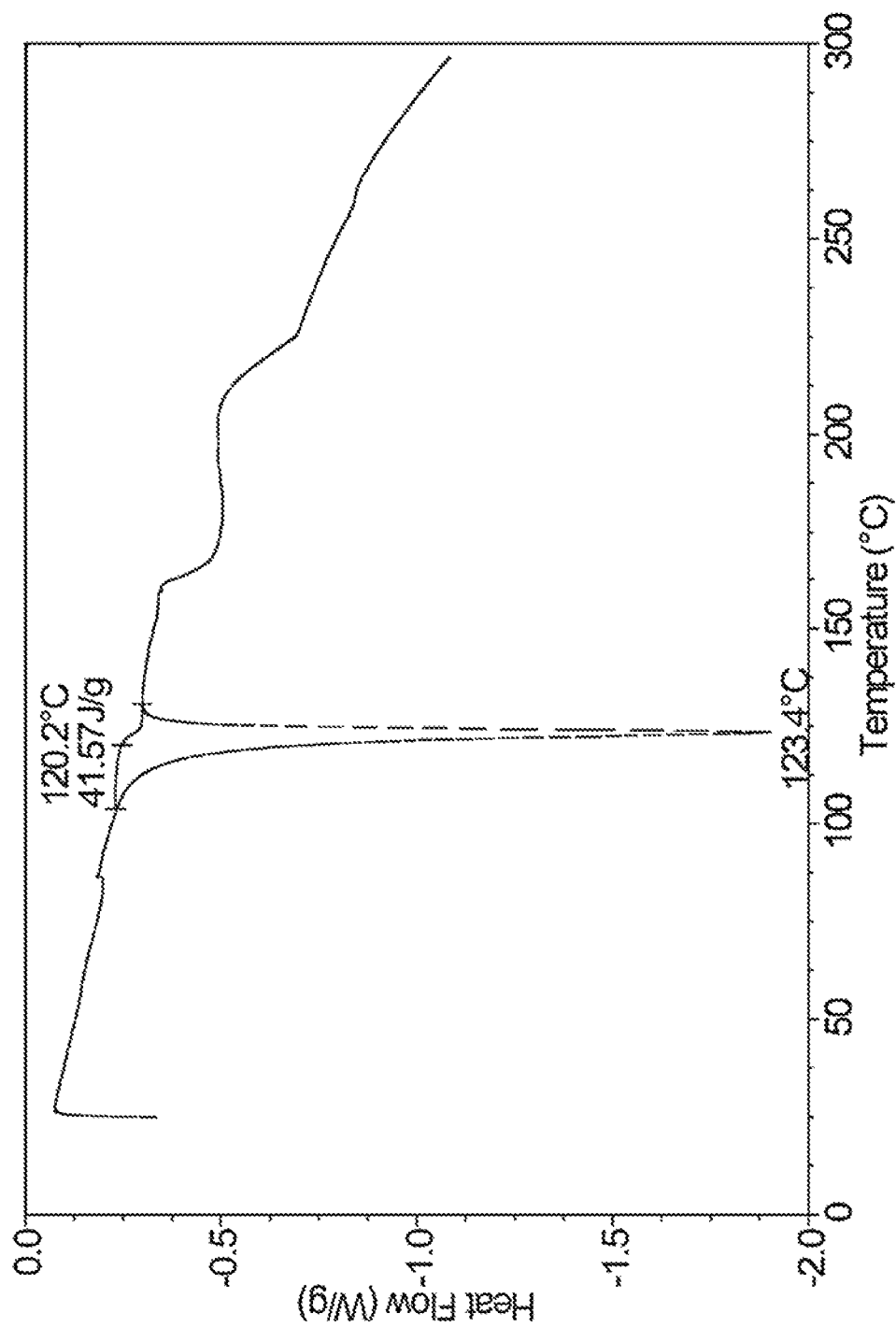
Figure 1D:
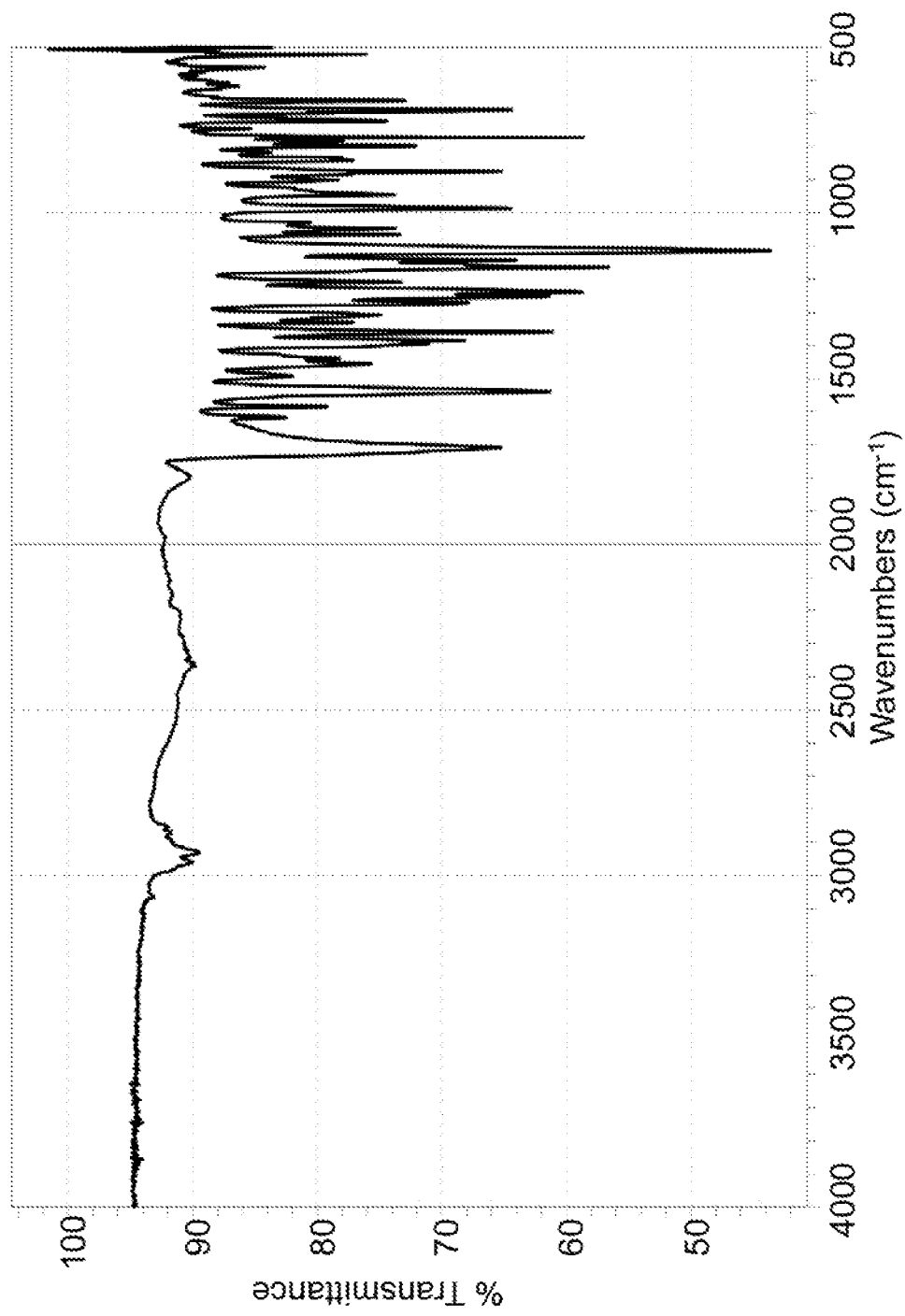
FIG. 1D shows a Fourier-transform infrared (FTIR) spectrum for the crystalline polymorph Form 1.
Figure 1F:
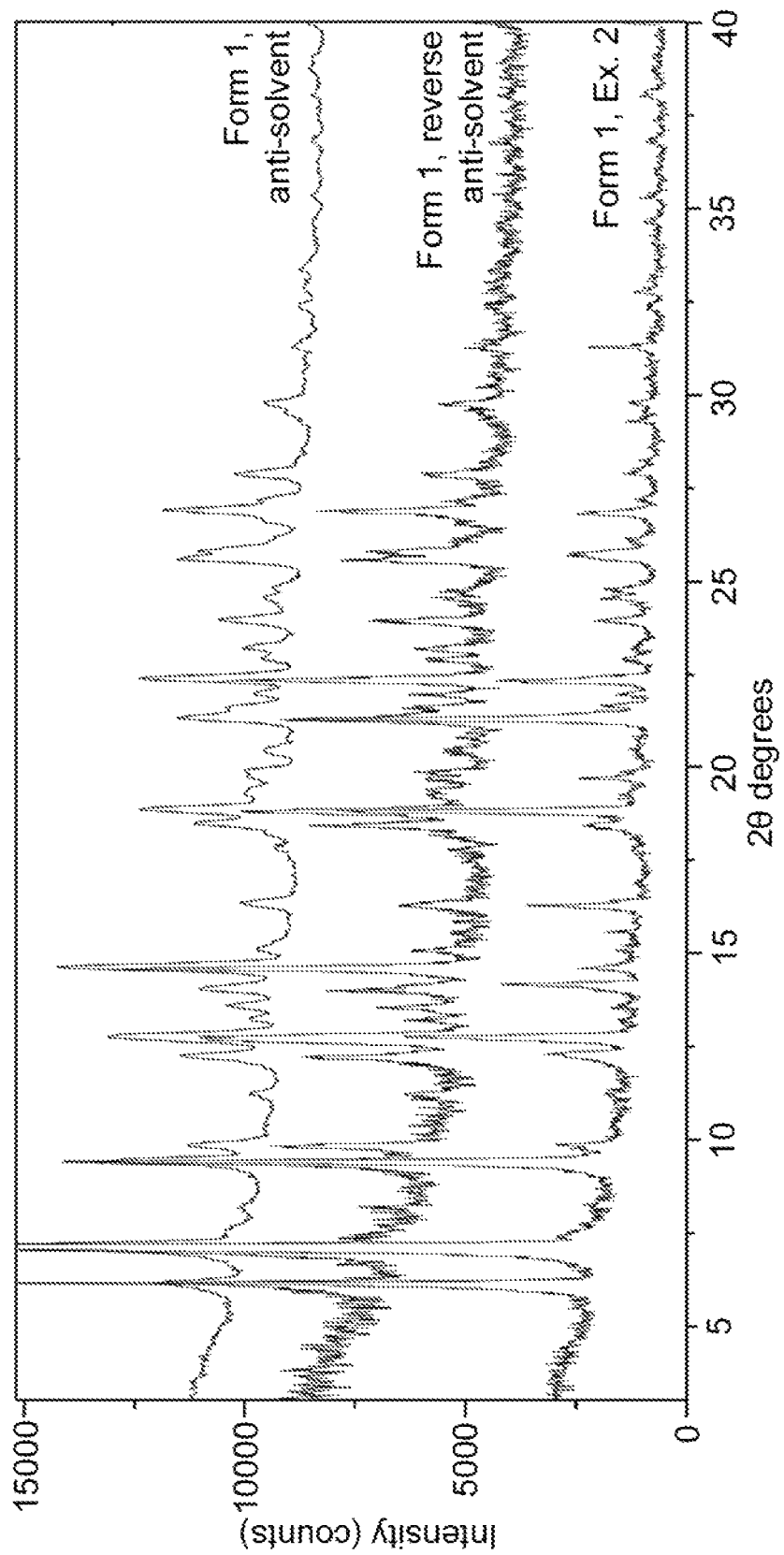
FIG. 1F shows an overlay of the XRPD pattern of Form 1 of Example 1 and two crystalline forms obtained after recrystallization in Example 3.

The crystalline polymorph of any of embodiments 1-6, characterized in that it provides a DSC thermogram in accordance with that shown in FIG. 1B.

Embodiment 8

The crystalline polymorph of any of embodiments 1-7, characterized in that it provides a Fourier-transform infrared spectroscopy (FTIR) spectrum comprising six or more (e.g., seven or more, or eight or more, or nine or more) peaks selected from: 2930 (broad) ±2 cm$^1$, 1709±2 cm$^{-1}$, 1539±2 cm$^1$, 1359±2 cm$^{-1}$, 1238±2 cm$^{-1}$, 1165±2 cm$^1$, 1112±2 cm$^{-1}$, 987±2 cm$^1$, 875±2 cm$^{-1}$, 772.50±2 cm$^{-1}$, and 690±2 cm$^{-1}$.

Embodiment 9

The crystalline polymorph of any of embodiments 1-7, characterized in that it provides a FTIR spectrum in accordance with that shown in FIG. 1D.

Embodiment 10

The crystalline polymorph of embodiment 1 or embodiment 2, characterized in that it provides a XRPD pattern comprising four or more (e.g., five or more) peaks selected from: 6.2, 6.6, 7.5, 10.9, 12.4, and 13.3 (2θ±0.1 degrees).

Embodiment 11

The crystalline polymorph of embodiment 1 or embodiment 2, characterized in that it provides a XRPD pattern comprising each of the peaks: 6.2, 6.6, 7.5, 10.9, 12.4, and 13.3 (2θ±0.1 degrees).

Embodiment 12

Figure 2:
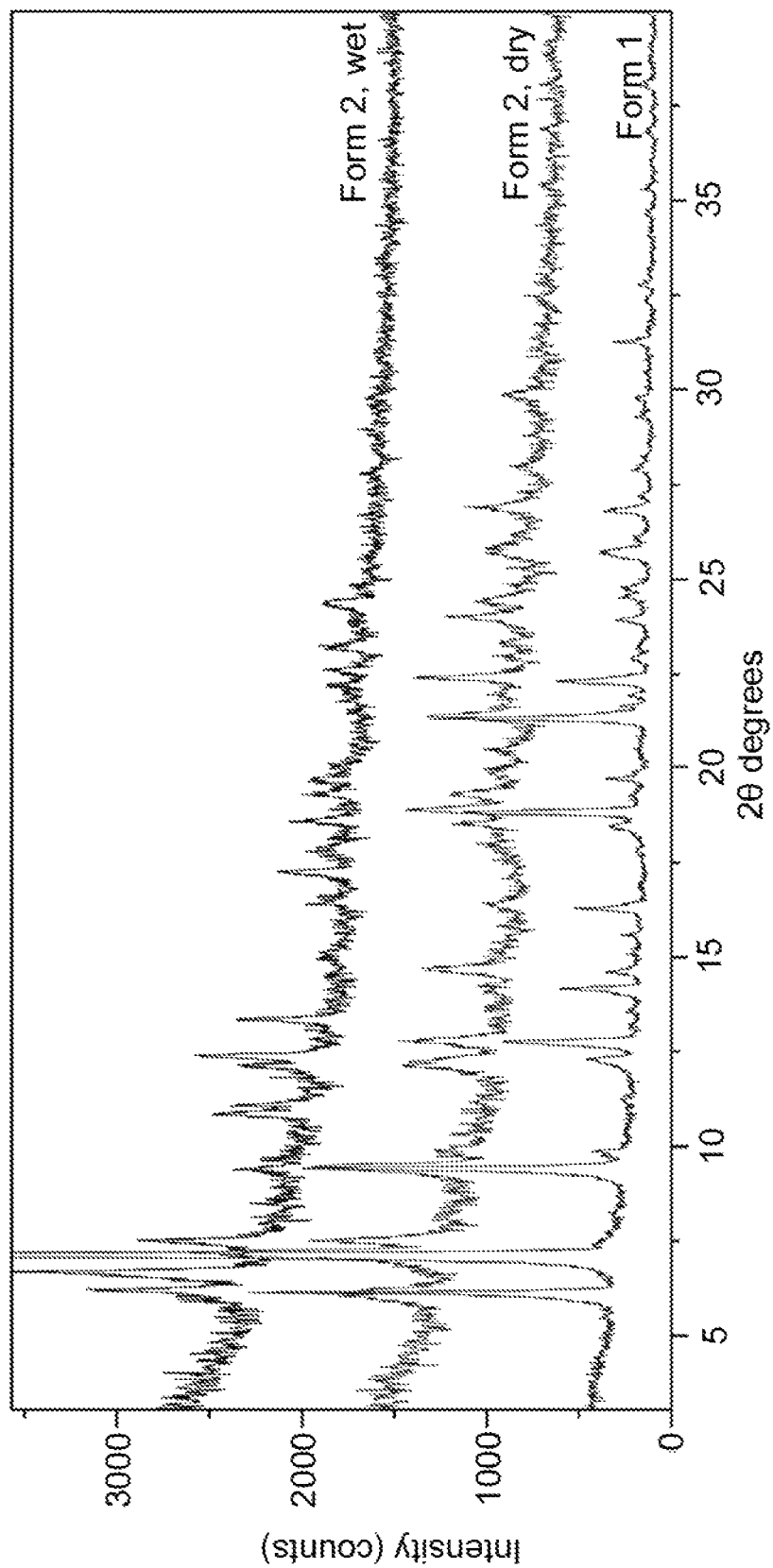
FIG. 2 shows a XRPD pattern for the crystalline polymorph Form 2 (Example 5).

The crystalline polymorph of any of embodiments 1, 2, 10 and 11, characterized in that it provides a XRPD pattern in accordance with that shown in FIG. 2.

Embodiment 13

The crystalline polymorph of embodiment 1 or embodiment 2 characterized in that it provides a XRPD pattern comprising four or more (e.g., five or more) peaks selected from: 6.4, 7.1, 17.7, 18.8, 19.3, and 22.5 (2θ±0.1 degrees).

Embodiment 14

The crystalline polymorph of embodiment 1 or embodiment 2, characterized in that it provides a XRPD pattern comprising each of the peaks: 6.4, 7.1, 17.7, 18.8, 19.3, and 22.5 (2θ±0.1 degrees).

Embodiment 15

The crystalline polymorph of any of embodiments 1, 2, 13 and 14, characterized in that it provides a XRPD pattern in accordance with that shown in FIG. 5A.

Embodiment 16

The crystalline polymorph of any of embodiments 1, 2 and 13-15, characterized in that it provides a DSC thermogram having an endothermic peak at 142±2° C.

Embodiment 17

Figure 5B:
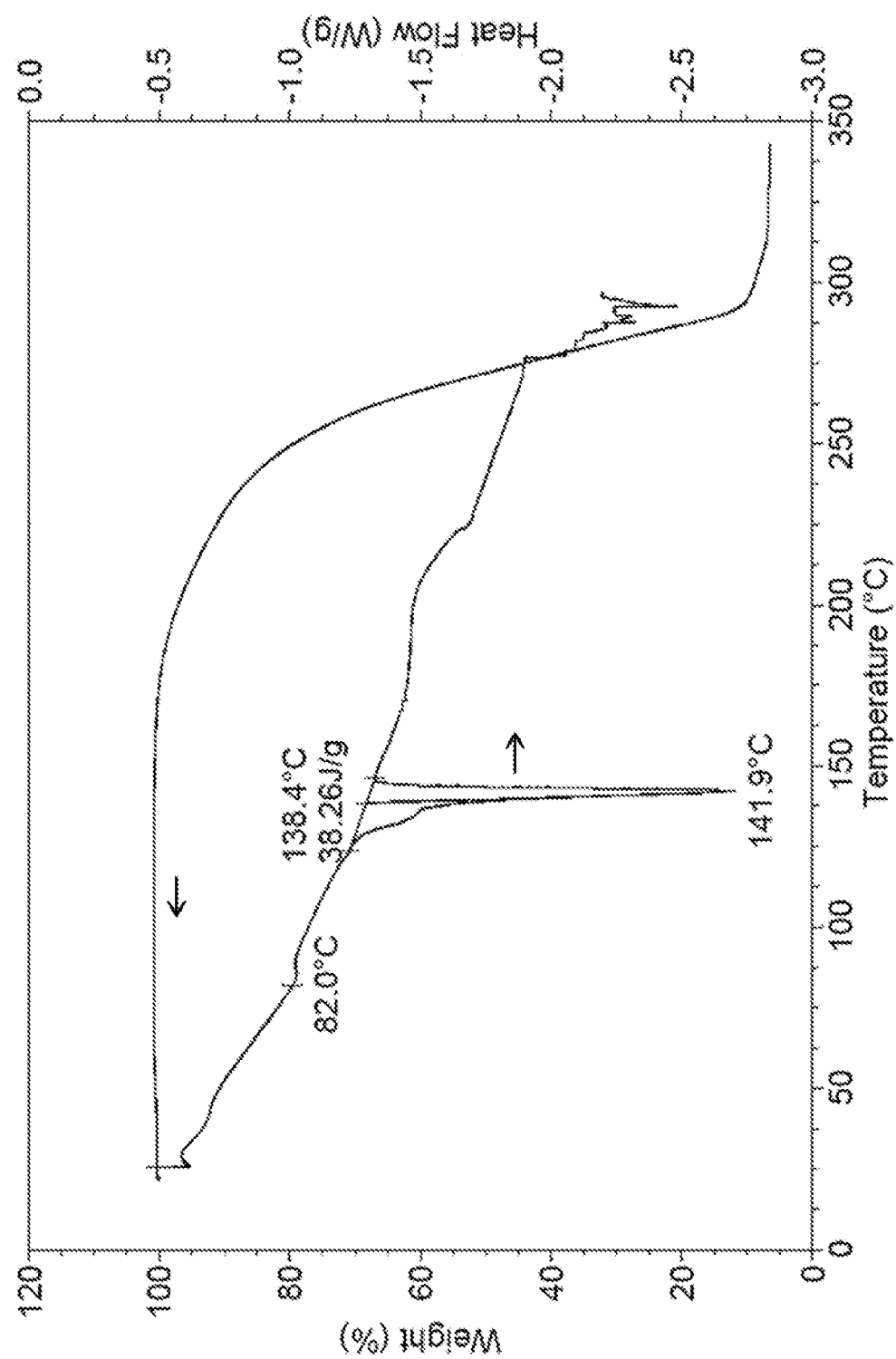
FIG. 5B shows a TGA and a DSC profile for the crystalline polymorph Form 5.
Figure 5C:
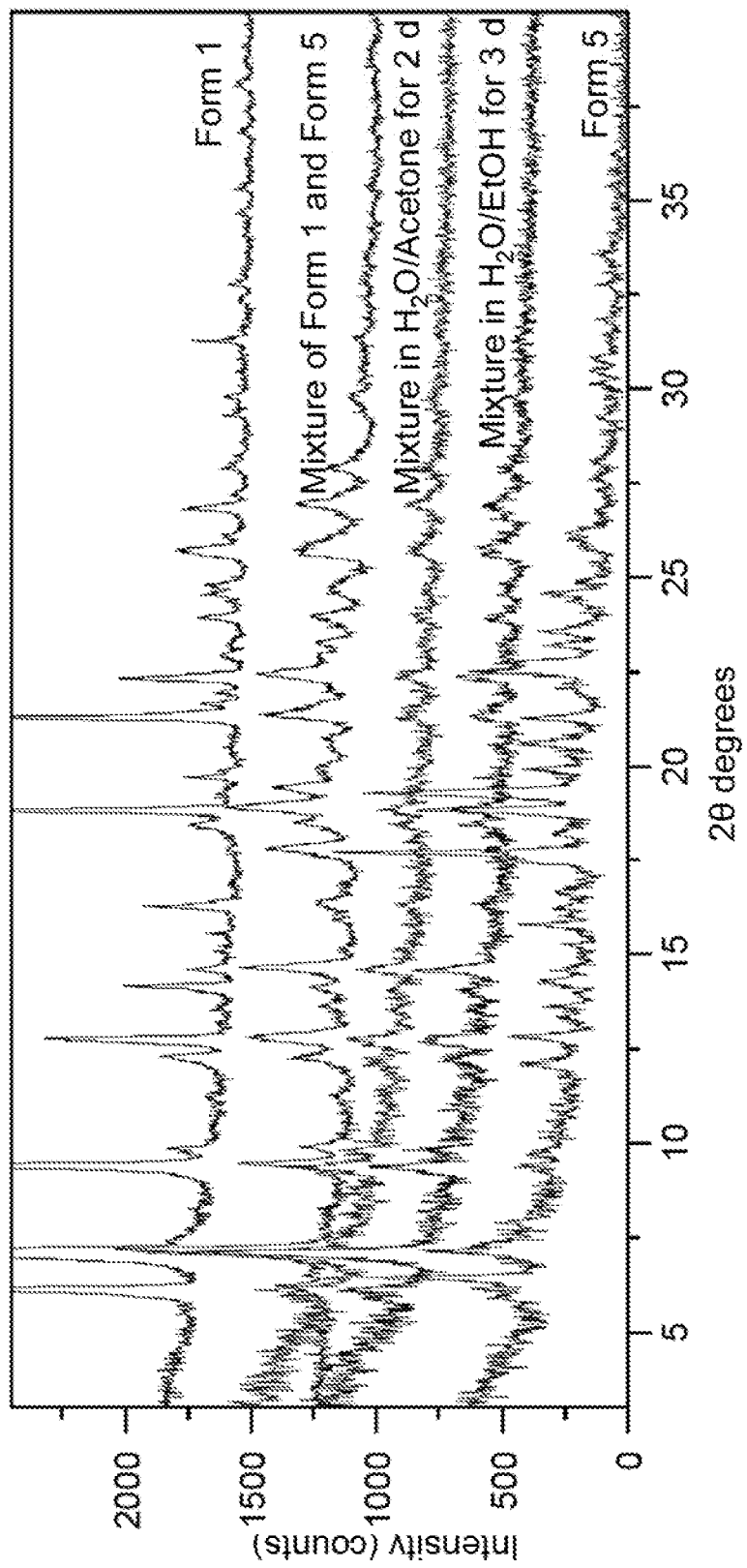
FIG. 5C shows an overlay of the XRPD pattern of competitive experiments between Form 1 and Form 5.

The crystalline polymorph of any of embodiments 1, 2 and 13-16, characterized in that it provides a DSC thermogram in accordance with that shown in Figure 5B.

Embodiment 18

The crystalline polymorph of embodiment 1 or embodiment 2, characterized in that it provides a XRPD pattern comprising four or more (e.g., five or more) peaks selected from: 6.4, 9.1, 14.3, 16.6, 18.4, 20.1, and 21.9 (2θ±0.1 degrees).

Embodiment 19

The crystalline polymorph of embodiment 1 or embodiment 2, characterized in that it provides a XRPD pattern comprising each of the peaks: 6.4, 9.1, 14.3, 16.6, 18.4, 20.1, and 21.9 (2θ±0.1 degrees).

Embodiment 20

Figure 8:
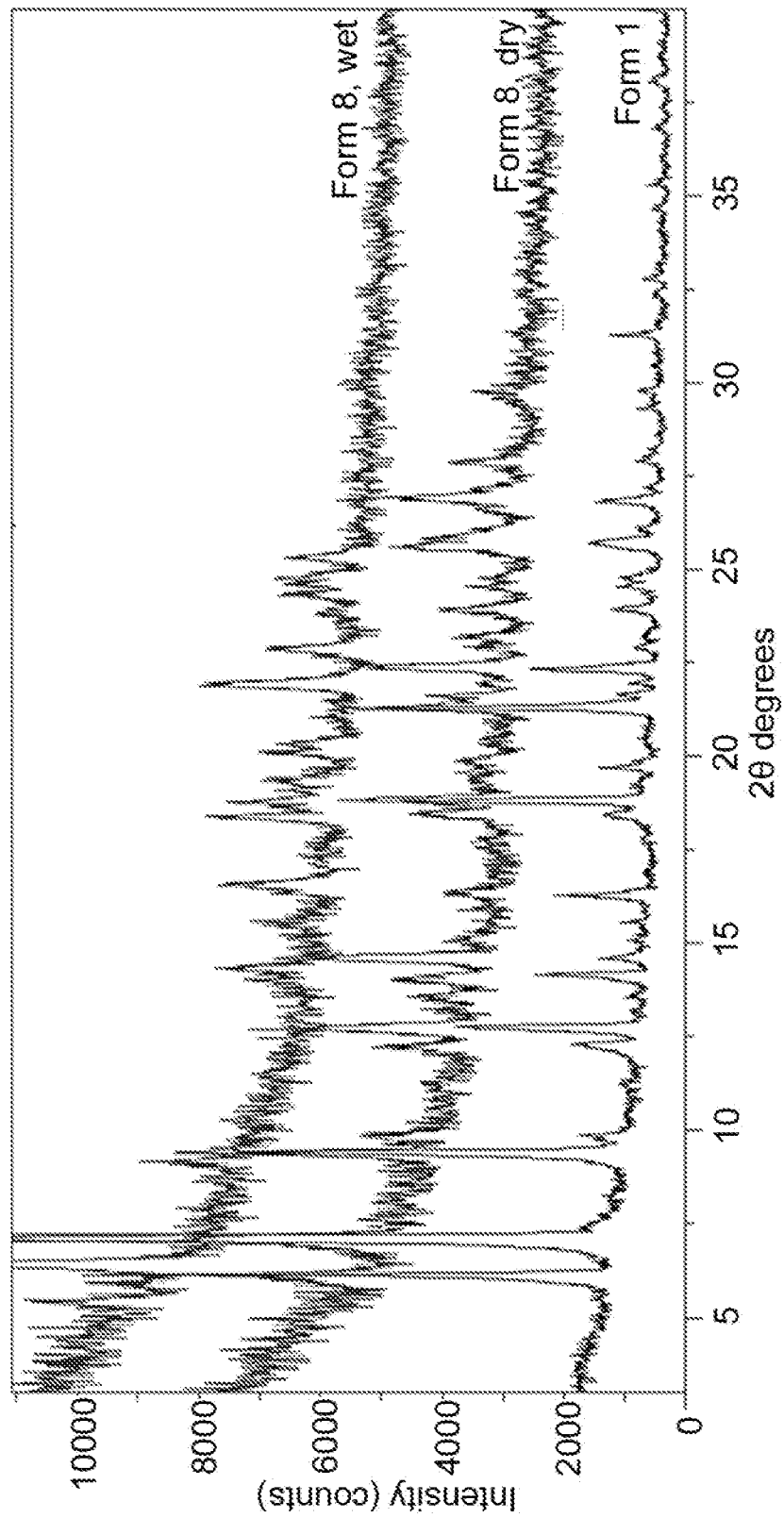
FIG. 8 shows a XRPD pattern for the crystalline polymorph Form 8 (Example 12).

The crystalline polymorph of any of embodiments 1, 2, 18 and 19, characterized in that it provides a XRPD pattern in accordance with that shown in FIG. 8.

Embodiment 21

The crystalline polymorph of embodiment 1, which is in the form of a hydrate or solvate of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid.

Embodiment 22

The crystalline polymorph of embodiment 21, characterized in that it provides a XRPD pattern comprising four or more (e.g., five or more) peaks selected from: 6.4, 14.4, 16.2, 17.5, 19.1, 22.8, and 24.0 (2θ±0.1 degrees).

Embodiment 23

The crystalline polymorph of embodiment 21, characterized in that it provides a XRPD pattern comprising six or more (e.g., each of the) peaks selected from: 6.4, 14.4, 16.2, 17.5, 19.1, 22.8, and 24.0 (2θ±0.1 degrees).

Embodiment 24

The crystalline polymorph of any of embodiments 21-23, characterized in that it provides a XRPD pattern in accordance with that shown in FIG. 3A.

Embodiment 25

The crystalline polymorph of any of embodiments 21-24, characterized in that it provides a DSC thermogram having endothermic peaks at 91±2° C. and 118±2° C.

Embodiment 26

The crystalline polymorph of any of embodiments 21-25, characterized in that it provides a DSC thermogram in accordance with that shown in FIG. 3B.

Embodiment 27

The crystalline polymorph of embodiment 21, characterized in that it provides a XRPD pattern comprising four or more (e.g., five or more) peaks selected from: 9.9, 14.9, 19.4, 21.4, 23.5, and 24.1 (2θ±0.1 degrees).

Embodiment 28

The crystalline polymorph of embodiment 21, characterized in that it provides a XRPD pattern comprising each of the peaks: 9.9, 14.9, 19.4, 21.4, 23.5, and 24.1 (2θ±0.1 degrees).

Embodiment 29

The crystalline polymorph of any of embodiments 21, 27 and 28, characterized in that it provides a XRPD pattern in accordance with that shown in FIG. 4A.

Embodiment 30

The crystalline polymorph of any of embodiments 21 and 27-29, characterized in that it provides a DSC thermogram having endothermic peaks at 49±2° C. and 73±2° C.

Embodiment 31

Figure 4B:
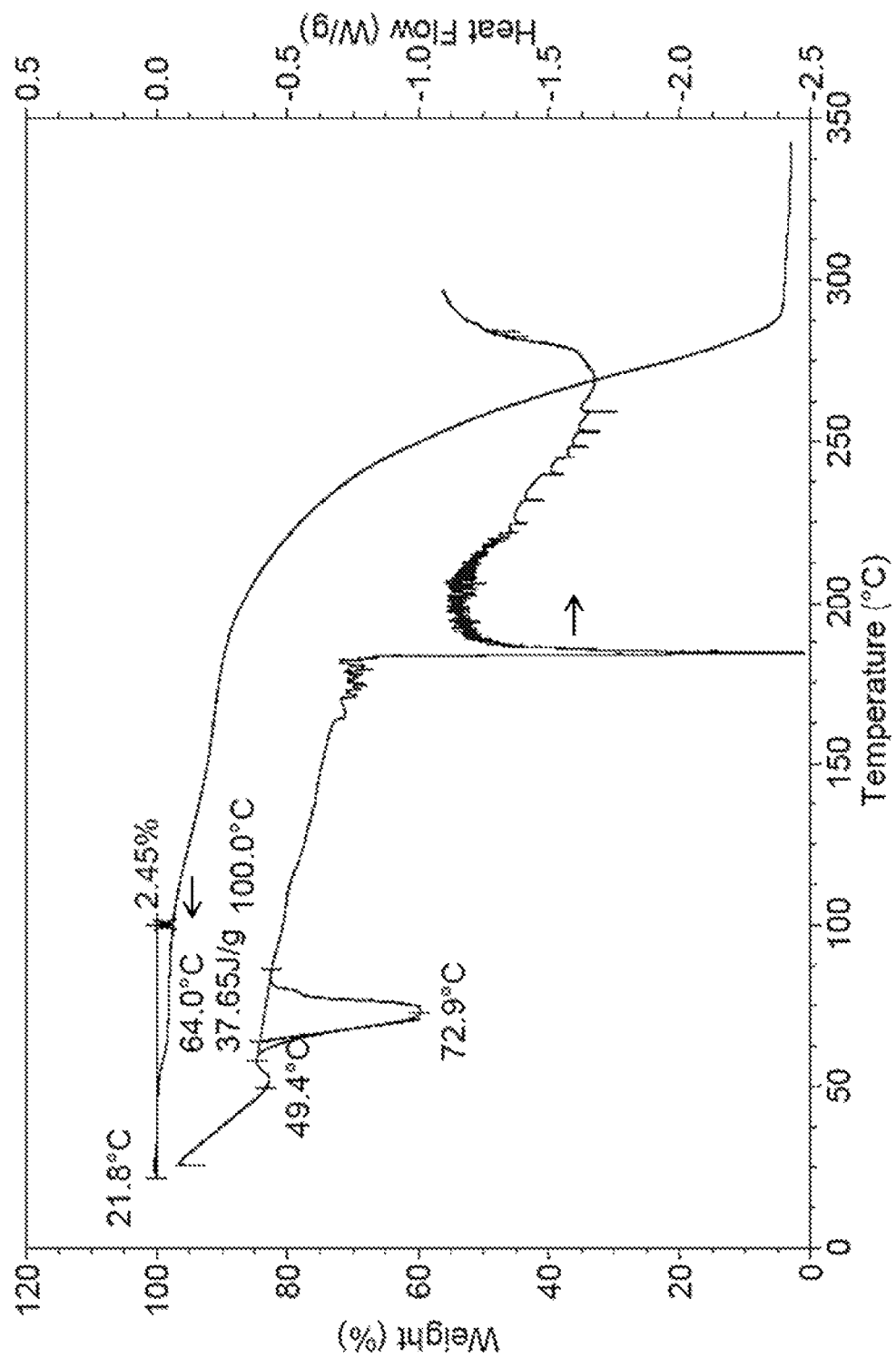
FIG. 4B shows a TGA and a DSC profile for the crystalline polymorph Form 4.

The crystalline polymorph of any of embodiments 21 and 27-30, characterized in that it provides a DSC thermogram in accordance with that shown in FIG. 4B.

Embodiment 32

The crystalline polymorph of embodiment 21, characterized in that it provides a XRPD pattern comprising four or more (e.g., five or more) peaks selected from: 5.8, 11.5, 14.5, 17.3, 20.8, and 22.0 (2θ±0.1 degrees).

Embodiment 33

The crystalline polymorph of embodiment 21, characterized in that it provides a XRPD pattern comprising each of the peaks: 5.8, 11.5, 14.5, 17.3, 20.8, and 22.0 (2θ±0.1 degrees).

Embodiment 34

The crystalline polymorph of any of embodiments 21, 32 and 33, characterized in that it provides a XRPD pattern in accordance with that shown in FIG. 6A.

Embodiment 35

The crystalline polymorph of any of embodiments 21 and 32-34, characterized in that it provides a DSC thermogram having endothermic peaks at 64±2° C. and 120±2° C.

Embodiment 36

The crystalline polymorph of any of embodiments 21 and 32-35, characterized in that it provides a DSC thermogram in accordance with that shown in FIG. 6B.

Embodiment 37

The crystalline polymorph of embodiment 21, characterized in that it provides a XRPD pattern comprising four or more (e.g., five or more) peaks selected from: 6.7, 7.0, 11.5, 13.1, 14.4, 17.2 and 22.1 (2θ±0.1 degrees).

Embodiment 38

The crystalline polymorph of embodiment 21, characterized in that it provides a XRPD pattern comprising each of the peaks: 6.7, 7.0, 11.5, 13.1, 14.4, 17.2 and 22.1 (2θ±0.1 degrees).

Embodiment 39

The crystalline polymorph of any of embodiments 21, 37, and 38, characterized in that it provides a XRPD pattern in accordance with that shown in FIG. 7A.

Embodiment 40

The crystalline polymorph of any of embodiments 21 and 37-39, characterized in that it provides a DSC thermogram having endothermic peaks at 58±2° C. and 108±2° C.

Embodiment 41

Figure 7B:
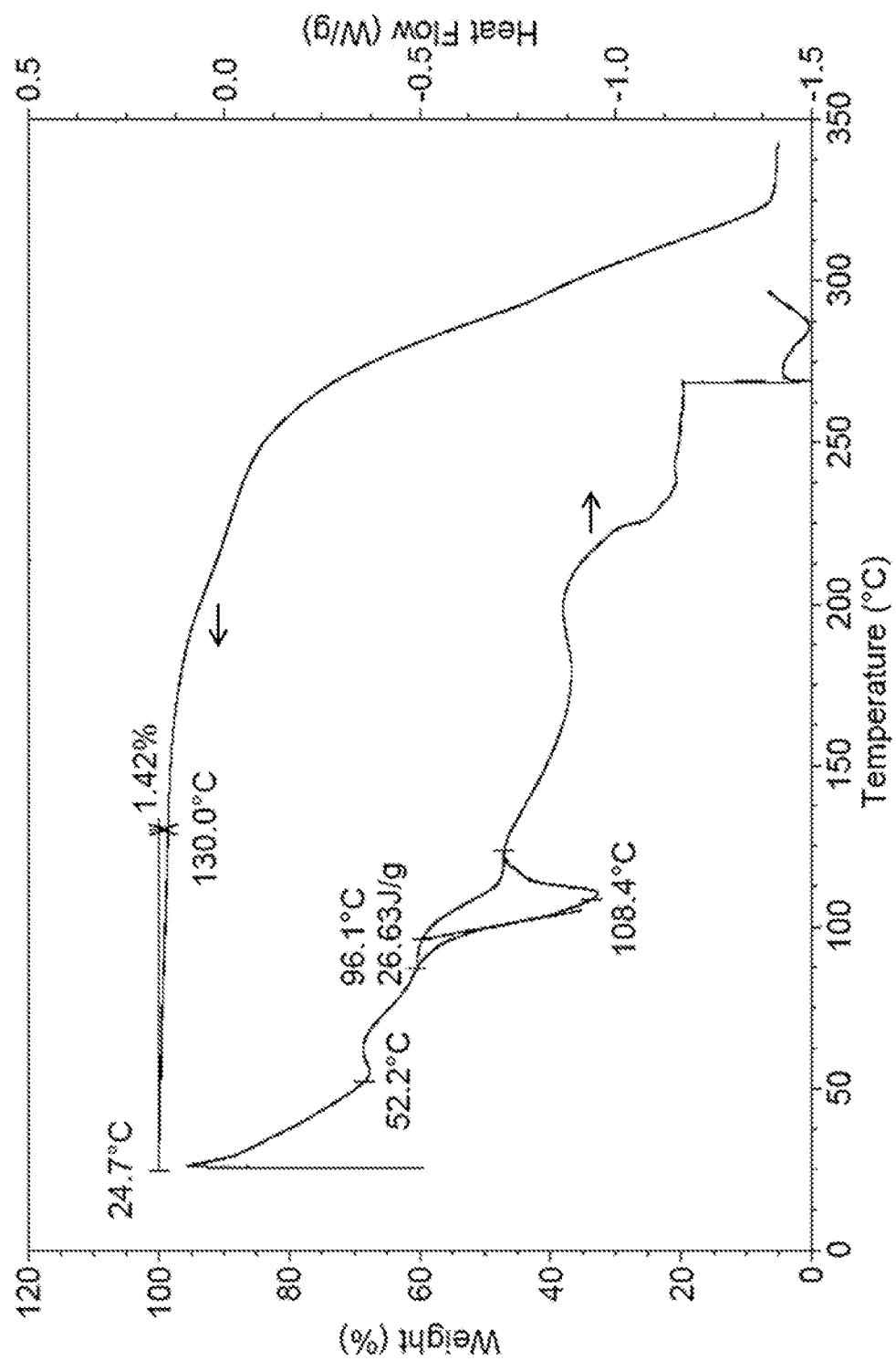
FIG. 7B shows a TGA and a DSC profile for the crystalline polymorph Form 7.

The crystalline polymorph of any of embodiments 21 and 37-40, characterized in that it provides a DSC thermogram in accordance with that shown in FIG. 7B.

Embodiment 42

A crystalline polymorph of potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

Embodiment 43

The crystalline polymorph of embodiment 42, characterized in that it provides a XRPD pattern comprising four or more (e.g., five or more) peaks selected from: 6.4, 7.1, 10.2, 12.2, 14.2, 19.0, 19.4, and 24.5 (2θ±0.1 degrees).

Embodiment 44

The crystalline polymorph of embodiment 42, characterized in that it provides a XRPD pattern comprising each of the peaks selected from: 6.4, 7.1, 10.2, 12.2, 14.2, 19.0, 19.4, and 24.5 (2θ±0.1 degrees).

Embodiment 45

The crystalline polymorph of any of embodiments 42-44, characterized in that it provides a XRPD pattern in accordance with that shown in FIG. 9A.

Embodiment 48

The crystalline polymorph of any of embodiments 42-45, characterized in that it provides a DSC thermogram having an endothermic peak at 113±2° C.

Embodiment 47

The crystalline polymorph of any of embodiments 42-46, characterized in that it provides a DSC thermogram in accordance with that shown in FIG. 9B.

Embodiment 48

The crystalline polymorph of embodiment 42, characterized in that it provides a XRPD pattern comprising four or more (e.g., five or more) peaks selected from: 5.6, 5.8, 7.4, 9.5, 12.8, 15.5, and 19.5 (2θ±0.1 degrees).

Embodiment 49

The crystalline polymorph of embodiment 42, characterized in that it provides a XRPD pattern comprising each of the peaks selected from: 5.6, 5.8, 7.4, 9.5, 12.8, 15.5, and 19.5 (2θ±0.1 degrees).

Embodiment 50

The crystalline polymorph of any of embodiments 42, 48, and 49, characterized in that it provides a XRPD pattern in accordance with that shown in FIG. 10A.

Embodiment 51

The crystalline polymorph of any of embodiments 42 and 48-50, characterized in that it provides a DSC thermogram having endothermic peaks at 62±2° C. and 144±2° C.

Embodiment 52

Figure 10B:
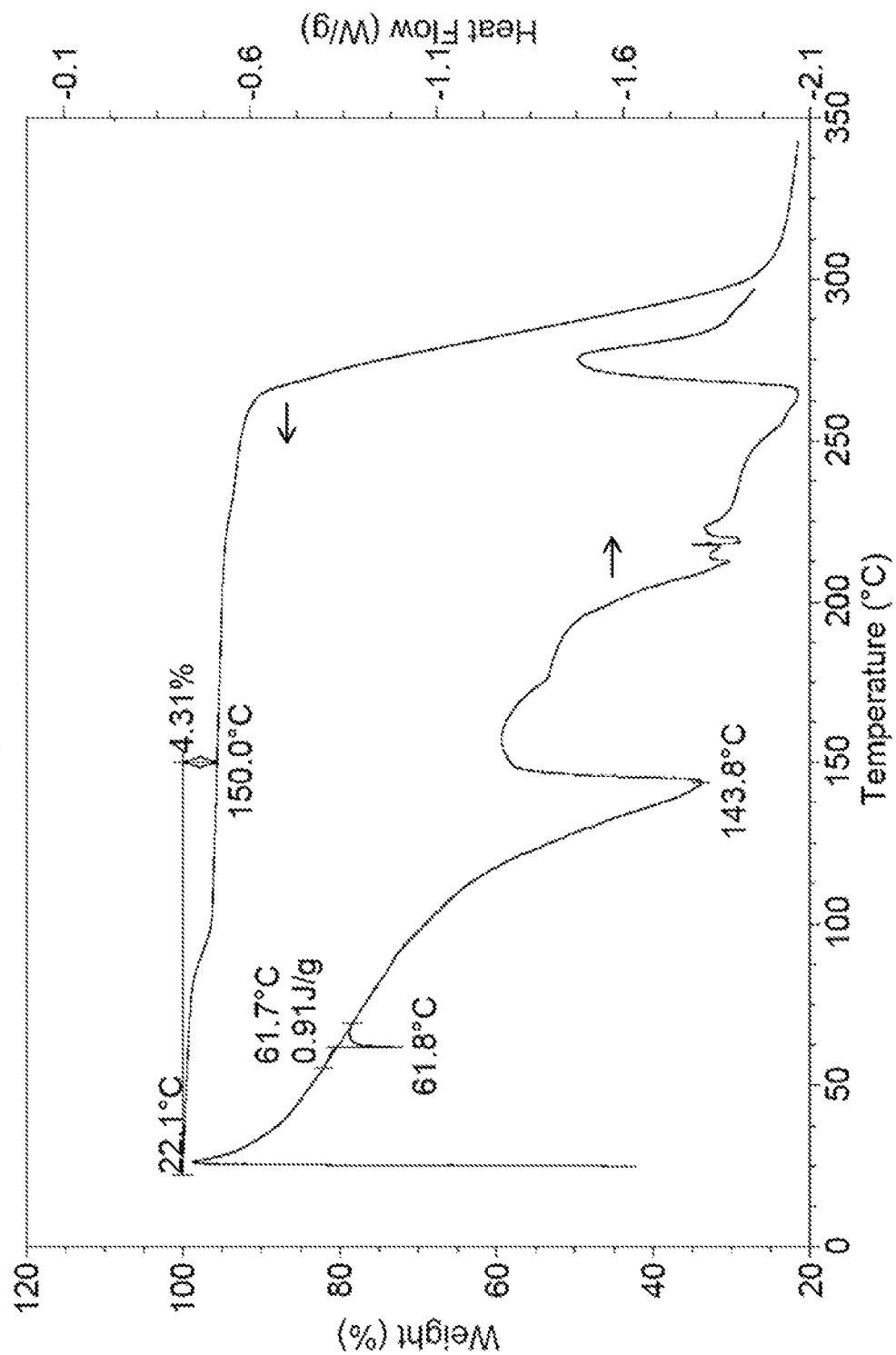
FIG. 10B shows a TGA and a DSC profile for the crystalline polymorph Form 10.

The crystalline polymorph of any of embodiments 42 and 48-51, characterized in that it provides a DSC thermogram in accordance with that shown in FIG. 10B.

Embodiment 53

A crystalline polymorph of sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

Embodiment 54

The crystalline polymorph of embodiment 53, characterized in that it provides a XRPD pattern comprising four or more (e.g., five or more) peaks selected from: 7.0, 10.4, 12.2, 13.1, 14.0, 18.8, and 24.5 (2θ±0.1 degrees).

Embodiment 55

The crystalline polymorph of embodiment 53, characterized in that it provides a XRPD pattern comprising each of the peaks selected from: 7.0, 10.4, 12.2, 13.1, 14.0, 18.8, and 24.5 (2θ±0.1 degrees).

Embodiment 56

The crystalline polymorph of any of embodiments 53-55, characterized in that it provides a XRPD pattern in accordance with that shown in FIG. 11A.

Embodiment 57

The crystalline polymorph of any of embodiments 53-56, characterized in that it provides a DSC thermogram having an endothermic peak at 76±2° C.

Embodiment 58

Figure 11B:
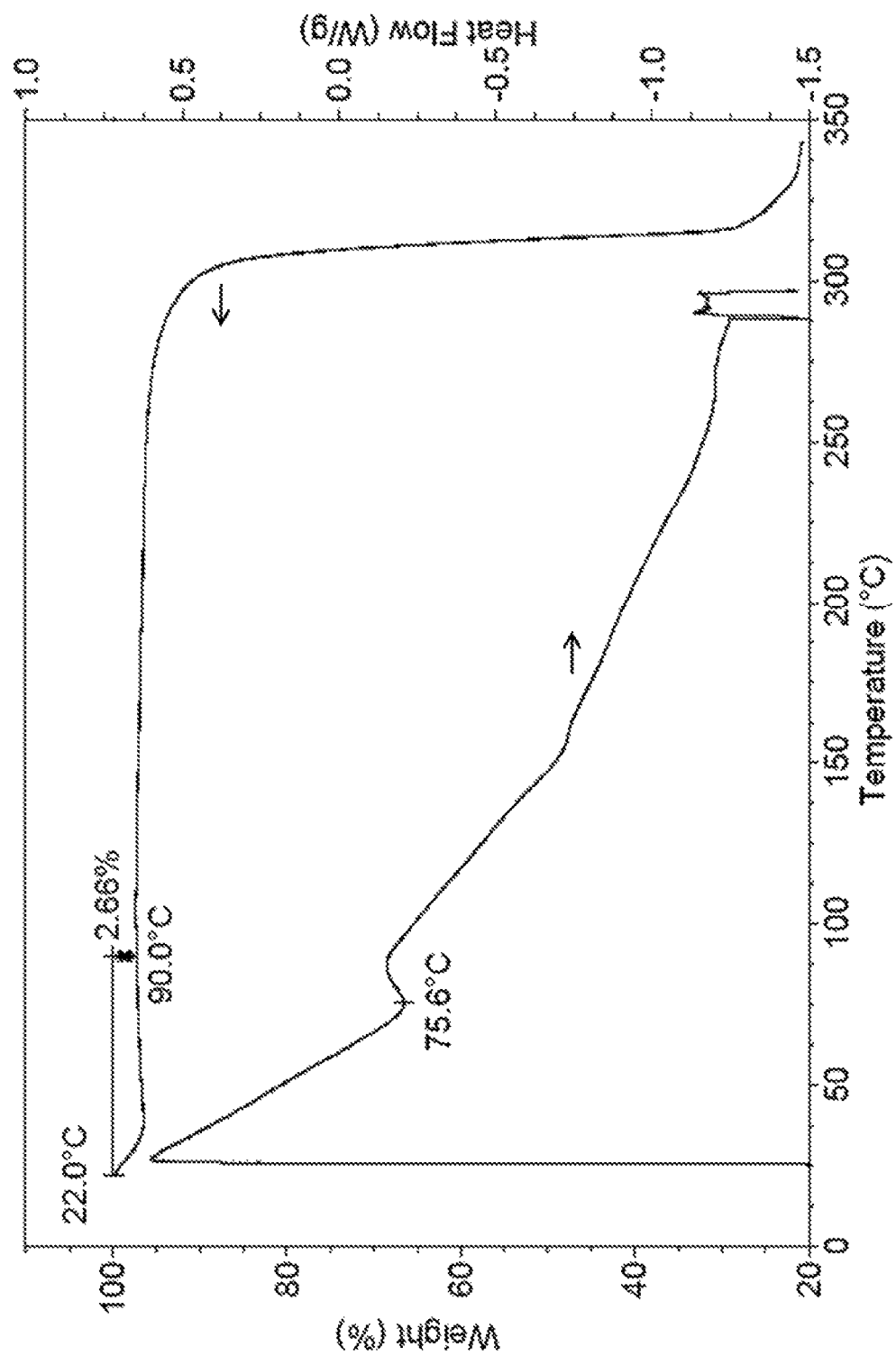
FIG. 11B shows a TGA and a DSC profile for the crystalline polymorph Form 11.

The crystalline polymorph of any of embodiments 53-57, characterized in that it provides a DSC thermogram in accordance with that shown in FIG. 11B.

Embodiment 59

The crystalline polymorph of embodiment 53, characterized in that it provides a XRPD pattern comprising four or more (e.g., five or more) peaks selected from: 3.8, 7.5, 13.0, 16.2, 17.0, 17.8, 20.0, 22.7, and 23.7 (2θ±0.1 degrees).

Embodiment 60

The crystalline polymorph of embodiment 53, characterized in that it provides a XRPD pattern comprising each of the peaks selected from: 3.8, 7.5, 13.0, 16.2, 17.0, 17.8, 20.0, 22.7, and 23.7 (2θ±0.1 degrees).

Embodiment 61

The crystalline polymorph of any of embodiments 53, 59, and 60, characterized in that it provides a XRPD pattern in accordance with that shown in FIG. 12A.

Embodiment 62

The crystalline polymorph of any of embodiments 53 and 59-61, characterized in that it provides a DSC thermogram having an endothermic peak at 153±2° C.

Embodiment 63

Figure 12B:
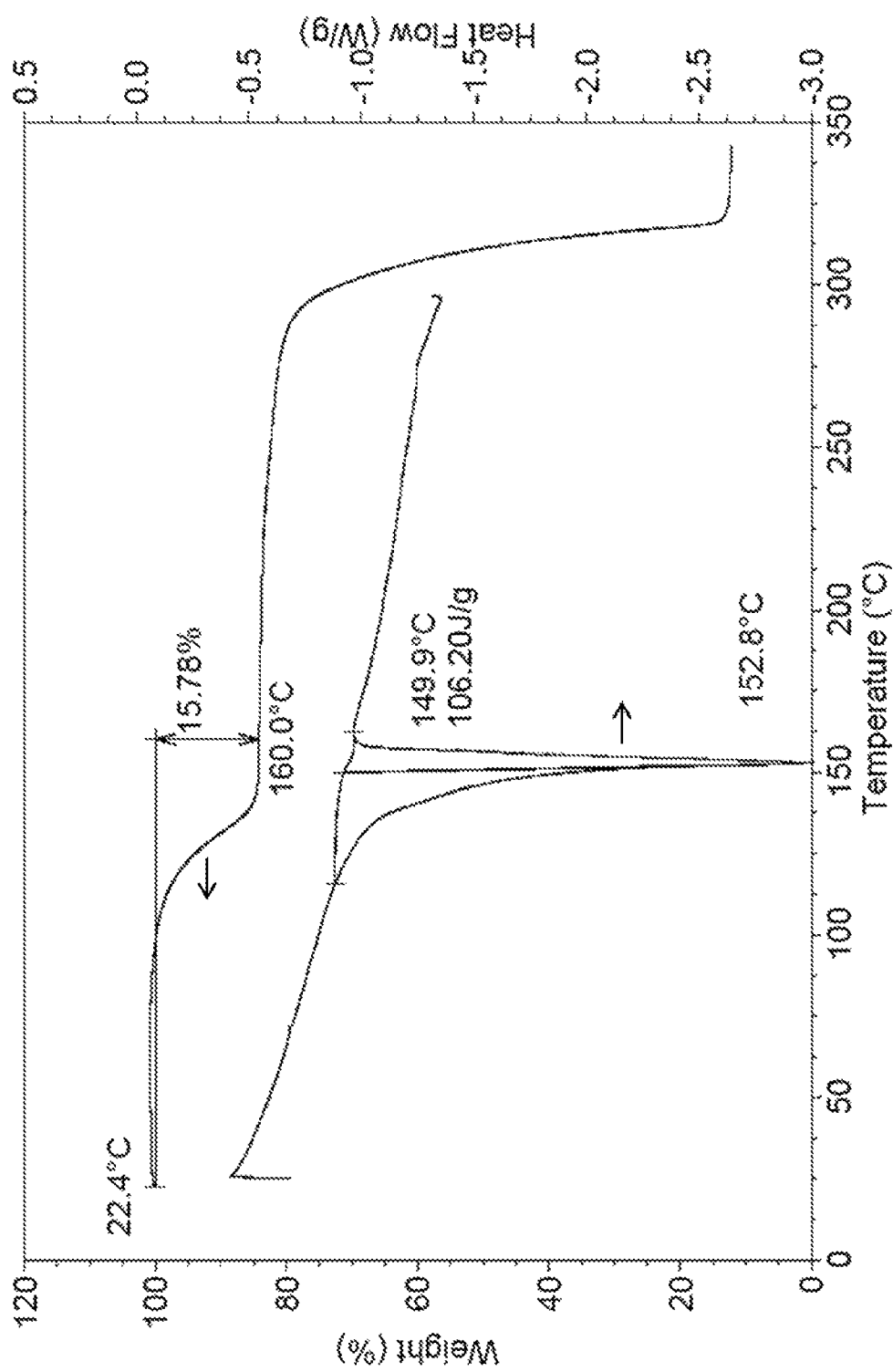
FIG. 12B shows a TGA and a DSC profile for the crystalline polymorph Form 12.

The crystalline polymorph of any of embodiments 53 and 59-62, characterized in that it provides a DSC thermogram in accordance with that shown in FIG. 12B.

Embodiment 64

A crystalline polymorph of L-arginine 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

Embodiment 65

The crystalline polymorph of embodiment 64, characterized in that it provides a XRPD pattern comprising four or more (e.g., five or more) peaks selected from: 10.3, 16.6, 18.7, 20.7, 21.3, 25.0, and 28.2 (2θ±0.1 degrees). L-Arginine Embodiment 66

The crystalline polymorph of embodiment 64, characterized in that it provides a XRPD pattern comprising each of the peaks selected from: 10.3, 16.6, 18.7, 20.7, 21.3, 25.0, and 28.2 (2θ±0.1 degrees). L-Arginine Embodiment 67

The crystalline polymorph of any of embodiments 64-66, characterized in that it provides a XRPD pattern in accordance with that shown in FIG. 13A.

Embodiment 68

The crystalline polymorph of any of embodiments 64-67, characterized in that it provides a DSC thermogram having an endothermic peak at 231±2° C.

Embodiment 69

Figure 13B:
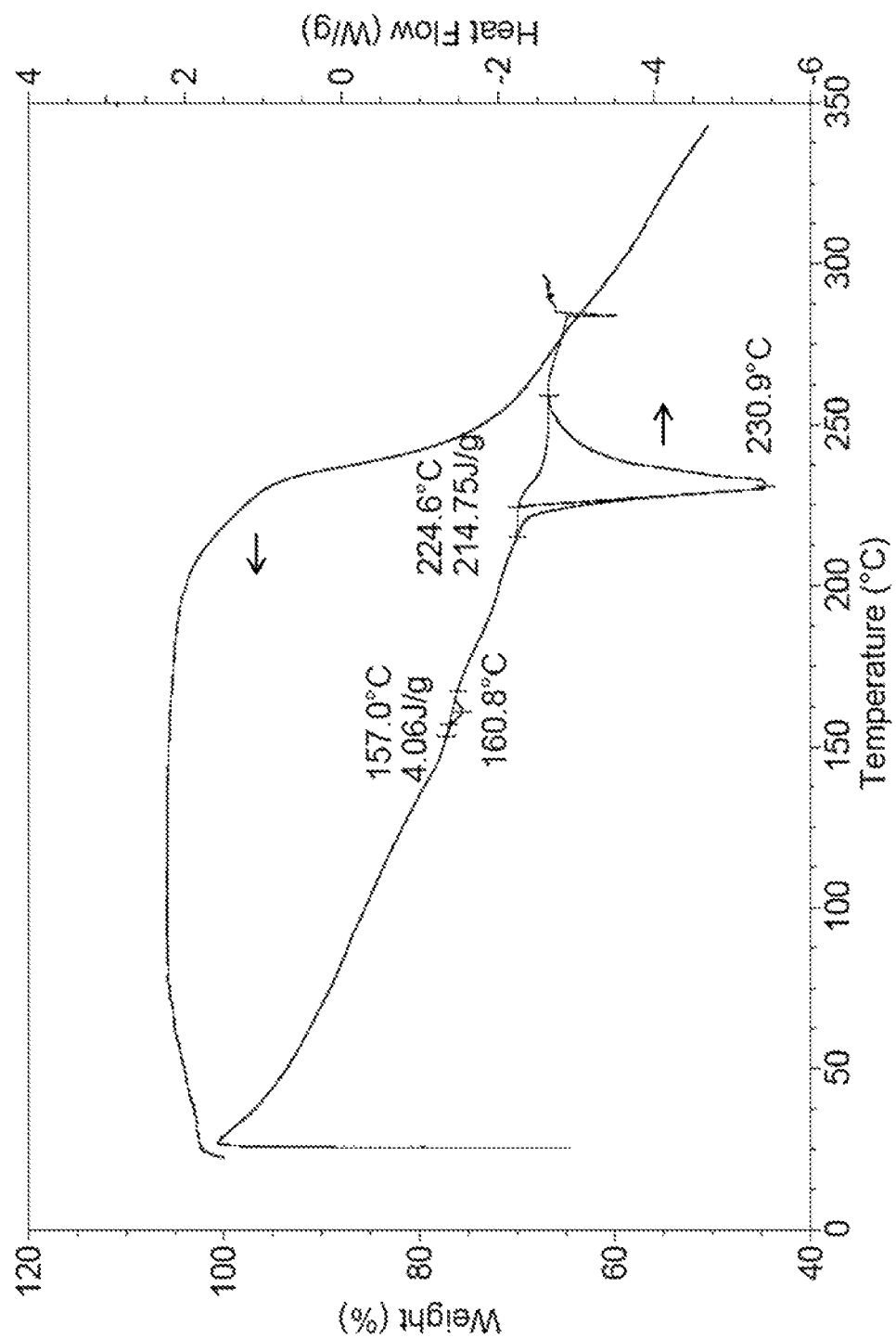
FIG. 13B shows a TGA and a DSC profile for the crystalline polymorph Form 13.

The crystalline polymorph of any of embodiments 64-68, characterized in that it provides a DSC thermogram in accordance with that shown in FIG. 13B.

Embodiment 70

A crystalline polymorph of magnesium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

Embodiment 71

The crystalline polymorph of embodiment 70, characterized in that it provides a XRPD pattern comprising four or more (e.g., five or more) peaks selected from: 5.4, 15.8, 16.8, 18.7, 25.1, and 38.2 (2θ±0.1 degrees).

Embodiment 72

The crystalline polymorph of embodiment 70, characterized in that it provides a XRPD pattern comprising each of the peaks selected from: 5.4, 15.8, 16.8, 18.7, 25.1, and 38.2 (2θ±0.1 degrees).

Embodiment 73

The crystalline polymorph of any of embodiments 70-72, characterized in that it provides a XRPD pattern in accordance with that shown in FIG. 14A.

Embodiment 74

The crystalline polymorph of any of embodiments 70-73, characterized in that it provides a DSC thermogram having endothermic peaks at 105±2° C. and 137±2° C.

Embodiment 75

Figure 14B:
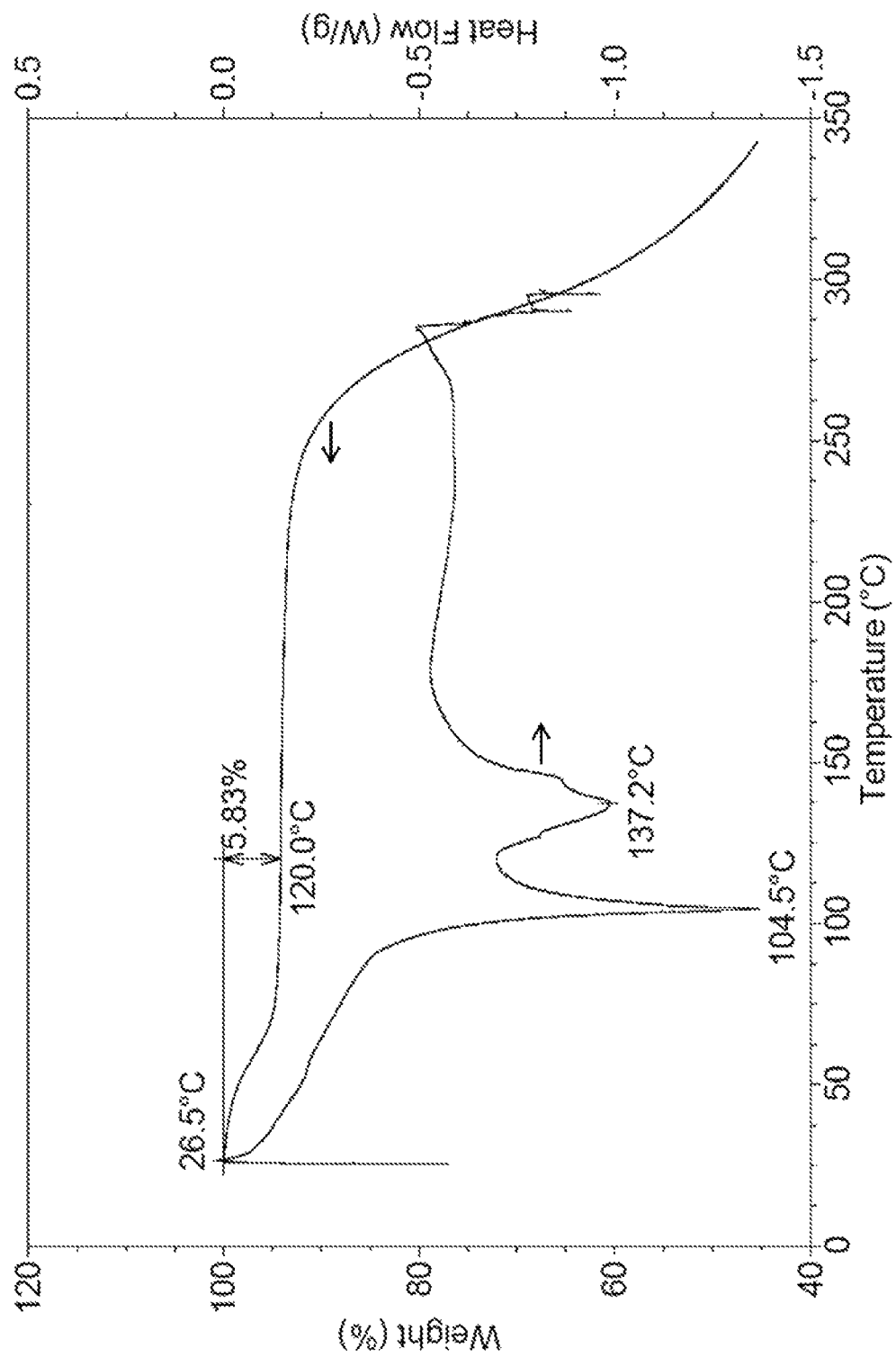
FIG. 14B shows a TGA and a DSC profile for the crystalline polymorph Form 14.

The crystalline polymorph of any of embodiments 70-74, characterized in that it provides a DSC thermogram in accordance with that shown in FIG. 14B.

Embodiment 76

A crystalline polymorph of urea 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

Embodiment 77

The crystalline polymorph of embodiment 76, characterized in that it provides a XRPD pattern comprising four or more (e.g., five or more) peaks selected from: 5.7, 9.8, 16.5, 17.3, 17.8, 20.0, 21.1, 23.5 and 26.1 (2θ±0.1 degrees).

Embodiment 78

The crystalline polymorph of embodiment 76, characterized in that it provides a XRPD pattern comprising each of the peaks selected from: 5.7, 9.8, 16.5, 17.3, 17.8, 20.0, 21.1, 23.5 and 26.1.

Embodiment 79

The crystalline polymorph of any of embodiments 76-78, characterized in that it provides a XRPD pattern in accordance with that shown in FIG. 15A.

Embodiment 80

The crystalline polymorph of any of embodiments 76-79, characterized in that it provides a DSC thermogram having an endothermic peak at 136±2° C.

Embodiment 81

Figure 15B:
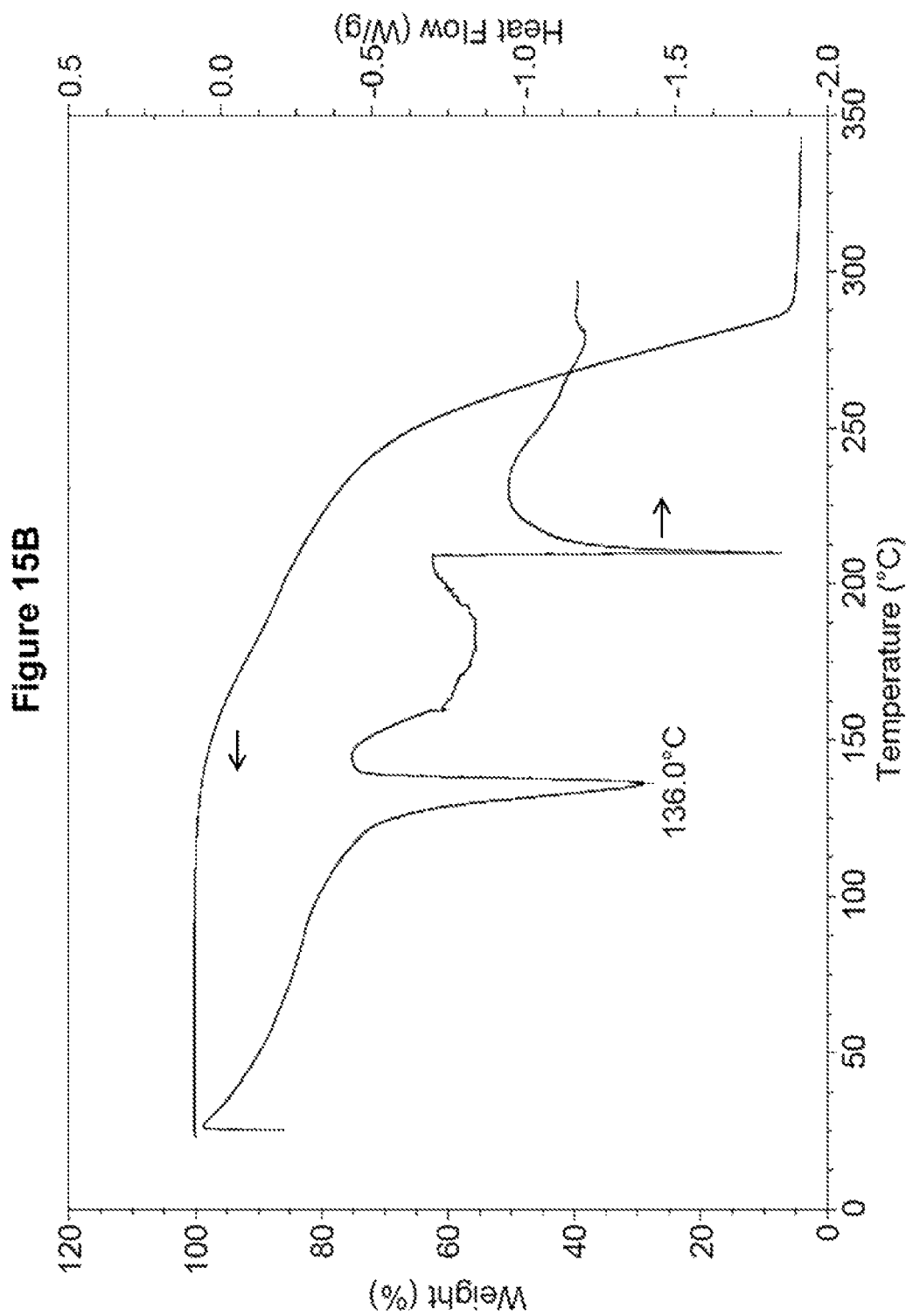
FIG. 15B shows a TGA and a DSC profile for the crystalline polymorph Form 15.

The crystalline polymorph of any of embodiments 76-80, characterized in that it provides a DSC thermogram in accordance with that shown in FIG. 15B.

Embodiment 82

A crystalline polymorph of L-proline 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof.

Embodiment 83

The crystalline polymorph of embodiment 82, characterized in that it provides a XRPD pattern comprising four or more (e.g., five or more) peaks selected from: 7.7, 7.9, 11.9, 15.9, 17.4, 19.7, and 21.4 (2θ±0.1 degrees).

Embodiment 84

The crystalline polymorph of embodiment 82, characterized in that it provides a XRPD pattern comprising each of the peaks selected from: 7.7, 7.9, 11.9, 15.9, 17.4, 19.7, and 21.4 (2θ±0.1 degrees).

Embodiment 85

The crystalline polymorph of any of embodiments 82-84, characterized in that it provides a XRPD pattern in accordance with that shown in FIG. 16A.

Embodiment 86

The crystalline polymorph of any of embodiments 82-85, characterized in that it provides a DSC thermogram having an endothermic peak at 168±2° C.

Embodiment 87

Figure 16B:
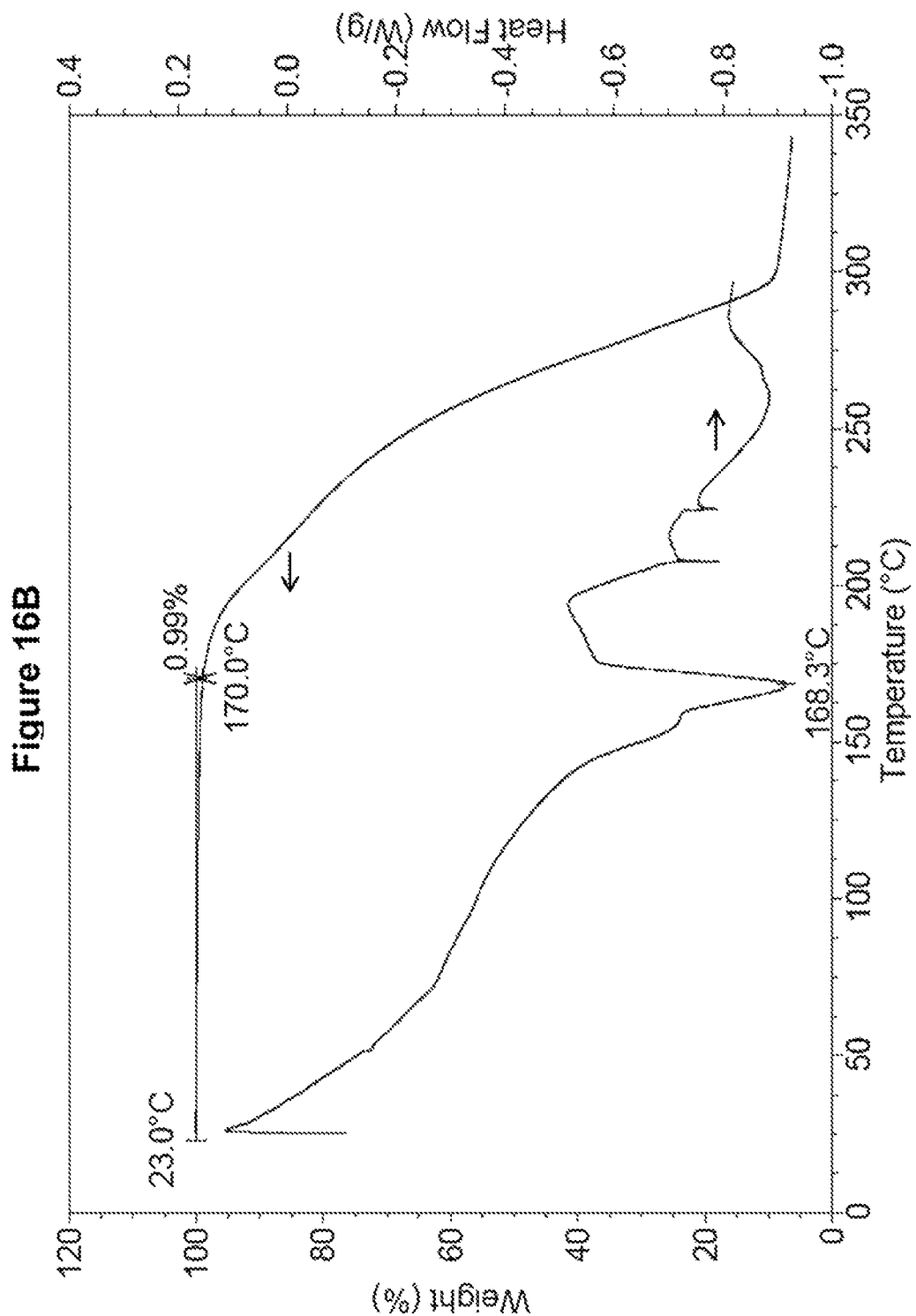
FIG. 16B shows a TGA and a DSC profile for the crystalline polymorph Form 16.

The crystalline polymorph of any of embodiments 82-86, characterized in that it provides a DSC thermogram in accordance with that shown in FIG. 16B.

Embodiment 88

A salt of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid, optionally the form of a hydrate or solvate thereof, selected from:
potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
magnesium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate;
urea 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate:
L-arginine 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate; and
L-proline 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate.

Embodiment 89

A pharmaceutical composition comprising a crystalline polymorph of any of embodiments 1-87 or a salt of embodiment 88, together with a pharmaceutically acceptable excipient, diluent, or carrier.

Embodiment 90

A method for treating a hyperproliferative disorder, e.g., a cancer, in a subject in need thereof, comprising administering to the subject an effective amount of a crystalline polymorph of any of embodiments 1-87 or a salt of embodiment 88.

Embodiment 91

A crystalline polymorph of any of embodiments 1-87 or a salt of embodiment 88 for use in the treatment of a hyperproliferative disorder, e.g., a cancer.

Embodiment 92

Use of a crystalline polymorph of any of embodiments 1-8 or a salt of embodiment 88 for the preparation of a medicament for the treatment of a hyperproliferative disorder, e.g., a cancer.

Embodiment 93

A method for inhibiting cell cycle progression in a cancer cell, the method comprising contacting the cancer cell with an effective amount of a crystalline polymorph of any of embodiments 1-87 or a salt of embodiment 88.

Embodiment 94

The method according to embodiment 93, wherein cell cycle progression is inhibited at the G0/G1 phase of the cell cycle.

Embodiment 95

A method for inducing apoptosis of a cancer cell, the method comprising contacting the cancer cell with an effective amount of a crystalline polymorph of any of embodiments 1-87 or a salt of embodiment 88.

Embodiment 96

A method for inducing a cytotoxic effect on a cancer cell, the method comprising contacting the cancer cell with an effective amount of a crystalline polymorph of any of embodiments 1-87 or a salt of embodiment 88.

Embodiment 97

A method for inhibiting glutathione synthesis in a cancer cell, the method comprising contacting the cancer cell with an effective amount of a crystalline polymorph of any of embodiments 1-87 or a salt of embodiment 88.

Embodiment 98

The method, crystalline polymorph, salt, or use according to any of embodiments 90-97, wherein the cancer is a hematopoetic cancer.

Embodiment 99

The method, crystalline polymorph, salt, or use according to any of embodiments 90-97, wherein the cancer is selected from a lymphoma (e.g., Burkitt's lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)), a leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia), and a plasma cell neoplasm (e.g., multiple myeloma).

Embodiment 100

The method, crystalline polymorph, salt, or use according to any of embodiments 90-97, wherein the cancer is selected from the group consisting of adrenocortical carcinoma, adrenal cortex cancer, AIDS-related cancers (e.g., as Kaposi sarcoma, AIDS-related lymphoma, Burkitt lymphoma, and primary CNS lymphoma), anal cancer, appendix cancer, astrocytomas (e.g., childhood cerebellar or cerebral), bile duct cancer (e.g., cholangiocarcinoma), bladder cancer, bone cancer (e.g., Ewing sarcoma, osteosarcoma and malignant fibrous histiocytoma), brain tumors (e.g., glioblastoma multiforme, cerebellar astrocytoma, cerebral astrocytoma/malignant glioma, ependymoma, medulloblastoma, oligodendroglioma, supratentorial primitive neuroectodermal tumors, and visual pathway and hypothalamic glioma), brainstem glioma, breast cancer, bronchial tumors, gastrointestinal carcinoid tumor, carcinoid tumors, carcinoma of unknown primary, cardiac (heart) tumors, central nervous system caner (e.g., atypical teratoid/rhabdoid tumor, embryonal tumors, and germ cell tumors), cervical cancer, childhood cancers, chondrosarcoma, chronic myeloproliferative neoplasms, colon and rectal cancer, craniopharyngioma, desmoplastic small round cell tumor, ductal carcinoma in situ (DCIS), endometrial cancer, ependymoma, epitheloid hemangioendothelioma (EHE), esophageal cancer, esthesioneuroblastoma, extracranial germ cell tumor, extragonadal germ cell tumor, eye cancer (e.g., intraocular melanoma, and retinoblastoma), fallopian tube cancer, gallbladder cancer, gastric (stomach) cancer, gastrointestinal stromal tumors (GIST), gestational trophoblastic disease (GTD), gliomas, hairy cell leukemia, head and neck cancer (e.g., head and neck squamous cell carcinoma (HNSCC)), hepatocellular (liver) cancer, histiocytosis, langerhans cell, hypopharyngeal cancer, kidney cancer, langerhans cell histiocytosis, laryngeal cancer, laryngeal cancer and papillomatosis, leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia), lip and oral cavity cancer, liver cancer, lung cancer (e.g., small cell lung cancer, non-small cell lung cancer (NSCLC), carcinoma of the lung, and squamous carcinoma of the lung), lung carcinoid tumor, lymphoma (e.g., Burkitt lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Wakdenström macroglobulinemia, primary central nervous System (CNS) lymphoma, and intravascular large B-cell lymphoma (ILBCL)), male breast cancer, meningiomas, mesothelioma, midline tract carcinoma involving NUT gene, mouth cancer, multiple endocrine neoplasia syndrome, plasma cell neoplasm (e.g., multiple myeloma), mycosis fungoides, myelodysplastic syndrome, myelodysplastic/myeloproliferative neoplasms and chronic myeloproliferative neoplasms, nasal cavity and paranasal sinus cancer, nasopharyngeal cancer (NPC), neuroblastoma, oral cancer, lip and oral cavity cancer and oropharyngeal cancer, ovarian cancer, pancreatic cancer and pancreatic neuroendocrine tumors (e.g., islet cell tumors), paraganglioma, parathyroid cancer, penile cancer, pharyngeal cancer, pheochromocytoma, pituitary tumor, pleuropulmonary blastoma, primary peritoneal cancer, prostate cancer, retinoblastoma, rhabdomyosarcoma, salivary gland cancer, Sezary syndrome, skin cancer (e.g., basal and squamous cell carcinoma, merkel cell carcinoma, and melanoma), small intestine cancer, soft tissue sarcoma, squamous cell carcinoma, stomach (gastric) cancer, testicular cancer, throat cancer, thymoma and thymic carcinoma, thyroid cancer, transitional cell cancer of the renal pelvis and ureter, urethral cancer, uterine cancer and uterine Sarcoma, vaginal cancer, vascular tumors, vulvar cancer, and Wilms tumor.

Embodiment 101

The method, crystalline polymorph, salt, or use according to any of embodiments 90-97, wherein the cancer is selected from the group consisting of appendix cancer, bone cancer (e.g., Ewing sarcoma, osteosarcoma and malignant fibrous histiocytoma), bronchial tumors, carcinoma of unknown primary, chronic myeloproliferative neoplasms, colon and rectal cancer, head and neck cancer (including head and neck squamous cell carcinoma (HNSCC)), leukemia (e.g., acute lymphoblastic leukemia (ALL), acute myeloid leukemia (AML), acute myeloblastic leukemia, chronic lymphocytic leukemia (CLL), chronic myelogenous leukemia (CML), chronic neutrophilic leukemia (CNL), chronic myelomonocytic leukaemia (CMML), aggressive NK-cell leukemia, acute biphenotypic leukaemia, and polycythemia vera), acute and chronic T-cell and B-cell leukemia), lymphoma (e.g., Burkitt lymphoma, Hodgkin's lymphoma, non-Hodgkin's lymphoma, hairy cell lymphoma, mantle cell lymphoma, T-cell lymphoma, cutaneous T-cell lymphoma, B-cell lymphoma, diffuse large B-cell lymphoma, double-hit lymphoma, Waldenström macroglobulinemia, primary central nervous System (CNS) lymphoma, and intravascular large B-cell lymphoma (ILBCL)), plasma cell neoplasms (e.g., multiple myeloma), myelodysplastic syndrome, myelodysplastic/myeloproliferative neoplasms and chronic myeloproliferative neoplasms, pancreatic cancer and pancreatic neuroendocrine tumors (e.g., islet cell tumors), small intestine cancer, soft tissue sarcoma, and squamous cell carcinoma.

Embodiment 102

The method, crystalline polymorph, salt, or use according to any of embodiments 90-97, wherein the cancer is diffuse large B-cell lymphoma.

Embodiment 103

The method, crystalline polymorph, salt, or use according to any of embodiments 90-97, wherein the cancer is a colorectal cancer.

Embodiment 104

The method, crystalline polymorph, salt, or use according to any of embodiments 90-103, wherein the cancer has a mutant KRAS gene.

Embodiment 105

The method, crystalline polymorph, salt, or use according to any of embodiments 90-103, wherein the cancer has a heterozygous mutant KRAS gene.

Numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A crystalline polymorph of 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylic acid, optionally in the form of a salt thereof and/or a hydrate or solvate thereof.

2. The crystalline polymorph of claim 1, wherein the polymorph is a polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid base compound, optionally in the form of a hydrate or solvate thereof.

3. The crystalline polymorph of claim 2, in the form of an anhydrate/ansolvate.

4. The crystalline polymorph of claim 3, characterized in that it provides an X-ray powder diffraction (XRPD) pattern comprising four or more peaks selected from: 6.1, 7.1, 9.4, 12.7, 18.8, 21.3, and 22.3 (2θ±0.1 degrees).

5. The crystalline polymorph of claim 1, which is in the form of a hydrate or solvate of 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylic acid.

6. The crystalline polymorph of claim 5, characterized in that it provides a XRPD pattern:
   (a) comprising four or more peaks selected from: 6.4, 14.4, 16.2, 17.5, 19.1, 22.8, and 24.0 (2θ±0.1 degrees);
   (b) comprising four or more peaks selected from: 9.9, 14.9, 19.4, 21.4, 23.5, and 24.1 (2θ±0.1 degrees);
   (c) comprising four or more (e.g., five or more) peaks selected from: 5.8, 11.5, 14.5, 17.3, 20.8, and 22.0 (2θ±0.1 degrees); or
   (d) comprising four or more (e.g., five or more) peaks selected from: 6.7, 7.0, 11.5, 13.1, 14.4, 17.2 and 22.1 (2θ±0.1 degrees).

7. The crystalline polymorph of claim 1, that is a crystalline polymorph of potassium 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylate, optionally the form of a hydrate or solvate thereof.

8. The crystalline polymorph of claim 7, characterized in that it provides a XRPD pattern:
   (a) comprising four or more peaks selected from: 6.4, 7.1, 10.2, 12.2, 14.2, 19.0, 19.4, and 24.5 (2θ±0.1 degrees); or
   (b) comprising four or more peaks selected from: 5.6, 5.8, 7.4, 9.5, 12.8, 15.5, and 19.5 (2θ±0.1 degrees).

9. The crystalline polymorph of claim 1, that is a crystalline polymorph of sodium 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylate, optionally the form of a hydrate or solvate thereof.

10. The crystalline polymorph of claim 9, characterized in that it provides a XRPD pattern:
    comprising four or more peaks selected from: 7.0, 10.4, 12.2, 13.1, 14.0, 18.8, and 24.5 (2θ±0.1 degrees).

11. The crystalline polymorph of claim 1, that is a crystalline polymorph of L-arginine 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylate, optionally the form of a hydrate or solvate thereof.

12. The crystalline polymorph of claim 11, characterized in that it provides a XRPD pattern comprising four or more peaks selected from: 10.3, 16.6, 18.7, 20.7, 21.3, 25.0, and 28.2 (2θ±0.1 degrees).

13. The crystalline polymorph of claim 1, that is a crystalline polymorph of magnesium 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylate, optionally the form of a hydrate or solvate thereof.

14. The crystalline polymorph of claim 13, characterized in that it provides a XRPD pattern comprising four or more peaks selected from: 5.4, 15.8, 16.8, 18.7, 25.1, and 38.2 (2θ±0.1 degrees).

15. The crystalline polymorph of claim 1, that is a crystalline polymorph of urea 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylate, optionally the form of a hydrate or solvate thereof.

16. The crystalline polymorph of claim 15, characterized in that it provides a XRPD pattern comprising four or more peaks selected from: 5.7, 9.8, 16.5, 17.3, 17.8, 20.0, 21.1, 23.5 and 26.1 (2θ±0.1 degrees).

17. The crystalline polymorph of claim 1, that is a crystalline polymorph of L-proline 4-(3-fluorophenyl)-1-(5-(isopropylthio)-4-(4-(trifluoromethyl)cyclohex-1-en-1-yl) thiazol-2-yl)-3-methyl-1H-pyrazole-5-carboxylate, optionally the form of a hydrate or solvate thereof.

18. The crystalline polymorph of claim 17, characterized in that it provides a XRPD pattern comprising four or more peaks selected from: 7.7, 7.9, 11.9, 15.9, 17.4, 19.7, and 21.4 (2θ±0.1 degrees).

19. A pharmaceutical composition comprising a crystalline polymorph of claim 1
    together with a pharmaceutically acceptable excipient, diluent, or carrier.

20. A method for treating a hyperproliferative disorder in a subject in need thereof, comprising administering to the subject an effective amount of a crystalline polymorph of claim 1.

21. A method for treating a hyperproliferative disorder in a subject in need thereof, comprising administering to the subject an effective amount of a crystalline polymorph of claim 10.

22. The crystalline polymorph of claim 3, characterized in that it provides an X-ray powder diffraction (XRPD) pattern;
    (a) comprising four or more peaks selected from: 6.2, 6.6, 7.5, 10.9, 12.4, and 13.3 (2θ±0.1 degrees); or
    (b) comprising four or more peaks selected from: 6.4, 9.1, 14.3, 16.6, 18.4, 20.1, and 21.9 (2θ±0.1 degrees).

23. The crystalline polymorph of claim 9, characterized in that it provides a XRPD pattern comprising four or more peaks selected from: 3.8, 7.5, 13.0, 16.2, 17.0, 17.8, 20.0, 22.7, and 23.7 (2θ±0.1 degrees).

24. A method for treating a hyperproliferative disorder in a subject in need thereof, comprising administering to the subject an effective amount of a crystalline polymorph of claim 4.

25. A crystalline polymorph of claim 1, wherein the polymorph is
    (1) a polymorph of 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid base compound, wherein
        (i) the crystalline polymorph is in the form of an anhydrate/ansolvate and provides an X-ray powder diffraction (XRPD) pattern
            (a) comprising four or more peaks selected from: 6.1, 7.1, 9.4, 12.7, 18.8, 21.3, and 22.3 (2θ±0.1 degrees);

(b) comprising four or more peaks selected from: 6.2, 6.6, 7.5, 10.9, 12.4, and 13.3 (2θ±0.1 degrees); or
(c) comprising four or more peaks selected from: 6.4, 9.1, 14.3, 16.6, 18.4, 20.1, and 21.9 (2θ±0.1 degrees); or
(ii) the crystalline polymorph is in the form of a hydrate or solvate provides an XRPD pattern:
(a) comprising four or more peaks selected from: 6.4, 14.4, 16.2, 17.5, 19.1, 22.8, and 24.0 (2θ±0.1 degrees);
(b) comprising four or more peaks selected from: 9.9, 14.9, 19.4, 21.4, 23.5, and 24.1 (2θ±0.1 degrees);
(c) comprising four or more (e.g., five or more) peaks selected from: 5.8, 11.5, 14.5, 17.3, 20.8, and 22.0 (2θ±0.1 degrees); or
(d) comprising four or more (e.g., five or more) peaks selected from: 6.7, 7.0, 11.5, 13.1, 14.4, 17.2 and 22.1 (2θ±0.1 degrees);
(2) a crystalline polymorph of potassium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof, that provides an XRPD pattern:
(a) comprising four or more peaks selected from: 6.4, 7.1, 10.2, 12.2, 14.2, 19.0, 19.4, and 24.5 (2θ±0.1 degrees); or
(b) comprising four or more peaks selected from: 5.6, 5.8, 7.4, 9.5, 12.8, 15.5, and 19.5 (2θ±0.1 degrees);
(3) a crystalline polymorph of sodium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof, that provides an XRPD pattern:
(a) comprising four or more peaks selected from: 7.0, 10.4, 12.2, 13.1, 14.0, 18.8, and 24.5 (2θ±0.1 degrees); or
(b) comprising four or more peaks selected from: 3.8, 7.5, 13.0, 16.2, 17.0, 17.8, 20.0, 22.7, and 23.7 (2θ±0.1 degrees);
(4) a crystalline polymorph of L-arginine 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof, that provides an XRPD pattern comprising four or more peaks selected from: 10.3, 16.6, 18.7, 20.7, 21.3, 25.0, and 28.2 (2θ±0.1 degrees);
(5) a crystalline polymorph of magnesium 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof, that provides an XRPD pattern comprising four or more peaks selected from: 5.4, 15.8, 16.8, 18.7, 25.1, and 38.2 (2θ±0.1 degrees);
(6) a crystalline polymorph of urea 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof, that provides an XRPD pattern comprising four or more peaks selected from: 5.7, 9.8, 16.5, 17.3, 17.8, 20.0, 21.1, 23.5 and 26.1 (2θ±0.1 degrees);
(7) a crystalline polymorph of L-proline 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally the form of a hydrate or solvate thereof, that provides an XRPD pattern comprising four or more peaks selected from: 7.7, 7.9, 11.9, 15.9, 17.4, 19.7, and 21.4 (2θ±0.1 degrees).

26. A pharmaceutical composition comprising a crystalline polymorph of claim 25 together with a pharmaceutically acceptable excipient, diluent, or carrier.

27. A method for treating a hyperproliferative disorder in a subject in need thereof, comprising administering to the subject an effective amount of a crystalline polymorph of claim 25.

* * * * *